(12) United States Patent
Schreiber

(10) Patent No.: US 10,669,548 B2
(45) Date of Patent: *Jun. 2, 2020

(54) NOTCH 1 SPECIFIC SIRNA MOLECULE

(71) Applicant: Soluventis GmbH, Bochum (DE)

(72) Inventor: Soren Schreiber, Witten (DE)

(73) Assignee: SOLUVENTIS GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,386

(22) Filed: Feb. 1, 2018

(65) Prior Publication Data

US 2018/0237785 A1    Aug. 23, 2018

Related U.S. Application Data

(62) Division of application No. 15/026,084, filed as application No. PCT/EP2014/002655 on Sep. 30, 2014, now Pat. No. 9,896,690.

(30) Foreign Application Priority Data

Sep. 30, 2013   (EP) .................................... 13004722

(51) Int. Cl.
| | | |
|---|---|---|
| *C12N 15/113* | (2010.01) | |
| *A61K 9/107* | (2006.01) | |
| *A61K 31/713* | (2006.01) | |
| *A61K 47/06* | (2006.01) | |

(52) U.S. Cl.
CPC ........ *C12N 15/1138* (2013.01); *A61K 9/1075* (2013.01); *A61K 31/713* (2013.01); *A61K 47/06* (2013.01); *C12N 15/1135* (2013.01); *C12N 2310/14* (2013.01); *C12N 2310/315* (2013.01); *C12N 2310/321* (2013.01); *C12N 2310/322* (2013.01); *C12N 2310/343* (2013.01); *C12N 2310/346* (2013.01); *C12N 2320/11* (2013.01); *C12N 2320/31* (2013.01); *C12N 2320/51* (2013.01); *C12N 2330/30* (2013.01)

(58) Field of Classification Search
CPC .............. C12N 15/113; C12N 2310/14; A01K 2207/05
See application file for complete search history.

(56) References Cited

U.S. PATENT DOCUMENTS 9,896,690 B2 *   2/2018   Schreiber ........... C12N 15/1135

FOREIGN PATENT DOCUMENTS

WO     WO-2013106494 A1 *  7/2013  ........... C12N 15/113

\* cited by examiner

*Primary Examiner* — Brian Whiteman

(57) ABSTRACT

The present invention is related to a nucleic acid molecule comprising a double-stranded structure, wherein the double-stranded structure is formed by a first strand and a second strand, wherein the first strand consist of the following nucleotide sequence 5' acGaGcUgGaCcAcUgGuCdT$_s$dT 3', and the second strand consists of the following nucleotide sequence 5' GAcCaGuGgUcCaGcUcGudT$_s$dT 3', wherein a minor nucleotide indicates that the nucleotide is 2'-F modified and an underlined nucleotide indicates that the nucleotide is 2'-0-methyl modified and wherein dT$_s$dT indicates that at the 3' end a dinucleotide is attached consisting of two dT nucleotides, wherein said two dTs are covalently linked through a phosphorothioate bond.

52 Claims, 9 Drawing Sheets

Specification includes a Sequence Listing.

Modification pattern:
- : parental sequence (unmodified)
I : intermediate stabilized
F: fully stabilized Modification pattern:
- : parental sequence (unmodified)
I : intermediate stabilized
F: fully stabilized

SEQUENCE LISTING

```
<160> NUMBER OF SEQ ID NOS: 128

<210> SEQ ID NO 1
<211> LENGTH: 19
<212> TYPE: RNA
<213> ORGANISM: Artificial
<220> FEATURE:
<223> OTHER INFORMATION: Synthetic

<400> SEQUENCE: 1
acgagcugga ccacugguc                                                  19

<210> SEQ ID NO 2
<211> LENGTH: 9309
<212> TYPE: DNA
<213> ORGANISM: Homo sapiens
<220> FEATURE:
<221> NAME/KEY: misc_feature
<223> OTHER INFORMATION: cDNA of human Notch 1

<400> SEQUENCE: 2
atgccgccgc tcctggcgcc cctgctctgc ctggcgctgc tgcccgcgct cgccgcacga      60
ggcccgcgat gctcccagcc cggtgagacc tgcctgaatg gcgggaagtg tgaagcggcc     120
aatggcacgg aggcctgcgt ctgtggcggg gccttcgtgg gccgcgatg ccaggacccc      180 aaccgtgcc tcagcacccc ctgcaagaac gccgggacat gccacgtggt ggaccgcaga     240
ggcgtggcag actatgcctg cagctgtgcc ctgggcttct ctgggcccct ctgcctgaca     300
cccctggaca tgcctgcct caccaacccc tgccgcaacg gggcacctg cgacctgctc       360 acgctgacgg agtacaagtg ccgctgcccg cccggctggt cagggaaatc gtgccagcag     420
gctgacccgt gcgcctccaa ccctgcgcc aacggtggc agtgcctgcc cttcgaggcc       480
tcctacatct gccactgccc acccagcttc catggcccca cctgccggca ggatgtcaac     540
gagtgtggcc agaagcccgg gctttgccgc cacgaggca cctgccacaa cgaggtcggc     600
tcctaccgct gcgtctgccg cgccacccac actggcccca actgcgagcg ccctacgtg      660 ccctgcagcc cctcgccctg ccagaacggg ggcacctgcc gccccacggg cgacgtcacc     720
cacgagtgtg cctgcctgcc aggcttcacc ggccagaact gtgaggaaaa tatcgacgat     780
tgtccaggaa acaactgcaa gaacggggt gcctgtgtgg acgcgtgaa cacctacaac      840 tgccgctgcc cgccagagtg gacaggtcag tactgtaccg aggatgtgga cgagtgccag     900
ctgatgccaa atgcctgcca gaacggcggg acctgccaca acacccacgg tggctacaac    960
tgcgtgtgtg tcaacggctg gactggtgag gactgcagcg agaacattga tgactgtgcc   1020
agcgccgcct gcttccacgg cgccacctgc catgaccgtg tggcctcctt ctactgcgag   1080
tgtccccatg gccgcacagg tctgctgtgc cacctcaacg acgcatgcat cagcaacccc   1140
tgtaacgagg gctccaactg cgacaccaac cctgtcaatg gcaaggccat ctgcacctgc   1200
ccctcggggt acacgggccc ggcctgcagc caggacgtta tgagtgctc gctgggtgcc    1260 aacccctgcg agcatgcggg caagtgcatc aaacacgctgg gctccttcga gtgccagtgt   1320
```

```
ctgcagggct acacgggccc ccgatgcgag atcgacgtca acgagtgcgt ctcgaacccg    1380
tgccagaacg acgccacctg cctggaccag attggggagt tccagtgcat ctgcatgccc    1440
ggctacgagg gtgtgcactg cgaggtcaac acagacgagt gtgccagcag cccctgcctg    1500
cacaatggcc gctgcctgga caagatcaat gagttccagt gcgagtgccc cacgggcttc    1560
actgggcatc tgtgccagta cgatgtggac gagtgtgcca gcacccctg caagaatggt      1620 gccaagtgcc tggacggacc caacacttac acctgtgtgt gcacggaagg gtacacgggg    1680
acgcactgcg aggtggacat cgatgagtgc gaccccgacc cctgccacta cggctcctgc    1740
aaggacggcc tcgccacctt cacctgcctc tgccgcccag gctacacggg ccaccactgc    1800
gagaccaaca tcaacgagtg ctccagccag ccctgccgcc acggggcac ctgccaggac      1860 cgcgacaacg cctacctctg cttctgcctg aaggggacca caggacccaa ctgcgagatc    1920
aacctggatg actgtgccag cagcccctgc gactcgggca cctgtctgga caagatcgat    1980
ggctacgagt gtgcctgtga gccgggctac acagggagca tgtgtaacat caacatcgat    2040
gagtgtgcgg gcaacccctg ccacaacggg ggcacctgcg aggacggcat caatggcttc    2100
acctgccgct gccccgaggg ctaccacgac cccacctgcc tgtctgaggt caatgagtgc    2160
aacagcaacc cctgcgtcca cggggcctgc cgggacagca tcaacgggta caagtgcgac    2220 tgtgacccctg ggtggagtgg gaccaactgt gacatcaaca acaatgagtg tgaatccaac    2280
ccttgtgtca acgcggcac ctgcaaagac atgaccagtg gctacgtgtg cacctgccgg      2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg ccccagccc ctgcagaaac      2520 ggcggggagt gcaggcaatc cgaggactat gagagcttct cctgtgtctg ccccacgggc    2580
tggcaagggc agacctgtga ggtcgacatc aacgagtgcg ttctgagccc gtgccggcac    2640
ggcgcatcct gccagaacac ccacggcggc taccgctgcc actgccaggc cggctacagt    2700
gggcgcaact gcgagaccga catcgacgac tgccggccca acccgtgtca acgggggc       2760 tcctgcacag acggcatcaa cacggccttc tgcgactgcc tgcccggctt ccggggcact    2820
ttctgtgagg aggacatcaa cgagtgtgcc agtgaccct gccgcaacgg ggccaactgc      2880
acggactgcg tggacagcta cgtgcacctg ccccgcag gcttcagcgg gatccactgt        2940
gagaacaaca cgcctgactg cacagagagc tcctgcttca cggtggcac ctgcgtggac      3000 ggcatcaact cgttcacctg cctgtgtcca cccggcttca cgggcagcta ctgccagcac    3060
gatgtcaatg agtgcgactc acagccctgc ctgcatggcg gcacctgtca ggacggctgc    3120
ggctcctaca ggtgcacctg cccccagggc tacactggcc ccaactgcca gaaccttgtg    3180
cactggtgtg actcctcgcc ctgcaagaac ggcggcaaat gctggcagac ccacacccag    3240
taccgctgcg agtgcccag cggctggacc ggcctttact gcgacgtgcc cagcgtgtcc      3300
tgtgaggtgg ctgcgcagcg acaaggtgtt gacgttgccc gcctgtgcca gcatggaggg    3360
ctctgtgtgg acgcgggcaa cacgcaccac tgccgctgcc aggcgggcta cacaggcagc    3420
tactgtgagg acctggtgga cgagtgctca cccagcccct gccagaacgg ggccacctgc    3480
acggactacc tgggcggcta ctcctgcaag tgcgtggccg gctaccacgg ggtgaactgc    3540
tctgaggaga tcgacgagtg cctctcccac ccctgccaga acggggcac ctgcctcgac      3600 ctcccccaaca cctacaagtg ctcctgccca cggggcactc agggtgtgca ctgtgagatc    3660
aacgtggacg actgcaatcc ccccgttgac cccgtgtccc ggagccccaa gtgctttaac    3720
```

```
aacggcacct gcgtggacca ggtgggcggc tacagctgca cctgcccgcc gggcttcgtg    3780
ggtgagcgct gtgaggggga tgtcaacgag tgcctgtcca atccctgcga cgcccgtggc    3840
acccagaact gcgtgcagcg cgtcaatgac ttccactgcg agtgccgtgc tggtcacacc    3900
gggcgccgct gcgagtccgt catcaatggc tgcaaaggca agccctgcaa gaatggggc    3960 acctgcgccg tggcctccaa caccgcccgc gggttcatct gcaagtgccc tgcgggcttc    4020
gagggcgcca cgtgtgagaa tgacgctcgt acctgcggca gcctgcgctg cctcaacggc    4080
ggcacatgca tctccggccc gcgcagcccc acctgctgt gcctgggccc cttcacgggc    4140
cccgaatgcc agttccccgg cagcagcccc tgcctgggcg gcaaccccctg ctacaaccag    4200 gggacctgtg agcccacatc cgagagcccc ttctaccgtt gcctgtgccc cgccaaattc    4260
aacgggctct tgtgccacat cctggactac agcttcgggg gtggggccgg gcgcgacatc    4320
cccccgccgc tgatcgagga ggcgtgcgag ctgcccgagt gccaggagga cgcgggcaac    4380
aaggtctgca gcctgcagtg caacaaccac gcgtgcggct gggacggcgg tgactgctcc    4440
ctcaacttca atgacccctg gaagaactgc acgcagtctc tgcagtgctg gaagtacttc    4500
agtgacggcc actgtgacag ccagtgcaac tcagccggct gcctcttcga cggctttgac    4560
tgccagcgtg cggaaggcca gtgcaacccc ctgtacgacc agtactgcaa ggaccacttc    4620
agcgacgggc actgcgacca gggctgcaac agcgcggagt gcgagtggga cgggctggac    4680
tgtgcggagc atgtacccga gaggctggcg gccggcacgc tggtggtggt ggtgctgatg    4740
ccgccggagc agctgcgcaa cagctccttc cacttcctgc gggagctcag ccgcgtgctg    4800
cacaccaacg tggtcttcaa gcgtgacgca cacggccagc agatgatctt ccctactac    4860 ggccgcgagg aggagctgcg caagcacccc atcaagcgtg ccgccgaggg ctgggccgca    4920
cctgacgccc tgctgggcca ggtgaaggcc tcgctgctcc ctggtggcag cgagggtggg    4980
cggcggcgga gggagctgga ccccatggac gtccgcggct ccatcgtcta cctggagatt    5040
gacaaccggc agtgtgtgca ggcctcctcg cagtgcttcc agagtgccac cgacgtggcc    5100
gcattcctgg agcgctcgc ctcgctgggc agcctcaaca tccctacaa gatcgaggcc    5160 gtgcagagtg agaccgtgga gccgcccccg ccggcgcagc tgcacttcat gtacgtggcg    5220
gcggccgcct ttgtgcttct gttcttcgtg ggctgcgggg tgctgctgtc ccgcaagcgc    5280
cggcggcagc atggccagct ctggttccct gagggcttca agtgtctga ggccagcaag    5340 aagaagcggc gggagcccct cggcgaggac tccgtgggcc tcaagccccct gaagaacgct    5400 tcagacggtg ccctcatgga cgacaaccag aatgagtggg gggacgagga cctggagacc    5460
aagaagttcc ggttcgagga gcccgtggtt ctgcctgacc tggacgacca gacagaccac    5520
cggcagtgga ctcagcagca cctggatgcc gctgacctgc gcatgtctgc catggcccc    5580 acaccgcccc agggtgaggt tgacgccgac tgcatggacg tcaatgtccg cgggcctgat    5640
ggcttcaccc cgctcatgat cgcctcctgc agcggggggcg gcctggagac gggcaacagc    5700
gaggaagagg aggacgcgcc ggccgtcatc tccgacttca tctaccaggg cgccagcctg    5760
cacaaccaga cagaccgcac gggcgagacc gccttgcacc tggccgcccg ctactcacgc    5820
tctgatgccg ccaagcgcct gctggaggcc agcgcagatg ccaacatcca ggacaacatg    5880
ggccgcaccc cgctgcatgc ggctgtgtct gccgacgcac aaggtgtctt ccagatcctg    5940
atccggaacc gagccacaga cctggatgcc cgcatgcatg atggcacgac gccactgatc    6000
ctggctgccc gcctggccgt ggagggcatg ctggaggacc tcatcaactc acacgccgac    6060
```

```
gtcaacgccg tagatgacct gggcaagtcc gccctgcact gggccgccgc cgtgaacaat    6120
gtggatgccg cagttgtgct cctgaagaac ggggctaaca aagatatgca gaacaacagg    6180
gaggagacac ccctgtttct ggccgcccgg gagggcagct acgagaccgc caaggtgctg    6240
ctggaccact tgccaaccg ggacatcacg gatcatatgg accgcctgcc gcgcgacatc    6300
gcacaggagc gcatgcatca cgacatcgtg aggctgctgg acgagtacaa cctggtgcgc    6360
agcccgcagc tgcacggagc cccgctgggg ggcacgccca ccctgtcgcc cccgctctgc    6420
tcgcccaacg gctacctggg cagcctcaag cccggcgtgc agggcaagaa ggtccgcaag    6480
cccagcagca aaggcctggc ctgtggaagc aaggaggcca aggacctcaa ggcacggagg    6540
aagaagtccc aggacggcaa gggctgcctg ctggacagct ccggcatgct ctcgcccgtg    6600
gactccctgg agtcacccca tggctacctg tcagacgtgg cctcgccgcc actgctgccc    6660
tccccgttcc agcagtctcc gtccgtgccc ctcaaccacc tgcctgggat gcccgacacc    6720
cacctgggca tcgggcacct gaacgtggcg gccaagcccg agatggcggc gctgggtggg    6780
ggcggccggc tggcctttga gactgggcca cctcgtctct cccacctgcc tgtggcctct    6840
ggcaccagca ccgtcctggg ctccagcagc ggaggggccc tgaatttcac tgtgggcggg    6900
tccaccagtt tgaatggtca atgcgagtgg ctgtcccggc tgcagagcgg catggtgccg    6960
aaccaataca accctctgcg ggggagtgtg gcaccaggcc ccctgagcac acaggccccc    7020
tccctgcagc atggcatggt aggcccgctg cacagtagcc ttgctgccag cgccctgtcc    7080
cagatgatga gctaccaggg cctgcccagc accggctggg ccacccagcc tcacctggtg    7140
cagacccagc aggtgcagcc acaaaactta cagatgcagc agcagaacct gcagccagca    7200
aacatccagc agcagcaaag cctgcagccg ccaccaccac caccacagcc gcaccttggc    7260
gtgagctcag cagccagcgg ccacctgggc cggagcttcc tgagtggaga gccgagccag    7320
gcagacgtgc agccactggg ccccagcagc ctggcggtgc acactattct gccccaggag    7380
agccccgccc tgcccacgtc gctgccatcc tcgctggtcc cacccgtgac cgcagcccag    7440
ttcctgacgc cccctcgca gcacagctac tcctcgcctg tggacaacac cccagccac    7500 cagctacagg tgcctgagca ccccttcctc acccgtccc ctgagtcccc tgaccagtgg    7560
tccagctcgt ccccgcattc caacgtctcc gactggtccg agggcgtctc cagccctccc    7620
accagcatgc agtcccagat cgcccgcatt ccggaggcct tcaagtaaac ggcgcgcccc    7680
acgagacccc ggcttccttt cccaagcctt cgggcgtctg tgtgcgctct gtggatgcca    7740
gggccgacca gaggagcctt tttaaaacac atgttttat acaaaataag aacgaggatt    7800 ttaattttt ttagtattta tttatgtact tttattttac acagaaacac tgcctttta    7860 tttatatgta ctgtttatc tggccccagg tagaaacttt tatctattct gagaaaacaa    7920
gcaagttctg agagccaggg ttttcctacg taggatgaaa agattcttct gtgtttataa    7980
aatataaaca aagattcatg atttataaat gccatttatt tattgattcc tttttttcaaa   8040 atccaaaaag aaatgatgtt ggagaaggga agttgaacga gcatagtcca aaaagctcct    8100
ggggcgtcca ggccgcgccc tttccccgac gcccacccaa ccccaagcca gcccggccgc    8160
tccaccagca tcacctgcct gttaggagaa gctgcatcca gaggcaaacg gaggcaaagc    8220
tggctcacct tccgcacgcg gattaattg catctgaaat aggaaacaag tgaaagcata    8280
tgggttagat gttgccatgt gttttagatg gtttcttgca agcatgcttg tgaaaatgtg    8340
ttctcggagt gtgtatgcca agagtgcacc catggtacca atcatgaatc tttgtttcag    8400
gttcagtatt atgtagttgt tcgttggtta tacaagttct tggtccctcc agaaccaccc    8460
```

```
cggccccctg cccgttcttg aaatgtaggc atcatgcatg tcaaacatga gatgtgtgga   8520
ctgtggcact tgcctgggtc acacacggag gcatcctacc cttttctggg gaaagacact   8580
gcctgggctg accccggtgg cggccccagc acctcagcct gcacagtgtc ccccaggttc   8640
cgaagaagat gctccagcaa cacagcctgg gcccagctc gcgggacccg accccccgtg    8700
ggctcccgtg ttttgtagga gacttgccag agccgggcac attgagctgt gcaacgccgt   8760
gggctgcgtc ctttggtcct gtccccgcag ccctggcagg gggcatgcgg tcgggcaggg   8820
gctggaggga ggcggggggct gcccttgggc caccctcct agtttgggag gagcagattt    8880
ttgcaatacc aagtatagcc tatggcagaa aaaatgtctg taaatatgtt tttaaaggtg   8940
gattttgttt aaaaaatctt aatgaatgag tctgttgtgt gtcatgccag tgagggacgt   9000
cagacttggc tcagctcggg gagccttagc cgcccatgca ctggggacgc tccgctgccg   9060
tgccgcctgc actcctcagg gcagcctccc ccggctctac gggggccgcg tggtgccatc   9120 cccaggggc atgaccagat gcgtcccaag atgttgattt ttactgtgtt ttataaaata    9180
gagtgtagtt tacagaaaaa gactttaaaa gtgatctaca tgaggaactg tagatgatgt   9240 attttttttca tctttttttgt taactgattt gcaataaaaa tgatactgat ggtgaaaaaa   9300
aaaaaaaaa                                                          9309

<210> SEQ ID NO 3
<211> LENGTH: 19
<212> TYPE: RNA
<213> ORGANISM: Artificial
<220> FEATURE:
<223> OTHER INFORMATION: Synthetic

<400> SEQUENCE: 3
gaccaguggu ccagcucgu                                                   19

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
acgagcugga ccacugguct t                                                21

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
gaccaguggu ccagcucgut t                                                21

<210> SEQ ID NO 6
<211> LENGTH: 19
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-F modified
<220> FEATURE:
```

<221> NAME/KEY: misc_feature
<222> LOCATION: (2)..(2)
<223> OTHER INFORMATION: Nucleotide is 2'-F modified
<220> FEATURE:
<221> NAME/KEY: misc_feature
<222> LOCATION: (3)..(3)
<223> OTHER INFORMATION: Nucleotide is 2'-O-methyl modified
<220> FEATURE:
<221> NAME/KEY: misc_feature
<222> LOCATION: (4)..(4)
<223> OTHER INFORMATION: Nucleotide is 2'-F modified
<220> FEATURE:
<221> NAME/KEY: misc_feature
<222> LOCATION: (5)..(5)
<223> OTHER INFORMATION: Nucleotide is 2'-O-methyl modified
<220> FEATURE:
<221> NAME/KEY: misc_feature
<222> LOCATION: (6)..(6)
<223> OTHER INFORMATION: Nucleotide is 2'-F modified
<220> FEATURE:
<221> NAME/KEY: misc_feature
<222> LOCATION: (7)..(7)
<223> OTHER INFORMATION: Nucleotide is 2'-O-methyl modified
<220> FEATURE:
<221> NAME/KEY: misc_feature
<222> LOCATION: (8)..(8)
<223> OTHER INFORMATION: Nucleotide is 2'-F modified
<220> FEATURE:
<221> NAME/KEY: misc_feature
<222> LOCATION: (9)..(9)
<223> OTHER INFORMATION: Nucleotide is 2'-O-methyl modified
<220> FEATURE:
<221> NAME/KEY: misc_feature
<222> LOCATION: (10)..(10)
<223> OTHER INFORMATION: Nucleotide is 2'-F modified
<220> FEATURE:
<221> NAME/KEY: misc_feature
<222> LOCATION: (11)..(11)
<223> OTHER INFORMATION: Nucleotide is 2'-O-methyl modified
<220> FEATURE:
<221> NAME/KEY: misc_feature
<222> LOCATION: (12)..(12)
<223> OTHER INFORMATION: Nucleotide is 2'-F modified
<220> FEATURE:
<221> NAME/KEY: misc_feature
<222> LOCATION: (13)..(13)
<223> OTHER INFORMATION: Nucleotide is 2'-O-methyl modified
<220> FEATURE:
<221> NAME/KEY: misc_feature
<222> LOCATION: (14)..(14)
<223> OTHER INFORMATION: Nucleotide is 2'-F modified
<220> FEATURE:
<221> NAME/KEY: misc_feature
<222> LOCATION: (15)..(15)
<223> OTHER INFORMATION: Nucleotide is 2'-O-methyl modified
<220> FEATURE:
<221> NAME/KEY: misc_feature
<222> LOCATION: (16)..(16)
<223> OTHER INFORMATION: Nucleotide is 2'-F modified
<220> FEATURE:
<221> NAME/KEY: misc_feature
<222> LOCATION: (17)..(17)
<223> OTHER INFORMATION: Nucleotide is 2'-O-methyl modified
<220> FEATURE:
<221> NAME/KEY: misc_feature
<222> LOCATION: (18)..(18)
<223> OTHER INFORMATION: Nucleotide is 2'-F modified
<220> FEATURE:
<221> NAME/KEY: misc_feature
<222> LOCATION: (19)..(19)
<223> OTHER INFORMATION: Nucleotide is 2'-O-methyl modified

<400> SEQUENCE: 6
acgagcugga ccacugguc                                              19

<210> SEQ ID NO 7
<211> LENGTH: 19

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-O-methyl modified
<220> FEATURE:
<221> NAME/KEY: misc_feature
<222> LOCATION: (2)..(2)
<223> OTHER INFORMATION: Nucleotide is 2'-O-methyl modified
<220> FEATURE:
<221> NAME/KEY: misc_feature
<222> LOCATION: (3)..(3)
<223> OTHER INFORMATION: Nucleotide is 2'-F modified
<220> FEATURE:
<221> NAME/KEY: misc_feature
<222> LOCATION: (4)..(4)
<223> OTHER INFORMATION: Nucleotide is 2'-O-methyl modified
<220> FEATURE:
<221> NAME/KEY: misc_feature
<222> LOCATION: (5)..(5)
<223> OTHER INFORMATION: Nucleotide is 2'-F modified
<220> FEATURE:
<221> NAME/KEY: misc_feature
<222> LOCATION: (6)..(6)
<223> OTHER INFORMATION: Nucleotide is 2'-O-methyl modified
<220> FEATURE:
<221> NAME/KEY: misc_feature
<222> LOCATION: (7)..(7)
<223> OTHER INFORMATION: Nucleotide is 2'-F modified
<220> FEATURE:
<221> NAME/KEY: misc_feature
<222> LOCATION: (8)..(8)
<223> OTHER INFORMATION: Nucleotide is 2'-O-methyl modified
<220> FEATURE:
<221> NAME/KEY: misc_feature
<222> LOCATION: (9)..(9)
<223> OTHER INFORMATION: Nucleotide is 2'-Fmodified
<220> FEATURE:
<221> NAME/KEY: misc_feature
<222> LOCATION: (10)..(10)
<223> OTHER INFORMATION: Nucleotide is 2'-O-methyl modified
<220> FEATURE:
<221> NAME/KEY: misc_feature
<222> LOCATION: (11)..(11)
<223> OTHER INFORMATION: Nucleotide is 2'-F modified
<220> FEATURE:
<221> NAME/KEY: misc_feature
<222> LOCATION: (12)..(12)
<223> OTHER INFORMATION: Nucleotide is 2'-O-methyl modified
<220> FEATURE:
<221> NAME/KEY: misc_feature
<222> LOCATION: (13)..(13)
<223> OTHER INFORMATION: Nucleotide is 2'-F modified
<220> FEATURE:
<221> NAME/KEY: misc_feature
<222> LOCATION: (14)..(14)
<223> OTHER INFORMATION: Nucleotide is 2'-O-methyl modified
<220> FEATURE:
<221> NAME/KEY: misc_feature
<222> LOCATION: (15)..(15)
<223> OTHER INFORMATION: Nucleotide is 2'-Fmodified
<220> FEATURE:
<221> NAME/KEY: misc_feature
<222> LOCATION: (16)..(16)
<223> OTHER INFORMATION: Nucleotide is 2'-O-methyl modified
<220> FEATURE:
<221> NAME/KEY: misc_feature
<222> LOCATION: (17)..(17)
<223> OTHER INFORMATION: Nucleotide is 2'-F modified
<220> FEATURE:
<221> NAME/KEY: misc_feature
<222> LOCATION: (18)..(18)
<223> OTHER INFORMATION: Nucleotide is 2'-O-methyl  modified
<220> FEATURE:
<221> NAME/KEY: misc_feature
<222> LOCATION: (19)..(19)
```

<223> OTHER INFORMATION: Nucleotide is 2'-F modified

<400> SEQUENCE: 7
gaccaguggu ccagcucgu                                                        19

<210> SEQ ID NO 8
<211> LENGTH: 17
<212> TYPE: RNA
<213> ORGANISM: Artificial
<220> FEATURE:
<223> OTHER INFORMATION: Synthetic

<400> SEQUENCE: 8
cgagcuggac cacuggu                                                          17

<210> SEQ ID NO 9
<211> LENGTH: 17
<212> TYPE: RNA
<213> ORGANISM: Artificial
<220> FEATURE:
<223> OTHER INFORMATION: Synthetic

<400> SEQUENCE: 9
accagugguc cagcucg                                                          17

<210> SEQ ID NO 10
<211> LENGTH: 19
<212> TYPE: DNA
<213> ORGANISM: Artificial
<220> FEATURE:
<223> OTHER INFORMATION: Synthetic

<400> SEQUENCE: 10
cgagcuggac cacuggutt                                                        19

<210> SEQ ID NO 11
<211> LENGTH: 19
<212> TYPE: DNA
<213> ORGANISM: Artificial
<220> FEATURE:
<223> OTHER INFORMATION: Synthetic

<400> SEQUENCE: 11
accagugguc cagcucgtt                                                        19

<210> SEQ ID NO 12
<211> LENGTH: 9309
<212> TYPE: RNA
<213> ORGANISM: Homo sapiens
<220> FEATURE:
<221> NAME/KEY: misc_feature
<223> OTHER INFORMATION: mRNA dervied from cDNA of human Notch 1

<400> SEQUENCE: 12
augccgccgc uccuggcgcc ccugcucugc cuggcgcugc ugcccgcgcu cgccgcacga           60
ggcccgcgau gcucccagcc cggugagacc ugccugaaug gcgggaagug ugaagcggcc          120
aauggcacgg aggccugcgu cuguggcggg gccuucgugg gcccgcgaug ccaggacccc          180
aacccgugcc ucagcacccc cugcaagaac gcgggacau gccacguggu ggaccgcaga           240
ggcguggcag acuaugccug cagcugugcc cugggcuucu cuggcccccu cugccugaca          300 cccucuggaca augccugccu caccaacccc ugcgcaacg ggggcaccug cgaccugcuc          360
acgcugacgg aguacaagug ccgcugcccg cccggcuggu cagggaaauc gugccagcag          420

```
gcugacccgu gcgccuccaa ccccugcgcc aacgguggcc agugccugcc cuucgaggcc      480
uccuacaucu gccacugccc acccagcuuc cauggcccca ccugccggca ggaugucaac      540 gagugguggcc agaagcccgg gcuuugccgc cacggaggca ccugccacaa cgaggucggc     600
uccuaccgcu cgcucugccg cgccacccac acuggcccca acugcgagcg cccuacgug       660 cccugcagcc ccucgcccug ccagaacggg ggcaccugcc gccccacggg cgacgucacc      720
cacgagugug ccugccugcc aggcuuccuc ggccagaacu gugaggaaaa uaucgacgau      780
uguccaggaa acaacugcaa gaacgggggu gccugugugg acggcgugaa caccuacaac      840
ugccgcugcc cgccagagug gacaggucag uacuguaccg aggaugugga cgagugccag      900
cugaugccaa augccugcca gaacggcggg accugccaca cacccacgg uggcuacaac       960 ugcgugugug ucaacggcug gacuggugag gacugcagcg agaacauuga ugacugugcc     1020
agcgccgccu gcuuccacgg cgccaccugc caugaccgug uggccuccuu cuacugcgag     1080 ugucccaug gccgcacagg ucugcugugc caccucaacg acgcaugcau cagcaaccccc      1140 uguaacgagg gcuccaacug cgacaccaac ccugucaaug gcaaggccau cugcaccugc     1200 cccucgggu acacgggccc ggccugcagc caggacgugg augagugcuc gcugggugcc      1260
aaccccugcg agcaugcggg caagugcauc aacacgcugg gcuccuucga gugccagugu     1320
cugcagggcu acacgggccc ccgaugcgag aucgacguca acgagugcgu ucgaacccg      1380 ugccagaacg acgccaccug ccuggaccag auuggggagu uccagugcau cugcaugccc     1440
ggcuacgagg gugugcacug cgaggucaac acagacgagu gugccagcag cccccugccug    1500 cacaauggcc gcugccugga caagaucaau gaguuccagu gcgagugccc cacgggcuuc     1560
acugggcauc ugugccagua cgaugugac gagugugcca gccccccug caagaauggu       1620 gccaagugcc uggacggacc caacacuuac accugugugu gcacggaagg guacacgggg    1680
acgcacugcg aggugggacau cgaugagugc gaccccgacc ccugccacua cggcuccugc    1740
aaggacggcu cgccaccuu caccugccuc ugccgcccag gcuacacggg ccaccacugc     1800
gagaccaaca ucaacgagug cuccagccag cccugccgcc acggggggcac cugccaggac   1860 cgcgacaacg ccuaccucug cuucugccug aaggggacca caggaccaa cugcgagauc     1920 aaccuggaug acugugccag cagcccugc gacucgggca ccugucugga caagaucgau     1980
ggcuacgagu gugccggua gccgggcuac acagggagca uguguaacau caacaucgau    2040
gagugugcgg gcaacccccug ccacaacggg ggcaccugcg aggacggcau caauggcuuc    2100
accugccgcu gccccgaggg cuaccacgac cccaccugcc ugucgggu caaugagugc      2160 aacagcaacc ccugcgucca ggggccugc cgggacagcc ucaacgggua caagugcgac     2220
ugugacccug gguggagugg gaccaacugu gacaucaaca caaugagug ugaauccaac     2280 ccuugugca acggcggcac cugcaaagac augaccagug gcuacgugug caccugccgg    2340
gagggcuuca gcgguccccaa cugccagacc aacaucaacg agugugcuc caacccaaugu  2400 cugaaccagg gcacguguau ugacgacguu gccggguaca agucaacug ccugcugccc    2460 uacacagggug ccacguguga gguggucgu gccccugug ccccccagccc cugcagaaac   2520 ggcgggagu gcaggcaauc cgaggacuau gagagcuucu ccugugucug ccccacgggc     2580
uggcaagggc agaccuguga ggucgacauc aacgagugcg uucugagccc gugccggcac    2640
ggcgcauccu gccagaacac ccacggcggu uaccgcugcc acugccaggc cggcuacagu   2700
gggcgcaacu gcgagaccga caucgacgac ugccggcccca acccgugca caacgggggc    2760 uccugcacag acggcaucaa cacggccuc ugcgacugcc ugcccggcuu ccggggcacu    2820
```

```
uucugugagg aggacaucaa cgagugugcc agugaccccu gccgcaacgg ggccaacugc    2880
acggacugcg uggacagcua cacgugcacc ugccccgcag gcuucagcgg gauccacugu    2940
gagaacaaca cgccugacug cacagagagc uccugcuuca acgguggcac cugcguggac    3000
ggcaucaacu cguucaccug ccugugucca cccggcuuca cgggcagcua cugccagcac    3060
gaugucaaug agugcgacuc acagcccugc cugcauggcg gcaccuguca ggacggcugc    3120
ggcuccuaca ggugcaccug cccccagggc uacacuggcc caacugcca gaaccuugug    3180 cacuggugug acuccucgcc cugcaagaac ggcggcaaau gcuggcagac ccacacccag    3240
uaccgcugcg agugccccag cggcuggacc ggccuuuacu gcgacgugcc cagcgugucc    3300
ugugaggugg cugcgcagcg acaaggguguu gacguugccc gccugugcca gcauggaggg    3360
cucugugugu acgcgggcaa cacgcaccac ugccgcugcc aggcgggcua cacaggcagc    3420
uacugugagg accuggugga cgagugcuca cccagcccu gccagaacgg ggccaccugc    3480
acggacuacc ugggcggcua ucccugcaag ugcguggccg cuaccacgg ggugaacugc    3540 ucugaggaga ucgacgagug ccucucccac cccugccaga acggggcac cugccucgac    3600 cuccccaaca ccuacaagug cuccugccca cggggcacuc agggugugca cugugagauc    3660
aacguggacg acugcaauc ccccguugac cccgugucc ggagccccaa gugcuuuaac    3720
aacggcaccu gcguggacca ggugggcggg uacagcugca ccugcccgcc gggcuucgug    3780
ggugagcgcu gugagggga ugucaacgag ugccugucca auccugcga cgcccgugc    3840 acccagaacu gcgugcagcg cgucaaugac uuccacugcg agugccgugc uggcacacc    3900 gggcgccgcu gcgaguccgu caucaauggc ugcaaaggca gcccugcaa gaaugggggc    3960 accugcgccg uggccuccaa caccgcccgc ggguucaucu gcaagugccc ugcgggcuuc    4020
gagggcgcca cgugugagaa ugacgcucgu accgcggca gccugcgcug ccucaacggc    4080
ggcacaugca ucuccggccc gcgcagcccc accugccugu gccugggccc cuucacgggc    4140
cccgaaugcc aguucccggc cagcagcccc ugccuggggcg gcaaccccug cuacaaccag    4200
gggaccugug agcccacauc cgagagcccc uucuaccguu gccugugccc cgccaaauuc    4260
aacgggcucu ugugccacau ccuggacuac agcuucgggg guggggccgg gcgcgacauc    4320 ccccccgccgc ugaucgagga ggcgugcgag cugcccgagu gccaggagga cgcgggcaac    4380
aaggucugca gccugcagug caacaaccac gcgugcggcu gggacggcgg ugacugcucc    4440
cucaacuuca augaccccug gaagaacugc acgcagucuc ugcagugcug gaaguacuuc    4500
agugacggcc acugugacag ccagugcaac ucagccggcu gccucuucga cggcuuugac    4560
ugccagcgug cggaaggcca gugcaacccc cuguacgacc aguacugcaa ggaccacuuc    4620
agcgacgggc acugcgacca gggcugcaac agcgcgagu gcgaguggga cgggcuggac    4680
ugugcggagc auguacccga gaggcuggcg gccggcacgc uggugguggu ggcugaug    4740 ccgccggagc agcugcgcaa cagcccuuc cacuuccugc gggagcucag ccgcgugcug    4800
cacaccaacg uggucuucaa gcgugacgca cacggccagc agaugaucuu ccccuacuac    4860
ggccgcgagg aggagcugcg caagcacccc aucaagcgug ccgccgaggg cuggccgca    4920 ccugacgccc ugcugggcca ggugaaggcc ucgcugcucc cugguggcag cgaggguggg    4980
cggcggcgga gggagcugga ccccauggac gucgccgcu ccaucgucua ccuggagauu    5040
gacaaccggc agugugugca ggccuccucg cagugcuucc agagccac cgacguggcc    5100 gcauuccugg gagcgcucgc cucgcugggc agccucaaca uccccuacaa gaucgaggcc    5160
```

```
gugcagagug agaccgugga gccgccccg ccggcgcagc ugcacuucau guacguggcg    5220
gcggccgccu uugugcuucu guucuucgug ggcugcgggg ugcugcuguc ccgcaagcgc    5280
cggcggcagc auggccagcu cugguuccu gagggcuuca aagugucuga ggccagcaag    5340
aagaagcggc gggagcccu cggcgaggac uccgugggcc ucaagcccu gaagaacgcu     5400 ucagacggug cccucaugga cgacaaccag aaugaguggg gggacgagga ccuggagacc    5460
aagaaguucc gguucgagga gcccgugguu cugccgacca uggacgacca gacagaccac    5520
cggcagugga cucagcagca ccuggaugcc gcugaccugc gcaugucugc cauggccccc    5580
acaccgcccc agggugaggu ugacgccgac ugcauggacg ucaauguccg cgggccugau    5640
ggcuucaccc cgcucaugau cgccuccugc agcggggcg gccuggagac gggcaacagc    5700
gaggaagagg aggacgcgcc ggccgucauc uccgacuuca cuaccaggg cgccagccug    5760 cacaaccaga cagaccgcac gggcgagacc gccuugcacc uggccgcccg cuacucacgc    5820
ucugaugccg ccaagcgccu gcuggaggcc agcgcagaug ccaacaucca ggacaacaug    5880
ggccgcaccc cgcugcaugc ggcugugucu gccgacgcac aaggugucuu ccagauccug    5940
auccggaacc gagccacaga ccuggaugcc cgcaugcaug auggcacgac gccacugauc    6000
cuggcugccc gccuggccgu ggagggcaug cuggaggacc ucaucaacuc acacgccgac    6060
gucaacgccg uagaugaccu gggcaagucc gcccugcacu gggccgccgc cgugaacaau    6120
guggaugccg caguugugcu ccugaagaac ggggcuaaca aagauaugca gaacaacagg    6180
gaggagacac cccuguuucu ggccgcccgg gagggcagcu acgagaccgc caaggugcug    6240
cuggaccacu uugccaaccg ggacaucacg gaucauaugg accgccugcc gcgcgacauc    6300
gcacaggagc gcaugcauca cgacaucgug aggcugcugg acgaguacaa ccuggugcgc    6360
agcccgcagc ugcacggagc cccgcugggg ggcacgccca cccugucgcc cccgcucugc    6420
ucgcccaacg gcuaccuggg cagccucaag cccggcgugc agggcaagaa gguccgcaag    6480
cccagcagca aaggccuggc cuguggaagc aaggaggcca aggaccucaa ggcacggagg    6540 aagaagucc aggacggcaa gggcugccug cuggacagcu ccggcaugcu cucgcccgug    6600
gacucccugg agucacccca uggcuaccug ucagacgugg ccgccgcc acugcugccc    6660 uccccguucc agcagucucc guccgugccc cucaaccacc ugccugggau gcccgacacc    6720
caccuggcca ucgggcaccu gaacuggcg gccaagcccg agauggcggc cgggugggg    6780 ggcggccggc uggccuuuga cacuggccca ccucgucucu cccaccugcc uguggccucu    6840
ggcaccagca ccguccuggg cuccagcagc ggagggcc ugaauuucac uggggcggg      6900 uccaccaguu ugaauggca augcgagugg cuguccggc ugcagagcgg cauggugccg     6960
aaccaauaca ccccucugcg ggggagugug gcaccaggcc cccugagcac acaggccccc    7020
ucccugcagc auggcauggu aggcccgcug cacaguagcc uugcugccag cgcccugucc    7080
cagaugauga gcuaccaggg ccugcccagc acccggcugg ccaccagcc ucaccuggug    7140 cagacccagc aggugcagcc acaaaacuua cagaugcagc agcagaaccu gcagccagca    7200
aacauccagc agcagcaaag ccugcagccg ccaccaccac caccacagcc gcaccuggc    7260 gugagcucag cagccagcgg ccaccugggc cggagcuucc ugaguggaga gccgagccag    7320 gcagacguc agccacuggg ccccagcagc cugccggugc acacuauucu gccccaggag    7380
agccccgccc ugcccacguc gcugccaucc ucgcuggucc cacccgugac cgcagcccag    7440
uuccugacgc ccccccgca gcacagcuac ccucgccug uggacaacac cccagcccac    7500
cagcuacagg ugccugagca ccccuuccuc accccgcucc cugaguccc ugaccagugg    7560
```

```
uccagcucgu ccccgcauuc caacgucucc gacugguccg agggcgucuc cagcccuccc    7620
accagcaugc agucccagau cgcccgcauu ccggaggccu ucaaguaaac ggcgcgcccc    7680
acgagacccc ggcuuccuuu cccaagccuu cgggcgucug ugugcgcucu guggaugcca    7740
gggccgacca gaggagccuu uuaaaaacac auguuuuuau acaaauaag aacgaggauu     7800 uuaauuuuuu uuaguauuua uuuauguacu uuuauuuuac acagaaacac ugccuuuuua    7860
uuuauaugua cuguuuuauc uggccccagg uagaaacuuu uaucuauucu gagaaaacaa    7920
gcaaguucug agagccaggg uuuuccuacg uaggaugaaa agauucuucu guguuuauaa    7980
aauauaaaca aagauucaug auuuauaaau gccauuauu uauugauucc uuuuucaaa      8040 auccaaaaag aaaugauguu ggagaaggga aguugaacga gcauagucca aaaagcuccu    8100
ggggcgucca ggccgcgccc uuccccgac gcccacccaa ccccaagcca gcccggccgc     8160
uccaccagca ucaccugccu guuaggagaa gcugcaucca gaggcaaacg gaggcaaagc    8220
uggcucaccu uccgcacgcg gauuaauuug caucugaaau aggaaacaag ugaaagcaua    8280
uggguuagau guugccaugu guuuuagaug guuucuugca agcaugcuug ugaaaaugug    8340
uucucggagu guguaugcca agagugcacc cauggauacca aucaugaauc uuuguuucag   8400
guucaguauu auguaguugu ucguugguua uacaaguucu ugguccuucc agaaccaccc    8460
cggcccccug cccguucuug aaauguaggc aucaugcaug ucaaacauga gaugugugga   8520
cuguggcacu ugccuggguc acacacggag gcauccuacc cuuuucuggg gaaagacacu    8580
gccugggcug accccggugg cggccccagc accuagccu gcacaguguc ccccagguuc     8640
cgaagaagau gcuccagcaa cacagccugg gccccagcuc gcgggacccg accccccgug    8700
ggcucccgug uuuuguagga gacuugccag agccgggcac auugagcugu gcaacgccgu    8760
gggcugcguc cuuugguccu guccccgcag cccuggcagg gggcaugcgg ucgggcaggg    8820
gcuggaggga ggcgggggcu gcccuugggc caccccuccu aguuugggag gagcagauuu    8880
uugcaauacc aaguauagcc uauggcagaa aaaaugcucu g uaaauauguu uuuaaaggug   8940
gauuuuguuu aaaaaaucuu aaugaauag ucuguugugu gucaugccag ugagggacgu    9000
cagacuuggc ucagcucggg gagccuuagc cgcccaugca cuggggacgc uccgcugccg    9060
ugccgccugc acuccucagg gcagccuccc ccggcucuac gggggccgcg uggugccauc    9120 cccaggggc auguaccagau gcgucccaag auguugauuu uuacuguguu uuauaaaaua    9180
gaguguaguu uacagaaaaa gacuuuaaaa gugaucuaca ugaggaacug uagaugaugu    9240
auuuuuuuca ucuuuuugu uaacugauuu gcaauaaaaa ugauacugau ggugaaaaaa    9300
aaaaaaaaa                                                             9309
```

<210> SEQ ID NO 13
<211> LENGTH: 17
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-F modified
<220> FEATURE:
<221> NAME/KEY: misc_feature
<222> LOCATION: (2)..(2)
<223> OTHER INFORMATION: Nucleotide is 2'-F modified
<220> FEATURE:
<221> NAME/KEY: misc_feature
<222> LOCATION: (3)..(3)

```
<223> OTHER INFORMATION: Nucleotide is 2'-O-methyl modified
<220> FEATURE:
<221> NAME/KEY: misc_feature
<222> LOCATION: (4)..(4)
<223> OTHER INFORMATION: Nucleotide is 2'-F modified
<220> FEATURE:
<221> NAME/KEY: misc_feature
<222> LOCATION: (5)..(5)
<223> OTHER INFORMATION: Nucleotide is 2'-O-methyl modified
<220> FEATURE:
<221> NAME/KEY: misc_feature
<222> LOCATION: (6)..(6)
<223> OTHER INFORMATION: Nucleotide is 2'-F modified
<220> FEATURE:
<221> NAME/KEY: misc_feature
<222> LOCATION: (7)..(7)
<223> OTHER INFORMATION: Nucleotide is 2'-O-methyl modified
<220> FEATURE:
<221> NAME/KEY: misc_feature
<222> LOCATION: (8)..(8)
<223> OTHER INFORMATION: Nucleotide is 2'-F modified
<220> FEATURE:
<221> NAME/KEY: misc_feature
<222> LOCATION: (9)..(9)
<223> OTHER INFORMATION: Nucleotide is 2'-O-methyl modified
<220> FEATURE:
<221> NAME/KEY: misc_feature
<222> LOCATION: (10)..(10)
<223> OTHER INFORMATION: Nucleotide is 2'-F modified
<220> FEATURE:
<221> NAME/KEY: misc_feature
<222> LOCATION: (11)..(11)
<223> OTHER INFORMATION: Nucleotide is 2'-O-methyl modified
<220> FEATURE:
<221> NAME/KEY: misc_feature
<222> LOCATION: (12)..(12)
<223> OTHER INFORMATION: Nucleotide is 2'-F modified
<220> FEATURE:
<221> NAME/KEY: misc_feature
<222> LOCATION: (13)..(13)
<223> OTHER INFORMATION: Nucleotide is 2'-O-methyl modified
<220> FEATURE:
<221> NAME/KEY: misc_feature
<222> LOCATION: (14)..(14)
<223> OTHER INFORMATION: Nucleotide is 2'-F modified
<220> FEATURE:
<221> NAME/KEY: misc_feature
<222> LOCATION: (15)..(15)
<223> OTHER INFORMATION: Nucleotide is 2'-O-methyl  modified
<220> FEATURE:
<221> NAME/KEY: misc_feature
<222> LOCATION: (16)..(16)
<223> OTHER INFORMATION: Nucleotide is 2'-F modified
<220> FEATURE:
<221> NAME/KEY: misc_feature
<222> LOCATION: (17)..(17)
<223> OTHER INFORMATION: Nucleotide is 2'-O-methyl modified

<400> SEQUENCE: 13
cgagcuggac cacuggu                                                    17

<210> SEQ ID NO 14
<211> LENGTH: 17
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-O-methyl modified
<220> FEATURE:
<221> NAME/KEY: misc_feature
<222> LOCATION: (2)..(2)
<223> OTHER INFORMATION: Nucleotide is 2'-O-methyl modified
<220> FEATURE:
<221> NAME/KEY: misc_feature
```

```
<222> LOCATION: (3)..(3)
<223> OTHER INFORMATION: Nucleotide is 2'-F modified
<220> FEATURE:
<221> NAME/KEY: misc_feature
<222> LOCATION: (4)..(4)
<223> OTHER INFORMATION: Nucleotide is 2'-O-methyl modified
<220> FEATURE:
<221> NAME/KEY: misc_feature
<222> LOCATION: (5)..(5)
<223> OTHER INFORMATION: Nucleotide is 2'-F modified
<220> FEATURE:
<221> NAME/KEY: misc_feature
<222> LOCATION: (6)..(6)
<223> OTHER INFORMATION: Nucleotide is 2'-O-methyl  modified
<220> FEATURE:
<221> NAME/KEY: misc_feature
<222> LOCATION: (7)..(7)
<223> OTHER INFORMATION: Nucleotide is 2'-F modified
<220> FEATURE:
<221> NAME/KEY: misc_feature
<222> LOCATION: (8)..(8)
<223> OTHER INFORMATION: Nucleotide is 2'-O-methyl modified
<220> FEATURE:
<221> NAME/KEY: misc_feature
<222> LOCATION: (9)..(9)
<223> OTHER INFORMATION: Nucleotide is 2'-F modified
<220> FEATURE:
<221> NAME/KEY: misc_feature
<222> LOCATION: (10)..(10)
<223> OTHER INFORMATION: Nucleotide is 2'-O-methyl modified
<220> FEATURE:
<221> NAME/KEY: misc_feature
<222> LOCATION: (11)..(11)
<223> OTHER INFORMATION: Nucleotide is 2'-F modified
<220> FEATURE:
<221> NAME/KEY: misc_feature
<222> LOCATION: (12)..(12)
<223> OTHER INFORMATION: Nucleotide is 2'-O-methyl modified
<220> FEATURE:
<221> NAME/KEY: misc_feature
<222> LOCATION: (13)..(13)
<223> OTHER INFORMATION: Nucleotide is 2'-F modified
<220> FEATURE:
<221> NAME/KEY: misc_feature
<222> LOCATION: (14)..(14)
<223> OTHER INFORMATION: Nucleotide is 2'-O-methyl modified
<220> FEATURE:
<221> NAME/KEY: misc_feature
<222> LOCATION: (15)..(15)
<223> OTHER INFORMATION: Nucleotide is 2'-F modified
<220> FEATURE:
<221> NAME/KEY: misc_feature
<222> LOCATION: (16)..(16)
<223> OTHER INFORMATION: Nucleotide is 2'-O-methyl modified
<220> FEATURE:
<221> NAME/KEY: misc_feature
<222> LOCATION: (17)..(17)
<223> OTHER INFORMATION: Nucleotide is 2'-F modified

<400> SEQUENCE: 14
accagugguc cagcucg                                                17

<210> SEQ ID NO 15
<211> LENGTH: 21
<212> TYPE: DNA
<213> ORGANISM: Artificial
<220> FEATURE:
<223> OTHER INFORMATION: Synthetic

<400> SEQUENCE: 15
gcgcucgccg cacgaggcct t                                           21

<210> SEQ ID NO 16
<211> LENGTH: 21
<212> TYPE: DNA
```

```
<213> ORGANISM: Artificial
<220> FEATURE:
<223> OTHER INFORMATION: Synthetic

<400> SEQUENCE: 16
ggccucgugc ggcgagcgct t                                              21

<210> SEQ ID NO 17
<211> LENGTH: 21
<212> TYPE: DNA
<213> ORGANISM: Artificial
<220> FEATURE:
<223> OTHER INFORMATION: Synthetic

<400> SEQUENCE: 17
cuucgugggc ccgcgaugct t                                              21

<210> SEQ ID NO 18
<211> LENGTH: 21
<212> TYPE: DNA
<213> ORGANISM: Artificial
<220> FEATURE:
<223> OTHER INFORMATION: Synthetic

<400> SEQUENCE: 18
gcaucgcggg cccacgaagt t                                              21

<210> SEQ ID NO 19
<211> LENGTH: 21
<212> TYPE: DNA
<213> ORGANISM: Artificial
<220> FEATURE:
<223> OTHER INFORMATION: Synthetic

<400> SEQUENCE: 19
aagaacgccg ggacaugcct t                                              21

<210> SEQ ID NO 20
<211> LENGTH: 21
<212> TYPE: DNA
<213> ORGANISM: Artificial
<220> FEATURE:
<223> OTHER INFORMATION: Synthetic

<400> SEQUENCE: 20
ggcauguccc ggcguucuut t                                              21

<210> SEQ ID NO 21
<211> LENGTH: 21
<212> TYPE: DNA
<213> ORGANISM: Artificial
<220> FEATURE:
<223> OTHER INFORMATION: Synthetic

<400> SEQUENCE: 21
caugccacgu gguggaccgt t                                              21

<210> SEQ ID NO 22
<211> LENGTH: 21
<212> TYPE: DNA
<213> ORGANISM: Artificial
<220> FEATURE:
<223> OTHER INFORMATION: Synthetic

<400> SEQUENCE: 22
cgguccacca cguggcaugt t                                              21
```

<210> SEQ ID NO 23
<211> LENGTH: 21
<212> TYPE: DNA
<213> ORGANISM: Artificial
<220> FEATURE:
<223> OTHER INFORMATION: Synthetic

<400> SEQUENCE: 23
cggaguacaa gugccgcugt t                                              21

<210> SEQ ID NO 24
<211> LENGTH: 21
<212> TYPE: DNA
<213> ORGANISM: Artificial
<220> FEATURE:
<223> OTHER INFORMATION: Synthetic

<400> SEQUENCE: 24
cagcggcacu uguacuccgt t                                              21

<210> SEQ ID NO 25
<211> LENGTH: 21
<212> TYPE: DNA
<213> ORGANISM: Artificial
<220> FEATURE:
<223> OTHER INFORMATION: Synthetic

<400> SEQUENCE: 25
ugccggcagg augucaacgt t                                              21

<210> SEQ ID NO 26
<211> LENGTH: 21
<212> TYPE: DNA
<213> ORGANISM: Artificial
<220> FEATURE:
<223> OTHER INFORMATION: Synthetic

<400> SEQUENCE: 26
cguugacauc cugccggcat t                                              21

<210> SEQ ID NO 27
<211> LENGTH: 21
<212> TYPE: DNA
<213> ORGANISM: Artificial
<220> FEATURE:
<223> OTHER INFORMATION: Synthetic

<400> SEQUENCE: 27
gagggugugc acugcgaggt t                                              21

<210> SEQ ID NO 28
<211> LENGTH: 21
<212> TYPE: DNA
<213> ORGANISM: Artificial
<220> FEATURE:
<223> OTHER INFORMATION: Synthetic

<400> SEQUENCE: 28
ccucgcagug cacacccuct t                                              21

<210> SEQ ID NO 29
<211> LENGTH: 21
<212> TYPE: DNA
<213> ORGANISM: Artificial
<220> FEATURE:

```
<223> OTHER INFORMATION: Synthetic

<400> SEQUENCE: 29
ggacccaaca cuuacaccut t                                              21

<210> SEQ ID NO 30
<211> LENGTH: 21
<212> TYPE: DNA
<213> ORGANISM: Artificial
<220> FEATURE:
<223> OTHER INFORMATION: Synthetic

<400> SEQUENCE: 30
agguguaagu guugggucct t                                              21

<210> SEQ ID NO 31
<211> LENGTH: 21
<212> TYPE: DNA
<213> ORGANISM: Artificial
<220> FEATURE:
<223> OTHER INFORMATION: Synthetic

<400> SEQUENCE: 31
cugcaaggac ggcgucgcct t                                              21

<210> SEQ ID NO 32
<211> LENGTH: 21
<212> TYPE: DNA
<213> ORGANISM: Artificial
<220> FEATURE:
<223> OTHER INFORMATION: Synthetic

<400> SEQUENCE: 32
ggcgacgccg uccuugcagt t                                              21

<210> SEQ ID NO 33
<211> LENGTH: 21
<212> TYPE: DNA
<213> ORGANISM: Artificial
<220> FEATURE:
<223> OTHER INFORMATION: Synthetic

<400> SEQUENCE: 33
gcacguguau ugacgacgut t                                              21

<210> SEQ ID NO 34
<211> LENGTH: 21
<212> TYPE: DNA
<213> ORGANISM: Artificial
<220> FEATURE:
<223> OTHER INFORMATION: Synthetic

<400> SEQUENCE: 34
acgucgucaa uacacgugct t                                              21

<210> SEQ ID NO 35
<211> LENGTH: 21
<212> TYPE: DNA
<213> ORGANISM: Artificial
<220> FEATURE:
<223> OTHER INFORMATION: Synthetic

<400> SEQUENCE: 35
cacguguauu gacgacguut t                                              21
```

<210> SEQ ID NO 36
<211> LENGTH: 21
<212> TYPE: DNA
<213> ORGANISM: Artificial
<220> FEATURE:
<223> OTHER INFORMATION: Synthetic

<400> SEQUENCE: 36
aacgucguca auacacgugt t                                          21

<210> SEQ ID NO 37
<211> LENGTH: 21
<212> TYPE: DNA
<213> ORGANISM: Artificial
<220> FEATURE:
<223> OTHER INFORMATION: Synthetic

<400> SEQUENCE: 37
acguguauug acgacguugt t                                          21

<210> SEQ ID NO 38
<211> LENGTH: 21
<212> TYPE: DNA
<213> ORGANISM: Artificial
<220> FEATURE:
<223> OTHER INFORMATION: Synthetic

<400> SEQUENCE: 38
caacgucguc aauacacgut t                                          21

<210> SEQ ID NO 39
<211> LENGTH: 21
<212> TYPE: DNA
<213> ORGANISM: Artificial
<220> FEATURE:
<223> OTHER INFORMATION: Synthetic

<400> SEQUENCE: 39
ggacgagugc ucacccagct t                                          21

<210> SEQ ID NO 40
<211> LENGTH: 21
<212> TYPE: DNA
<213> ORGANISM: Artificial
<220> FEATURE:
<223> OTHER INFORMATION: Synthetic

<400> SEQUENCE: 40
gcugggugag cacucgucct t                                          21

<210> SEQ ID NO 41
<211> LENGTH: 21
<212> TYPE: DNA
<213> ORGANISM: Artificial
<220> FEATURE:
<223> OTHER INFORMATION: Synthetic

<400> SEQUENCE: 41
ccaucaagcg ugccgccgat t                                          21

<210> SEQ ID NO 42
<211> LENGTH: 21
<212> TYPE: DNA
<213> ORGANISM: Artificial
<220> FEATURE:
<223> OTHER INFORMATION: Synthetic

<400> SEQUENCE: 42
ucggcggcac gcuugauggt t          21

<210> SEQ ID NO 43
<211> LENGTH: 21
<212> TYPE: DNA
<213> ORGANISM: Artificial
<220> FEATURE:
<223> OTHER INFORMATION: Synthetic

<400> SEQUENCE: 43
ccgguucgag gagcccgugt t          21

<210> SEQ ID NO 44
<211> LENGTH: 21
<212> TYPE: DNA
<213> ORGANISM: Artificial
<220> FEATURE:
<223> OTHER INFORMATION: Synthetic

<400> SEQUENCE: 44
cacgggcucc ucgaaccggt t          21

<210> SEQ ID NO 45
<211> LENGTH: 21
<212> TYPE: DNA
<213> ORGANISM: Artificial
<220> FEATURE:
<223> OTHER INFORMATION: Synthetic

<400> SEQUENCE: 45
ccgggacauc acggaucaut t          21

<210> SEQ ID NO 46
<211> LENGTH: 21
<212> TYPE: DNA
<213> ORGANISM: Artificial
<220> FEATURE:
<223> OTHER INFORMATION: Synthetic

<400> SEQUENCE: 46
augauccgug augcccggt t          21

<210> SEQ ID NO 47
<211> LENGTH: 21
<212> TYPE: DNA
<213> ORGANISM: Artificial
<220> FEATURE:
<223> OTHER INFORMATION: Synthetic

<400> SEQUENCE: 47
gacaucgcac aggagcgcat t          21

<210> SEQ ID NO 48
<211> LENGTH: 21
<212> TYPE: DNA
<213> ORGANISM: Artificial
<220> FEATURE:
<223> OTHER INFORMATION: Synthetic

<400> SEQUENCE: 48
ugcgcuccug ugcgauguct t          21

<210> SEQ ID NO 49
<211> LENGTH: 21

```
<212> TYPE: DNA
<213> ORGANISM: Artificial
<220> FEATURE:
<223> OTHER INFORMATION: Synthetic

<400> SEQUENCE: 49
cagagcggca uggugccgat t                                              21

<210> SEQ ID NO 50
<211> LENGTH: 21
<212> TYPE: DNA
<213> ORGANISM: Artificial
<220> FEATURE:
<223> OTHER INFORMATION: Synthetic

<400> SEQUENCE: 50
ucggcaccau gccgcucugt t                                              21

<210> SEQ ID NO 51
<211> LENGTH: 21
<212> TYPE: DNA
<213> ORGANISM: Artificial
<220> FEATURE:
<223> OTHER INFORMATION: Synthetic

<400> SEQUENCE: 51
cauggugccg aaccaauact t                                              21

<210> SEQ ID NO 52
<211> LENGTH: 21
<212> TYPE: DNA
<213> ORGANISM: Artificial
<220> FEATURE:
<223> OTHER INFORMATION: Synthetic

<400> SEQUENCE: 52
guauugguuc ggcaccaugt t                                              21

<210> SEQ ID NO 53
<211> LENGTH: 21
<212> TYPE: DNA
<213> ORGANISM: Artificial
<220> FEATURE:
<223> OTHER INFORMATION: Synthetic

<400> SEQUENCE: 53
uggugccgaa ccaauacaat t                                              21

<210> SEQ ID NO 54
<211> LENGTH: 21
<212> TYPE: DNA
<213> ORGANISM: Artificial
<220> FEATURE:
<223> OTHER INFORMATION: Synthetic

<400> SEQUENCE: 54
uuguauuggu ucggcaccat t                                              21

<210> SEQ ID NO 55
<211> LENGTH: 21
<212> TYPE: DNA
<213> ORGANISM: Artificial
<220> FEATURE:
<223> OTHER INFORMATION: Synthetic

<400> SEQUENCE: 55
```

```
cucgccugug gacaacacct t                                              21

<210> SEQ ID NO 56
<211> LENGTH: 21
<212> TYPE: DNA
<213> ORGANISM: Artificial
<220> FEATURE:
<223> OTHER INFORMATION: Synthetic

<400> SEQUENCE: 56
gguguugucc acaggcgagt t                                              21

<210> SEQ ID NO 57
<211> LENGTH: 21
<212> TYPE: DNA
<213> ORGANISM: Artificial
<220> FEATURE:
<223> OTHER INFORMATION: Synthetic

<400> SEQUENCE: 57
gaccaguggu ccagcucgut t                                              21

<210> SEQ ID NO 58
<211> LENGTH: 21
<212> TYPE: DNA
<213> ORGANISM: Artificial
<220> FEATURE:
<223> OTHER INFORMATION: Synthetic

<400> SEQUENCE: 58
acgagcugga ccacugguct t                                              21

<210> SEQ ID NO 59
<211> LENGTH: 21
<212> TYPE: DNA
<213> ORGANISM: Artificial
<220> FEATURE:
<223> OTHER INFORMATION: Synthetic

<400> SEQUENCE: 59
cauuccaacg ucuccgacut t                                              21

<210> SEQ ID NO 60
<211> LENGTH: 21
<212> TYPE: DNA
<213> ORGANISM: Artificial
<220> FEATURE:
<223> OTHER INFORMATION: Synthetic

<400> SEQUENCE: 60
agucggagac guuggaaugt t                                              21

<210> SEQ ID NO 61
<211> LENGTH: 21
<212> TYPE: DNA
<213> ORGANISM: Artificial
<220> FEATURE:
<223> OTHER INFORMATION: Synthetic

<400> SEQUENCE: 61
auuccaacgu cuccgacugt t                                              21

<210> SEQ ID NO 62
<211> LENGTH: 21
<212> TYPE: DNA
<213> ORGANISM: Artificial
```

```
<220> FEATURE:
<223> OTHER INFORMATION: Synthetic

<400> SEQUENCE: 62
cagucggaga cguuggaaut t                                              21

<210> SEQ ID NO 63
<211> LENGTH: 21
<212> TYPE: DNA
<213> ORGANISM: Artificial
<220> FEATURE:
<223> OTHER INFORMATION: Synthetic

<400> SEQUENCE: 63
uuccaacguc uccgacuggt t                                              21

<210> SEQ ID NO 64
<211> LENGTH: 21
<212> TYPE: DNA
<213> ORGANISM: Artificial
<220> FEATURE:
<223> OTHER INFORMATION: Synthetic

<400> SEQUENCE: 64
ccagucggag acguuggaat t                                              21

<210> SEQ ID NO 65
<211> LENGTH: 21
<212> TYPE: DNA
<213> ORGANISM: Artificial
<220> FEATURE:
<223> OTHER INFORMATION: Synthetic

<400> SEQUENCE: 65
caacgucucc gacuggucct t                                              21

<210> SEQ ID NO 66
<211> LENGTH: 21
<212> TYPE: DNA
<213> ORGANISM: Artificial
<220> FEATURE:
<223> OTHER INFORMATION: Synthetic

<400> SEQUENCE: 66
ggaccagucg gagacguugt t                                              21

<210> SEQ ID NO 67
<211> LENGTH: 21
<212> TYPE: DNA
<213> ORGANISM: Artificial
<220> FEATURE:
<223> OTHER INFORMATION: Synthetic

<400> SEQUENCE: 67
acgucuccga cugguccgat t                                              21

<210> SEQ ID NO 68
<211> LENGTH: 21
<212> TYPE: DNA
<213> ORGANISM: Artificial
<220> FEATURE:
<223> OTHER INFORMATION: Synthetic

<400> SEQUENCE: 68
ucggaccagu cggagacgut t                                              21
```

```
<210> SEQ ID NO 69
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-F modified
<220> FEATURE:
<221> NAME/KEY: misc_feature
<222> LOCATION: (2)..(2)
<223> OTHER INFORMATION: Nucleotide is 2'-F modified
<220> FEATURE:
<221> NAME/KEY: misc_feature
<222> LOCATION: (3)..(3)
<223> OTHER INFORMATION: Nucleotide is 2'-O-methyl modified
<220> FEATURE:
<221> NAME/KEY: misc_feature
<222> LOCATION: (4)..(4)
<223> OTHER INFORMATION: Nucleotide is 2'-F modified
<220> FEATURE:
<221> NAME/KEY: misc_feature
<222> LOCATION: (5)..(5)
<223> OTHER INFORMATION: Nucleotide is 2'-O-methyl modified
<220> FEATURE:
<221> NAME/KEY: misc_feature
<222> LOCATION: (6)..(6)
<223> OTHER INFORMATION: Nucleotide is 2'-F modified
<220> FEATURE:
<221> NAME/KEY: misc_feature
<222> LOCATION: (7)..(7)
<223> OTHER INFORMATION: Nucleotide is 2'-O-methyl modified
<220> FEATURE:
<221> NAME/KEY: misc_feature
<222> LOCATION: (8)..(8)
<223> OTHER INFORMATION: Nucleotide is 2'-F modified
<220> FEATURE:
<221> NAME/KEY: misc_feature
<222> LOCATION: (9)..(9)
<223> OTHER INFORMATION: Nucleotide is 2'-O-methyl modified
<220> FEATURE:
<221> NAME/KEY: misc_feature
<222> LOCATION: (10)..(10)
<223> OTHER INFORMATION: Nucleotide is 2'-F modified
<220> FEATURE:
<221> NAME/KEY: misc_feature
<222> LOCATION: (11)..(11)
<223> OTHER INFORMATION: Nucleotide is 2'-O-methyl modified
<220> FEATURE:
<221> NAME/KEY: misc_feature
<222> LOCATION: (12)..(12)
<223> OTHER INFORMATION: Nucleotide is 2'-F modified
<220> FEATURE:
<221> NAME/KEY: misc_feature
<222> LOCATION: (13)..(13)
<223> OTHER INFORMATION: Nucleotide is 2'-O-methyl modified
<220> FEATURE:
<221> NAME/KEY: misc_feature
<222> LOCATION: (14)..(14)
<223> OTHER INFORMATION: Nucleotide is 2'-F modified
<220> FEATURE:
<221> NAME/KEY: misc_feature
<222> LOCATION: (15)..(15)
<223> OTHER INFORMATION: Nucleotide is 2'-O-methyl modified
<220> FEATURE:
<221> NAME/KEY: misc_feature
<222> LOCATION: (16)..(16)
<223> OTHER INFORMATION: Nucleotide is 2'-F modified
<220> FEATURE:
<221> NAME/KEY: misc_feature
<222> LOCATION: (17)..(17)
<223> OTHER INFORMATION: Nucleotide is 2'-O-methyl modified
<220> FEATURE:
<221> NAME/KEY: misc_feature
<222> LOCATION: (18)..(18)
<223> OTHER INFORMATION: Nucleotide is 2'-F modified
```

```
<220> FEATURE:
<221> NAME/KEY: misc_feature
<222> LOCATION: (19)..(19)
<223> OTHER INFORMATION: Nucleotide is 2'-O-methyl modified
<220> FEATURE:
<221> NAME/KEY: misc_feature
<222> LOCATION: (20)..(21)
<223> OTHER INFORMATION: nucleotides linked by phosphothioate

<400> SEQUENCE: 69
acgagcugga ccacuggucu t                                              21

<210> SEQ ID NO 70
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-O-methyl modified
<220> FEATURE:
<221> NAME/KEY: misc_feature
<222> LOCATION: (2)..(2)
<223> OTHER INFORMATION: Nucleotide is 2'-O-methyl modified
<220> FEATURE:
<221> NAME/KEY: misc_feature
<222> LOCATION: (3)..(3)
<223> OTHER INFORMATION: Nucleotide is 2'-F methyl modified
<220> FEATURE:
<221> NAME/KEY: misc_feature
<222> LOCATION: (4)..(4)
<223> OTHER INFORMATION: Nucleotide is 2'-O-methyl modified
<220> FEATURE:
<221> NAME/KEY: misc_feature
<222> LOCATION: (5)..(5)
<223> OTHER INFORMATION: Nucleotide is 2'-F methyl modified
<220> FEATURE:
<221> NAME/KEY: misc_feature
<222> LOCATION: (6)..(6)
<223> OTHER INFORMATION: Nucleotide is 2'-O-methyl modified
<220> FEATURE:
<221> NAME/KEY: misc_feature
<222> LOCATION: (7)..(7)
<223> OTHER INFORMATION: Nucleotide is 2'-F methyl modified
<220> FEATURE:
<221> NAME/KEY: misc_feature
<222> LOCATION: (8)..(8)
<223> OTHER INFORMATION: Nucleotide is 2'-O-methyl modified
<220> FEATURE:
<221> NAME/KEY: misc_feature
<222> LOCATION: (9)..(9)
<223> OTHER INFORMATION: Nucleotide is 2'-Fmethyl modified
<220> FEATURE:
<221> NAME/KEY: misc_feature
<222> LOCATION: (10)..(10)
<223> OTHER INFORMATION: Nucleotide is 2'-O-methyl modified
<220> FEATURE:
<221> NAME/KEY: misc_feature
<222> LOCATION: (11)..(11)
<223> OTHER INFORMATION: Nucleotide is 2'-F methyl modified
<220> FEATURE:
<221> NAME/KEY: misc_feature
<222> LOCATION: (12)..(12)
<223> OTHER INFORMATION: Nucleotide is 2'-O-methyl modified
<220> FEATURE:
<221> NAME/KEY: misc_feature
<222> LOCATION: (13)..(13)
<223> OTHER INFORMATION: Nucleotide is 2'-F methyl modified
<220> FEATURE:
<221> NAME/KEY: misc_feature
<222> LOCATION: (14)..(14)
<223> OTHER INFORMATION: Nucleotide is 2'-O-methyl modified
<220> FEATURE:
<221> NAME/KEY: misc_feature
<222> LOCATION: (15)..(15)
```

-continued

```
<223> OTHER INFORMATION: Nucleotide is 2'-F methyl modified
<220> FEATURE:
<221> NAME/KEY: misc_feature
<222> LOCATION: (16)..(16)
<223> OTHER INFORMATION: Nucleotide is 2'-O-methyl modified
<220> FEATURE:
<221> NAME/KEY: misc_feature
<222> LOCATION: (17)..(17)
<223> OTHER INFORMATION: Nucleotide is 2'-F methyl modified
<220> FEATURE:
<221> NAME/KEY: misc_feature
<222> LOCATION: (18)..(18)
<223> OTHER INFORMATION: Nucleotide is 2'-O-methyl modified
<220> FEATURE:
<221> NAME/KEY: misc_feature
<222> LOCATION: (19)..(19)
<223> OTHER INFORMATION: Nucleotide is 2'-F methyl modified
<220> FEATURE:
<221> NAME/KEY: misc_feature
<222> LOCATION: (20)..(21)
<223> OTHER INFORMATION: Nucleotide linked by phosphothioate

<400> SEQUENCE: 70
gaccaguggu ccagcucgut t                                       21

<210> SEQ ID NO 71
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-F methyl modified
<220> FEATURE:
<221> NAME/KEY: misc_feature
<222> LOCATION: (2)..(2)
<223> OTHER INFORMATION: Nucleotide is 2'-F methyl modified
<220> FEATURE:
<221> NAME/KEY: misc_feature
<222> LOCATION: (3)..(3)
<223> OTHER INFORMATION: Nucleotide is 2'-O-methyl modified
<220> FEATURE:
<221> NAME/KEY: misc_feature
<222> LOCATION: (4)..(4)
<223> OTHER INFORMATION: Nucleotide is 2'-F methyl modified
<220> FEATURE:
<221> NAME/KEY: misc_feature
<222> LOCATION: (5)..(5)
<223> OTHER INFORMATION: Nucleotide is 2'-O-methyl modified
<220> FEATURE:
<221> NAME/KEY: misc_feature
<222> LOCATION: (6)..(6)
<223> OTHER INFORMATION: Nucleotide is 2'-F methyl modified
<220> FEATURE:
<221> NAME/KEY: misc_feature
<222> LOCATION: (7)..(7)
<223> OTHER INFORMATION: Nucleotide is 2'-O-methyl modified
<220> FEATURE:
<221> NAME/KEY: misc_feature
<222> LOCATION: (8)..(8)
<223> OTHER INFORMATION: Nucleotide is 2'-F methyl modified
<220> FEATURE:
<221> NAME/KEY: misc_feature
<222> LOCATION: (9)..(9)
<223> OTHER INFORMATION: Nucleotide is 2'-O-methyl modified
<220> FEATURE:
<221> NAME/KEY: misc_feature
<222> LOCATION: (10)..(10)
<223> OTHER INFORMATION: Nucleotide is 2'-F methyl modified
<220> FEATURE:
<221> NAME/KEY: misc_feature
<222> LOCATION: (11)..(11)
<223> OTHER INFORMATION: Nucleotide is 2'-O-methyl modified
<220> FEATURE:
<221> NAME/KEY: misc_feature
```

<222> LOCATION: (12)..(12)
<223> OTHER INFORMATION: Nucleotide is 2'-F methyl modified
<220> FEATURE:
<221> NAME/KEY: misc_feature
<222> LOCATION: (13)..(13)
<223> OTHER INFORMATION: Nucleotide is 2'-O-methyl modified
<220> FEATURE:
<221> NAME/KEY: misc_feature
<222> LOCATION: (14)..(14)
<223> OTHER INFORMATION: Nucleotide is 2'-F methyl modified
<220> FEATURE:
<221> NAME/KEY: misc_feature
<222> LOCATION: (15)..(15)
<223> OTHER INFORMATION: Nucleotide is 2'-O-methyl modified
<220> FEATURE:
<221> NAME/KEY: misc_feature
<222> LOCATION: (16)..(16)
<223> OTHER INFORMATION: Nucleotide is 2'-F methyl modified
<220> FEATURE:
<221> NAME/KEY: misc_feature
<222> LOCATION: (17)..(17)
<223> OTHER INFORMATION: Nucleotide is 2'-O-methyl modified
<220> FEATURE:
<221> NAME/KEY: misc_feature
<222> LOCATION: (18)..(18)
<223> OTHER INFORMATION: Nucleotide is 2'-F methyl modified
<220> FEATURE:
<221> NAME/KEY: misc_feature
<222> LOCATION: (19)..(19)
<223> OTHER INFORMATION: Nucleotide is 2'-O-methyl modified

<400> SEQUENCE: 71
cgagcuggac cacuggutt                                            19

<210> SEQ ID NO 72
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-O-methyl modified
<220> FEATURE:
<221> NAME/KEY: misc_feature
<222> LOCATION: (2)..(2)
<223> OTHER INFORMATION: Nucleotide is 2'-O-methyl modified
<220> FEATURE:
<221> NAME/KEY: misc_feature
<222> LOCATION: (3)..(3)
<223> OTHER INFORMATION: Nucleotide is 2'-F methyl modified
<220> FEATURE:
<221> NAME/KEY: misc_feature
<222> LOCATION: (4)..(4)
<223> OTHER INFORMATION: Nucleotide is 2'-O-methyl modified
<220> FEATURE:
<221> NAME/KEY: misc_feature
<222> LOCATION: (5)..(5)
<223> OTHER INFORMATION: Nucleotide is 2'-F methyl modified
<220> FEATURE:
<221> NAME/KEY: misc_feature
<222> LOCATION: (6)..(6)
<223> OTHER INFORMATION: Nucleotide is 2'-O-methyl modified
<220> FEATURE:
<221> NAME/KEY: misc_feature
<222> LOCATION: (7)..(7)
<223> OTHER INFORMATION: Nucleotide is 2'-F methyl modified
<220> FEATURE:
<221> NAME/KEY: misc_feature
<222> LOCATION: (8)..(8)
<223> OTHER INFORMATION: Nucleotide is 2'-O-methyl modified
<220> FEATURE:
<221> NAME/KEY: misc_feature
<222> LOCATION: (9)..(9)
<223> OTHER INFORMATION: Nucleotide is 2'-F methyl modified
<220> FEATURE:

<221> NAME/KEY: misc_feature
<222> LOCATION: (10)..(10)
<223> OTHER INFORMATION: Nucleotide is 2'-O-methyl modified
<220> FEATURE:
<221> NAME/KEY: misc_feature
<222> LOCATION: (11)..(11)
<223> OTHER INFORMATION: Nucleotide is 2'-F methyl modified
<220> FEATURE:
<221> NAME/KEY: misc_feature
<222> LOCATION: (12)..(12)
<223> OTHER INFORMATION: Nucleotide is 2'-O-methyl modified
<220> FEATURE:
<221> NAME/KEY: misc_feature
<222> LOCATION: (13)..(13)
<223> OTHER INFORMATION: Nucleotide is 2'-F methyl modified
<220> FEATURE:
<221> NAME/KEY: misc_feature
<222> LOCATION: (14)..(14)
<223> OTHER INFORMATION: Nucleotide is 2'-O-methyl modified
<220> FEATURE:
<221> NAME/KEY: misc_feature
<222> LOCATION: (15)..(15)
<223> OTHER INFORMATION: Nucleotide is 2'-F methyl modified
<220> FEATURE:
<221> NAME/KEY: misc_feature
<222> LOCATION: (16)..(16)
<223> OTHER INFORMATION: Nucleotide is 2'-F methyl modified
<220> FEATURE:
<221> NAME/KEY: misc_feature
<222> LOCATION: (17)..(17)
<223> OTHER INFORMATION: Nucleotide is 2'-F methyl modified
<220> FEATURE:
<221> NAME/KEY: misc_feature
<222> LOCATION: (18)..(19)
<223> OTHER INFORMATION: Nucleotides linked by phosphothioate
<220> FEATURE:
<221> NAME/KEY: misc_feature
<222> LOCATION: (18)..(18)
<223> OTHER INFORMATION: Nucleotide is 2'-O-methyl modified
<220> FEATURE:
<221> NAME/KEY: misc_feature
<222> LOCATION: (19)..(19)
<223> OTHER INFORMATION: Nucleotide is 2'-F methyl modified

<400> SEQUENCE: 72
accagugguc cagcucgtt                                              19

<210> SEQ ID NO 73
<211> LENGTH: 21
<212> TYPE: DNA
<213> ORGANISM: Artificial
<220> FEATURE:
<223> OTHER INFORMATION: Synthetic

<400> SEQUENCE: 73
gcgcucgccg cacgaggcct t                                           21

<210> SEQ ID NO 74
<211> LENGTH: 21
<212> TYPE: DNA
<213> ORGANISM: Artificial
<220> FEATURE:
<223> OTHER INFORMATION: Synthetic

<400> SEQUENCE: 74
ggccucgugc ggcgagcgct t                                           21

<210> SEQ ID NO 75
<211> LENGTH: 21
<212> TYPE: DNA
<213> ORGANISM: Artificial
<220> FEATURE:
<223> OTHER INFORMATION: Synthetic

<400> SEQUENCE: 75
cuucgugggc ccgcgaugct t                                              21

<210> SEQ ID NO 76
<211> LENGTH: 21
<212> TYPE: DNA
<213> ORGANISM: Artificial
<220> FEATURE:
<223> OTHER INFORMATION: Synthetic

<400> SEQUENCE: 76
gcaucgcggg cccacgaagt t                                              21

<210> SEQ ID NO 77
<211> LENGTH: 21
<212> TYPE: DNA
<213> ORGANISM: Artificial
<220> FEATURE:
<223> OTHER INFORMATION: Synthetic

<400> SEQUENCE: 77
aagaacgccg ggacaugcct t                                              21

<210> SEQ ID NO 78
<211> LENGTH: 21
<212> TYPE: DNA
<213> ORGANISM: Artificial
<220> FEATURE:
<223> OTHER INFORMATION: Synthetic

<400> SEQUENCE: 78
ggcaugnccc ggcguucuut t                                              21

<210> SEQ ID NO 79
<211> LENGTH: 21
<212> TYPE: DNA
<213> ORGANISM: Artificial
<220> FEATURE:
<223> OTHER INFORMATION: Synthetic

<400> SEQUENCE: 79
caugccacgu gguggaccgt t                                              21

<210> SEQ ID NO 80
<211> LENGTH: 21
<212> TYPE: DNA
<213> ORGANISM: Artificial
<220> FEATURE:
<223> OTHER INFORMATION: Synthetic

<400> SEQUENCE: 80
cgguccacca cguggcaugt t                                              21

<210> SEQ ID NO 81
<211> LENGTH: 21
<212> TYPE: DNA
<213> ORGANISM: Artificial
<220> FEATURE:
<223> OTHER INFORMATION: Synthetic

<400> SEQUENCE: 81
cggaguacaa gugccgcugt t                                              21

<210> SEQ ID NO 82

```
<211> LENGTH: 21
<212> TYPE: DNA
<213> ORGANISM: Artificial
<220> FEATURE:
<223> OTHER INFORMATION: Synthetic

<400> SEQUENCE: 82
cagcggcacu uguacuccgt t                                              21

<210> SEQ ID NO 83
<211> LENGTH: 21
<212> TYPE: DNA
<213> ORGANISM: Artificial
<220> FEATURE:
<223> OTHER INFORMATION: Synthetic

<400> SEQUENCE: 83
ugccggcagg augucaacgt t                                              21

<210> SEQ ID NO 84
<211> LENGTH: 21
<212> TYPE: DNA
<213> ORGANISM: Artificial
<220> FEATURE:
<223> OTHER INFORMATION: Synthetic

<400> SEQUENCE: 84
cguugacauc cugccggcat t                                              21

<210> SEQ ID NO 85
<211> LENGTH: 21
<212> TYPE: DNA
<213> ORGANISM: Artificial
<220> FEATURE:
<223> OTHER INFORMATION: Synthetic

<400> SEQUENCE: 85
gagggugugc acugcgaggt t                                              21

<210> SEQ ID NO 86
<211> LENGTH: 21
<212> TYPE: DNA
<213> ORGANISM: Artificial
<220> FEATURE:
<223> OTHER INFORMATION: Synthetic

<400> SEQUENCE: 86
ccucgcagug cacacccuct t                                              21

<210> SEQ ID NO 87
<211> LENGTH: 21
<212> TYPE: DNA
<213> ORGANISM: Artificial
<220> FEATURE:
<223> OTHER INFORMATION: Synthetic

<400> SEQUENCE: 87
ggacccaaca cuuacaccut t                                              21

<210> SEQ ID NO 88
<211> LENGTH: 21
<212> TYPE: DNA
<213> ORGANISM: Artificial
<220> FEATURE:
<223> OTHER INFORMATION: Synthetic

<400> SEQUENCE: 88
```

-continued aguguuaagu guuggguccu u     21

<210> SEQ ID NO 89
<211> LENGTH: 21
<212> TYPE: DNA
<213> ORGANISM: Artificial
<220> FEATURE:
<223> OTHER INFORMATION: Synthetic

<400> SEQUENCE: 89
cugcaaggac ggcgucgccu u     21

<210> SEQ ID NO 90
<211> LENGTH: 21
<212> TYPE: DNA
<213> ORGANISM: Artificial
<220> FEATURE:
<223> OTHER INFORMATION: Synthetic

<400> SEQUENCE: 90
ggcgacgccg uccuugcagu u     21

<210> SEQ ID NO 91
<211> LENGTH: 21
<212> TYPE: DNA
<213> ORGANISM: Artificial
<220> FEATURE:
<223> OTHER INFORMATION: Synthetic

<400> SEQUENCE: 91
gcacguguau ugacgacguu u     21

<210> SEQ ID NO 92
<211> LENGTH: 21
<212> TYPE: DNA
<213> ORGANISM: Artificial
<220> FEATURE:
<223> OTHER INFORMATION: Synthetic

<400> SEQUENCE: 92
acgucgucaa uacacgugcu u     21

<210> SEQ ID NO 93
<211> LENGTH: 21
<212> TYPE: DNA
<213> ORGANISM: Artificial
<220> FEATURE:
<223> OTHER INFORMATION: Synthetic

<400> SEQUENCE: 93
cacguguauu gacgacguuu u     21

<210> SEQ ID NO 94
<211> LENGTH: 21
<212> TYPE: DNA
<213> ORGANISM: Artificial
<220> FEATURE:
<223> OTHER INFORMATION: Synthetic

<400> SEQUENCE: 94
aacgucguca auacacgugu u     21

<210> SEQ ID NO 95
<211> LENGTH: 21
<212> TYPE: DNA

```
<213> ORGANISM: Artificial
<220> FEATURE:
<223> OTHER INFORMATION: Synthetic

<400> SEQUENCE: 95
acguguauug acgacguugt t                                              21

<210> SEQ ID NO 96
<211> LENGTH: 21
<212> TYPE: DNA
<213> ORGANISM: Artificial
<220> FEATURE:
<223> OTHER INFORMATION: Synthetic

<400> SEQUENCE: 96
caacgucguc aauacacgut t                                              21

<210> SEQ ID NO 97
<211> LENGTH: 21
<212> TYPE: DNA
<213> ORGANISM: Artificial
<220> FEATURE:
<223> OTHER INFORMATION: Synthetic

<400> SEQUENCE: 97
ggacgagugc ucacccagct t                                              21

<210> SEQ ID NO 98
<211> LENGTH: 21
<212> TYPE: DNA
<213> ORGANISM: Artificial
<220> FEATURE:
<223> OTHER INFORMATION: Synthetic

<400> SEQUENCE: 98
gcugggugag cacucgucct t                                              21

<210> SEQ ID NO 99
<211> LENGTH: 21
<212> TYPE: DNA
<213> ORGANISM: Artificial
<220> FEATURE:
<223> OTHER INFORMATION: Synthetic

<400> SEQUENCE: 99
ccaucaagcg ugccgccgat t                                              21

<210> SEQ ID NO 100
<211> LENGTH: 21
<212> TYPE: DNA
<213> ORGANISM: Artificial
<220> FEATURE:
<223> OTHER INFORMATION: Synthetic

<400> SEQUENCE: 100
ucggcggcac gcuugauggt t                                              21

<210> SEQ ID NO 101
<211> LENGTH: 21
<212> TYPE: DNA
<213> ORGANISM: Artificial
<220> FEATURE:
<223> OTHER INFORMATION: Synthetic

<400> SEQUENCE: 101
ccgguucgag gagcccgugt t                                              21
```

```
<210> SEQ ID NO 102
<211> LENGTH: 21
<212> TYPE: DNA
<213> ORGANISM: Artificial
<220> FEATURE:
<223> OTHER INFORMATION: Synthetic

<400> SEQUENCE: 102
cacgggcucc ucgaaccggt t                                              21

<210> SEQ ID NO 103
<211> LENGTH: 21
<212> TYPE: DNA
<213> ORGANISM: Artificial
<220> FEATURE:
<223> OTHER INFORMATION: Synthetic

<400> SEQUENCE: 103
ccgggacauc acggaucaut t                                              21

<210> SEQ ID NO 104
<211> LENGTH: 21
<212> TYPE: DNA
<213> ORGANISM: Artificial
<220> FEATURE:
<223> OTHER INFORMATION: Synthetic

<400> SEQUENCE: 104
augauccgug augucccggt t                                              21

<210> SEQ ID NO 105
<211> LENGTH: 21
<212> TYPE: DNA
<213> ORGANISM: Artificial
<220> FEATURE:
<223> OTHER INFORMATION: Synthetic

<400> SEQUENCE: 105
gacaucgcac aggagcgcat t                                              21

<210> SEQ ID NO 106
<211> LENGTH: 21
<212> TYPE: DNA
<213> ORGANISM: Artificial
<220> FEATURE:
<223> OTHER INFORMATION: Synthetic

<400> SEQUENCE: 106
ugcgcuccug ugcgauguct t                                              21

<210> SEQ ID NO 107
<211> LENGTH: 21
<212> TYPE: DNA
<213> ORGANISM: Artificial
<220> FEATURE:
<223> OTHER INFORMATION: Synthetic

<400> SEQUENCE: 107
cagagcggca uggugccgat t                                              21

<210> SEQ ID NO 108
<211> LENGTH: 21
<212> TYPE: DNA
<213> ORGANISM: Artificial
<220> FEATURE:
```

<223> OTHER INFORMATION: Synthetic

<400> SEQUENCE: 108
ucggcaccau gccgcucugt t                                    21

<210> SEQ ID NO 109
<211> LENGTH: 21
<212> TYPE: DNA
<213> ORGANISM: Artificial
<220> FEATURE:
<223> OTHER INFORMATION: Synthetic

<400> SEQUENCE: 109
cauggugccg aaccaauact t                                    21

<210> SEQ ID NO 110
<211> LENGTH: 21
<212> TYPE: DNA
<213> ORGANISM: Artificial
<220> FEATURE:
<223> OTHER INFORMATION: Synthetic

<400> SEQUENCE: 110
guauugguuc ggcaccaugt t                                    21

<210> SEQ ID NO 111
<211> LENGTH: 21
<212> TYPE: DNA
<213> ORGANISM: Artificial
<220> FEATURE:
<223> OTHER INFORMATION: Synthetic

<400> SEQUENCE: 111
uggugccgaa ccaauacaat t                                    21

<210> SEQ ID NO 112
<211> LENGTH: 21
<212> TYPE: DNA
<213> ORGANISM: Artificial
<220> FEATURE:
<223> OTHER INFORMATION: Synthetic

<400> SEQUENCE: 112
uuguauuggu ucggcaccat t                                    21

<210> SEQ ID NO 113
<211> LENGTH: 21
<212> TYPE: DNA
<213> ORGANISM: Artificial
<220> FEATURE:
<223> OTHER INFORMATION: Synthetic

<400> SEQUENCE: 113
cucgccugug gacaacacct t                                    21

<210> SEQ ID NO 114
<211> LENGTH: 21
<212> TYPE: DNA
<213> ORGANISM: Artificial
<220> FEATURE:
<223> OTHER INFORMATION: Synthetic

<400> SEQUENCE: 114
gguguugucc acaggcgagt t                                    21

```
<210> SEQ ID NO 115
<211> LENGTH: 21
<212> TYPE: DNA
<213> ORGANISM: Artificial
<220> FEATURE:
<223> OTHER INFORMATION: Synthetic

<400> SEQUENCE: 115
gaccaguggu ccagcucgut t                                              21

<210> SEQ ID NO 116
<211> LENGTH: 21
<212> TYPE: DNA
<213> ORGANISM: Artificial
<220> FEATURE:
<223> OTHER INFORMATION: Synthetic

<400> SEQUENCE: 116
acgagcugga ccacugguct t                                              21

<210> SEQ ID NO 117
<211> LENGTH: 21
<212> TYPE: DNA
<213> ORGANISM: Artificial
<220> FEATURE:
<223> OTHER INFORMATION: Synthetic

<400> SEQUENCE: 117
cauuccaacg ucuccgacut t                                              21

<210> SEQ ID NO 118
<211> LENGTH: 21
<212> TYPE: DNA
<213> ORGANISM: Artificial
<220> FEATURE:
<223> OTHER INFORMATION: Synthetic

<400> SEQUENCE: 118
agucggagac guuggaaugt t                                              21

<210> SEQ ID NO 119
<211> LENGTH: 21
<212> TYPE: DNA
<213> ORGANISM: Artificial
<220> FEATURE:
<223> OTHER INFORMATION: Synthetic

<400> SEQUENCE: 119
auuccaacgu cuccgacugt t                                              21

<210> SEQ ID NO 120
<211> LENGTH: 21
<212> TYPE: DNA
<213> ORGANISM: Artificial
<220> FEATURE:
<223> OTHER INFORMATION: Synthetic

<400> SEQUENCE: 120
cagucggaga cguuggaaut t                                              21

<210> SEQ ID NO 121
<211> LENGTH: 23
<212> TYPE: DNA
<213> ORGANISM: Artificial
<220> FEATURE:
<223> OTHER INFORMATION: Synthetic
```

```
<400> SEQUENCE: 121
uuccaacguc uccgacuggd tdt                                              23

<210> SEQ ID NO 122
<211> LENGTH: 21
<212> TYPE: DNA
<213> ORGANISM: Artificial
<220> FEATURE:
<223> OTHER INFORMATION: Synthetic

<400> SEQUENCE: 122
ccagucggag acguuggaat t                                                21

<210> SEQ ID NO 123
<211> LENGTH: 21
<212> TYPE: DNA
<213> ORGANISM: Artificial
<220> FEATURE:
<223> OTHER INFORMATION: Synthetic

<400> SEQUENCE: 123
caacgucucc gacuggucct t                                                21

<210> SEQ ID NO 124
<211> LENGTH: 21
<212> TYPE: DNA
<213> ORGANISM: Artificial
<220> FEATURE:
<223> OTHER INFORMATION: Synthetic

<400> SEQUENCE: 124
ggaccagucg gagacguugt t                                                21

<210> SEQ ID NO 125
<211> LENGTH: 21
<212> TYPE: DNA
<213> ORGANISM: Artificial
<220> FEATURE:
<223> OTHER INFORMATION: Synthetic

<400> SEQUENCE: 125
acgucuccga cugguccgat t                                                21

<210> SEQ ID NO 126
<211> LENGTH: 21
<212> TYPE: DNA
<213> ORGANISM: Artificial
<220> FEATURE:
<223> OTHER INFORMATION: Synthetic

<400> SEQUENCE: 126
ucggaccagu cggagacgut t                                                21

<210> SEQ ID NO 127
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-F modified
<220> FEATURE:
<221> NAME/KEY: misc_feature
<222> LOCATION: (2)..(2)
<223> OTHER INFORMATION: Nucleotide is 2'-F modified
```

-continued

```
<220> FEATURE:
<221> NAME/KEY: misc_feature
<222> LOCATION: (3)..(3)
<223> OTHER INFORMATION: Nucleotide is 2'-O-methyl modified
<220> FEATURE:
<221> NAME/KEY: misc_feature
<222> LOCATION: (4)..(4)
<223> OTHER INFORMATION: Nucleotide is 2'-F modified
<220> FEATURE:
<221> NAME/KEY: misc_feature
<222> LOCATION: (5)..(5)
<223> OTHER INFORMATION: Nucleotide is 2'-O-methyl modified
<220> FEATURE:
<221> NAME/KEY: misc_feature
<222> LOCATION: (6)..(6)
<223> OTHER INFORMATION: Nucleotide is 2'-F modified
<220> FEATURE:
<221> NAME/KEY: misc_feature
<222> LOCATION: (7)..(7)
<223> OTHER INFORMATION: Nucleotide is 2'-O-methyl modified
<220> FEATURE:
<221> NAME/KEY: misc_feature
<222> LOCATION: (8)..(8)
<223> OTHER INFORMATION: Nucleotide is 2'-F modified
<220> FEATURE:
<221> NAME/KEY: misc_feature
<222> LOCATION: (9)..(9)
<223> OTHER INFORMATION: Nucleotide is 2'-O-methyl modified
<220> FEATURE:
<221> NAME/KEY: misc_feature
<222> LOCATION: (10)..(10)
<223> OTHER INFORMATION: Nucleotide is 2'-F modified
<220> FEATURE:
<221> NAME/KEY: misc_feature
<222> LOCATION: (11)..(11)
<223> OTHER INFORMATION: Nucleotide is 2'-O-methyl modified
<220> FEATURE:
<221> NAME/KEY: misc_feature
<222> LOCATION: (12)..(12)
<223> OTHER INFORMATION: Nucleotide is 2'-F modified
<220> FEATURE:
<221> NAME/KEY: misc_feature
<222> LOCATION: (13)..(13)
<223> OTHER INFORMATION: Nucleotide is 2'-O-methyl modified
<220> FEATURE:
<221> NAME/KEY: misc_feature
<222> LOCATION: (14)..(14)
<223> OTHER INFORMATION: Nucleotide is 2'-F modified
<220> FEATURE:
<221> NAME/KEY: misc_feature
<222> LOCATION: (15)..(15)
<223> OTHER INFORMATION: Nucleotide is 2'-O-methyl modified
<220> FEATURE:
<221> NAME/KEY: misc_feature
<222> LOCATION: (16)..(16)
<223> OTHER INFORMATION: Nucleotide is 2'-F modified
<220> FEATURE:
<221> NAME/KEY: misc_feature
<222> LOCATION: (17)..(17)
<223> OTHER INFORMATION: Nucleotide is 2'-O-methyl modified
<220> FEATURE:
<221> NAME/KEY: misc_feature
<222> LOCATION: (18)..(18)
<223> OTHER INFORMATION: Nucleotide is 2'-F modified
<220> FEATURE:
<221> NAME/KEY: misc_feature
<222> LOCATION: (19)..(19)
<223> OTHER INFORMATION: Nucleotide is 2'-O-methyl modified
<220> FEATURE:
<221> NAME/KEY: misc_feature
<222> LOCATION: (20)..(21)
<223> OTHER INFORMATION: Nucleotides linked by phosphothioate

<400> SEQUENCE: 127
ugcgcuccug ugcgauguct t                                          21

<210> SEQ ID NO 128
```

```
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide is 2'-O-methyl modified
<220> FEATURE:
<221> NAME/KEY: misc_feature
<222> LOCATION: (2)..(2)
<223> OTHER INFORMATION: Nucleotide is 2'-O-methyl modified
<220> FEATURE:
<221> NAME/KEY: misc_feature
<222> LOCATION: (3)..(3)
<223> OTHER INFORMATION: Nucleotide is 2'-F modified
<220> FEATURE:
<221> NAME/KEY: misc_feature
<222> LOCATION: (4)..(4)
<223> OTHER INFORMATION: Nucleotide is 2'-O-methyl modified
<220> FEATURE:
<221> NAME/KEY: misc_feature
<222> LOCATION: (5)..(5)
<223> OTHER INFORMATION: Nucleotide is 2'-F modified
<220> FEATURE:
<221> NAME/KEY: misc_feature
<222> LOCATION: (6)..(6)
<223> OTHER INFORMATION: Nucleotide is 2'-O-methyl modified
<220> FEATURE:
<221> NAME/KEY: misc_feature
<222> LOCATION: (7)..(7)
<223> OTHER INFORMATION: Nucleotide is 2'-F modified
<220> FEATURE:
<221> NAME/KEY: misc_feature
<222> LOCATION: (8)..(8)
<223> OTHER INFORMATION: Nucleotide is 2'-O-methyl modified
<220> FEATURE:
<221> NAME/KEY: misc_feature
<222> LOCATION: (9)..(9)
<223> OTHER INFORMATION: Nucleotide is 2'-F modified
<220> FEATURE:
<221> NAME/KEY: misc_feature
<222> LOCATION: (10)..(10)
<223> OTHER INFORMATION: Nucleotide is 2'-O-methyl modified
<220> FEATURE:
<221> NAME/KEY: misc_feature
<222> LOCATION: (11)..(11)
<223> OTHER INFORMATION: Nucleotide is 2'-F modified
<220> FEATURE:
<221> NAME/KEY: misc_feature
<222> LOCATION: (12)..(12)
<223> OTHER INFORMATION: Nucleotide is 2'-O-methyl modified
<220> FEATURE:
<221> NAME/KEY: misc_feature
<222> LOCATION: (13)..(13)
<223> OTHER INFORMATION: Nucleotide is 2'-F modified
<220> FEATURE:
<221> NAME/KEY: misc_feature
<222> LOCATION: (14)..(14)
<223> OTHER INFORMATION: Nucleotide is 2'-O-methyl modified
<220> FEATURE:
<221> NAME/KEY: misc_feature
<222> LOCATION: (15)..(15)
<223> OTHER INFORMATION: Nucleotide is 2'-F modified
<220> FEATURE:
<221> NAME/KEY: misc_feature
<222> LOCATION: (16)..(16)
<223> OTHER INFORMATION: Nucleotide is 2'-O-methyl modified
<220> FEATURE:
<221> NAME/KEY: misc_feature
<222> LOCATION: (17)..(17)
<223> OTHER INFORMATION: Nucleotide is 2'-F modified
<220> FEATURE:
<221> NAME/KEY: misc_feature
<222> LOCATION: (18)..(18)
<223> OTHER INFORMATION: Nucleotide is 2'-O-methyl modified
<220> FEATURE:
<221> NAME/KEY: misc_feature
```

```
<222> LOCATION: (19)..(19)
<223> OTHER INFORMATION: Nucleotide is 2'-F modified
<220> FEATURE:
<221> NAME/KEY: misc_feature
<222> LOCATION: (20)..(21)
<223> OTHER INFORMATION: Nucleotides linked by phosphothioate

<400> SEQUENCE: 128
gacaucgcac aggagcgcat t                                              21
```

NOTCH 1 SPECIFIC SIRNA MOLECULE

CROSS-REFERENCE TO RELATED APPLICATIONS

The present patent application claims the priority benefit of U.S. patent application Ser. No. 15/026,084, filed on Mar. 30, 2016, now U.S. Pat. No. 986,690, which was a national phase of PCT/EP2014/002655 (WO 2015/043768 A1), filed Sep. 30, 2014, which in turn claims priority from EP13004722.8A and 13004722.8. Each of the above is incorporated herein in their entirety.

The present invention is related to a nucleic acid molecule comprising a double-stranded structure, the nucleic acid molecule comprising a double-stranded structure for use in a method for the treatment and/or prevention of a disease, the nucleic acid molecule comprising a double-stranded structure for use in a method of restoring drug sensitivity of cancer cells, use of nucleic acid molecule comprising a double-stranded structure for the manufacture of a medicament, use of the nucleic acid molecule comprising a double-stranded structure in the manufacture of an agent for restoring drug sensitivity of cancer cells, a nanoemulsion comprising the nucleic acid molecule comprising a double-stranded structure, the nanoemulsion for use in a method for the treatment and/or prevention of a disease, the nanoemulsion for use in a method of restoring drug sensitivity of cancer cells, use of the nanoemulsion structure for the manufacture of a medicament, use of the nanoemulsion in the manufacture of an agent for restoring drug sensitivity of cancer cells, a pharmaceutical composition comprising the nucleic acid molecule comprising a double-stranded structure, the pharmaceutical composition for use in a method for the treatment and/or prevention of a disease, the pharmaceutical composition for use in a method for restoring drug sensitivity of cancer cells, a method for the treatment and/or prevention of a disease comprising the administration of the nucleic acid molecule comprising a double-stranded structure, a method for restoring drug sensitivity of cancer cells comprising the administration of the nucleic acid molecule comprising a double-stranded structure, a kit comprising the nucleic acid molecule comprising a double-stranded structure, the kit for use in a method of treatment and/or prevention of a disease, the kit for use in a method for restoring drug sensitivity of cancer cells, a kit comprising the nanoemulsion, the kit for use in a method of treatment and/or prevention of a disease, and the kit for use in a method for restoring drug sensitivity of cancer cells.

Notch 1 is a gene coding for a single-pass transmembrane receptor which is also categorized as a Type 1 transmembrane protein. Human Notch 1 was described for the first time by Ellisen L W et al. (Ellisen L W et al., Cell 66(4), 649-661 (1991)). Notch 1 is a member of the Notch family. Members of this family share structural characteristics including an extracellular domain consisting of multiple epidermal growth factor-like (EGF) repeats, and an intracellular domain consisting of multiple, different domain types. Notch family members play a role in a variety of developmental processes by controlling cell fate decisions. The Notch signaling network is an evolutionarily conserved intercellular signaling pathway that regulates interactions between physically adjacent cells. Notch 1 and its translation product constitute a drugable target in many tumor entities. Sequence information including the nucleotide sequence of the cDNA of human Notch 1 may, for example, be retrieved from GenBank entry NM_017617.3.

There is an ongoing need in the art for means of silencing or knocking down the expression levels of Notch 1 in vitro and in vivo, including the use of siRNA for the treatment of disease which can be treated or prevented by decreasing the expression of the Notch 1 gene and more specifically by decreasing the translation of mRNA coding for Notch 1. One group of diseases which can be treated that way are various tumor diseases and cancer.

Therefore, the problem underlying the present invention is the provision of a means for silencing of knocking down Notch 1 and more preferably silencing or knocking down the expression levels of Notch 1 in vitro and in vivo. A further problem underlying the invention is the provision of a method for the treatment of a disease, more preferably disease which can be treated or prevented by decreasing the expression of the Notch 1 gene and more specifically by decreasing the translation of mRNA coding for Notch 1, and of a means which is useful in such method. A still further problem underlying the problem is the provision of a method for restoring drug sensitivity of cancer cells, and of a means which is useful in such method. Finally, the problem underlying the present invention is the provision of a method for adjunct therapy in the treatment of cancer, and of a means which is useful in such method.

These and other problems underlying the present invention are solved by the subject matter of the attached independent claims. Preferred embodiments may be taken from the attached dependent claims.

Certain embodiments will become apparent to the skilled person in view of the description, including those embodiments set forth below. Those embodiments set forth below equally solve the above and other problems underlying the present invention.

EMBODIMENT 1

A nucleic acid molecule comprising a double-stranded structure, wherein the double-stranded structure is formed by a first strand and a second strand, wherein the first strand comprises a first stretch of contiguous nucleotides and the second strand comprises a second stretch of contiguous nucleotides, wherein the first stretch of contiguous nucleotides comprises a) a nucleotide sequence, wherein the nucleotide sequence is at least 63% identical to (i) nucleotide sequence
        (SEQ ID NO: 1)
    5' ACGAGCUGGACCACUGGUC 3'
    or (ii) nucleotide sequence
        (SEQ ID NO: 8)
    5' CGAGCUGGACCACUGGU 3';

or b) a nucleotide sequence, wherein the nucleotide sequence comprises at least a stretch of 8 or 9 nucleotides of (i) nucleotide sequence
        (SEQ ID NO: 1)
    5' ACGAGCUGGACCACUGGUC 3'
    or -continued

```
        (ii) nucleotide sequence
                                          (SEQ ID NO: 8)
        5' CGAGCUGGACCACUGGU 3'
``` and
wherein the nucleic acid molecule is capable of causing post-transcriptional silencing of a gene.

EMBODIMENT 2

The nucleic acid molecule of embodiment 1, wherein post-transcriptional silencing of a gene is RNA interference.

EMBODIMENT 3

The nucleic acid molecule of any one of embodiments 1 to 2, wherein the gene is Notch 1, preferably human Notch 1.

EMBODIMENT 4

The nucleic acid molecule of any one of embodiments 1 to 3, wherein the nucleic acid molecule is capable of degrading mRNA coding for the gene or a precursor of said mRNA, preferably in a cell.

EMBODIMENT 5

The nucleic acid molecule of embodiment 4, wherein the nucleotide sequence of a cDNA of the mRNA is available from GenBank entry NM_017617.3.

EMBODIMENT 6

The nucleic acid molecule of any one of embodiments 1 to 5, wherein the cDNA consists of the nucleotide sequence of SEQ ID NO: 2

EMBODIMENT 7

The nucleic acid molecule of any one of embodiments 1 to 6, wherein the second stretch of contiguous nucleotides is at least partially complementary to a part of the first stretch of contiguous nucleotides.

EMBODIMENT 8

The nucleic acid molecule of any one of embodiments 1 to 7, wherein the second stretch of contiguous nucleotides is at least partially complementary to the first stretch of contiguous nucleotides.

EMBODIMENT 9

The nucleic acid molecule of any one of embodiments 1 to 8, wherein the first stretch of contiguous nucleotides comprises 13 to 29 nucleotides, preferably 17 to 25 or 19 to 25 nucleotides and more preferably 19 to 23 nucleotides.

EMBODIMENT 10

The nucleic acid molecule of any one of embodiments 1 to 9, wherein the second stretch of contiguous nucleotides comprises 13 to 29 nucleotides, preferably 17 to 25 or 19 to 25 nucleotides and more preferably 19 to 23 nucleotides.

EMBODIMENT 11

The nucleic acid molecule of any one of embodiments 1 to 10, wherein the first stretch of contiguous nucleotides and the second stretch of contiguous nucleotides comprises 13 to 29 nucleotides, preferably 17 to 25 or 19 to 25 nucleotides and more preferably 19 to 23 nucleotides.

EMBODIMENT 12

The nucleic acid molecule of any one of embodiments 9 to 11, wherein the nucleotides are consecutive nucleotides.

EMBODIMENT 13

The nucleic acid molecule of any one of embodiments 1 to 12, wherein the first strand consists of the first stretch of contiguous nucleotides.

EMBODIMENT 14

The nucleic acid molecule of any one of embodiments 1 to 13, wherein the second strand consist of the second stretch of contiguous nucleotides.

EMBODIMENT 15

The nucleic acid molecule of any one of embodiments 1 to 14, wherein the first strand consists of the first stretch of contiguous nucleotides and the second strand consists of the second stretch of contiguous nucleotides.

EMBODIMENT 16

The nucleic acid molecule of any one of embodiments 1 to 14, wherein the double-stranded structure comprises 13 to 29 base pairs, preferably 16 to 27 or 19 to 25 base pairs and more preferably 19 to 23 base pairs.

EMBODIMENT 17

The nucleic acid molecule of any one of embodiments 1 to 16, wherein the first stretch of contiguous nucleotides comprises

```
        (i) nucleotide sequence
                                          (SEQ ID NO: 1)
        5' ACGAGCUGGACCACUGGUC 3'
        or (ii) nucleotide sequence
                                          (SEQ ID NO: 8)
        5' CGAGCUGGACCACUGGU 3'.
```

EMBODIMENT 18

The nucleic acid molecule of any one of embodiments 1 to 17, wherein the second stretch of contiguous nucleotides comprises

```
        (i) nucleotide sequence
                                          (SEQ ID NO: 3)
        5' GACCAGUGGUCCAGCUCGU 3'
        or
```

-continued

```
        (ii) nucleotide sequence
                                  (SEQ ID NO: 9)
        5' ACCAGUGGUCCAGCUCG 3'.
```

EMBODIMENT 19

The nucleic acid molecule of any one of embodiments 17 to 18, wherein the first stretch of contiguous nucleotides comprises

```
        (i) nucleotide sequence
                                  (SEQ ID NO: 1)
        5' ACGAGCUGGACCACUGGUC 3'
        or
        (ii) nucleotide sequence
                                  (SEQ ID NO: 8)
        5' CGAGCUGGACCACUGGU 3',
``` and
the second stretch of contiguous nucleotides comprises

```
        (i) nucleotide sequence
                                  (SEQ ID NO: 3)
        5' GACCAGUGGUCCAGCUCGU 3'
        or
        (ii) nucleotide sequence
                                  (SEQ ID NO: 9)
        5' ACCAGUGGUCCAGCUCG 3'.
```

EMBODIMENT 20

The nucleic acid molecule of any one of embodiments 1 to 19, wherein the nucleic acid molecule is blunt ended at at least one end.

EMBODIMENT 21

The nucleic acid molecule of embodiment 20, wherein the nucleic acid molecule is blunt ended at the end defined by the 5' end of the first strand and the 3' end of the second strand.

EMBODIMENT 22

The nucleic acid molecule of embodiment 20, wherein the nucleic acid molecule is blunt ended at the end defined by the 3' end of the first strand and the 5' end of the second strand.

EMBODIMENT 23

The nucleic acid molecule of any one of embodiments 20 to 22, wherein the nucleic acid molecule is blunt ended at the end defined by the 5' end of the first strand and the 3' end of the second strand and at the end defined by the 3' end of the first strand and the 5' end of the second strand.

EMBODIMENT 24

The nucleic acid molecule of any one of embodiments 1 to 19, wherein the nucleic acid molecule has an overhang at at least one end.

EMBODIMENT 25

The nucleic acid molecule of embodiment 24, wherein the nucleic acid molecule has an overhang at the end defined by the 5' end of the first strand and the 3' end of the second strand.

EMBODIMENT 26

The nucleic acid molecule of embodiment 25, wherein the overhang is a 5' overhang.

EMBODIMENT 27

The nucleic acid molecule of embodiment 25, wherein the overhang is a 3' overhang.

EMBODIMENT 28

The nucleic acid molecule of embodiment 24, wherein the nucleic acid molecule has an overhang at the end defined by the 3' end of the first strand and the 5' end of the second strand.

EMBODIMENT 29

The nucleic acid molecule of embodiment 28, wherein the overhang is a 5' overhang.

EMBODIMENT 30

The nucleic acid molecule of embodiment 28, wherein the overhang is a 3' overhang.

EMBODIMENT 31

The nucleic acid molecule of embodiment 24, wherein the nucleic acid molecule has an overhang at the end defined by the 5' end of the first strand and the 3' end of the second strand and at the end defined by the 3' end of the first strand and the 5' end of the second strand.

EMBODIMENT 32

The nucleic acid molecule of embodiment 31, wherein the overhang is a 5'overhang.

EMBODIMENT 33

The nucleic acid molecule of embodiment 32, wherein the overhang is a 3' overhang.

EMBODIMENT 34

The nucleic acid molecule of any one of embodiments 24 to 33, wherein the overhang consists of one, two, three, four or five nucleotides.

EMBODIMENT 35

The nucleic acid molecule of embodiment 34, wherein the overhang consists of two nucleotides.

EMBODIMENT 36

The nucleic acid molecule of any one of embodiments 34 to 35, wherein the nucleotide is dT.

EMBODIMENT 37

The nucleic acid molecule of any one of embodiments 1 to 19 and 24 to 36, wherein the first stretch of contiguous nucleotides comprises

```
(i) nucleotide sequence
                              (SEQ ID NO: 4)
5' ACGAGCUGGACCACUGGUCdTdT 3'
or
(ii) nucleotide sequence
                              (SEQ ID NO: 10)
5' CGAGCUGGACCACUGGUdTdT 3'.
```

EMBODIMENT 38

The nucleic acid molecule of any one of embodiments 1 to 19 and 24 to 37, wherein the second stretch of contiguous nucleotides comprises

```
(i) nucleotide sequence
                              (SEQ ID NO: 5)
5' GACCAGUGGUCCAGCUCGUdTdT 3'
or
(ii) nucleotide sequence
                              (SEQ ID NO: 11)
5' ACCAGUGGUCCAGCUCGdTdT 3'.
```

EMBODIMENT 39

The nucleic acid molecule of any one of embodiments 37 to 38, wherein
the first stretch of contiguous nucleotides comprises

```
(i) nucleotide sequence
                              (SEQ ID NO: 4)
5' ACGAGCUGGACCACUGGUCdTdT 3'
or
(i) nucleotide sequence
                              (SEQ ID NO: 10)
5' CGAGCUGGACCACUGGUdTdT 3',
``` and
the second stretch of contiguous nucleotides comprises

```
(i) nucleotide sequence
                              (SEQ ID NO: 5)
5' GACCAGUGGUCCAGCUCGUdTdT 3'
or
(ii) nucleotide sequence
                              (SEQ ID NO: 11)
5' ACCAGUGGUCCAGCUCGdTdT 3'.
```

EMBODIMENT 40

The nucleic acid molecule of any one of the preceding embodiments, wherein the first strand and the second strand are covalently linked to each other, preferably the 3' end of the first strand is covalently linked to the 5' end of the second strand.

EMBODIMENT 41

The nucleic acid molecule of any one of embodiments 1 to 40, wherein one or more of the nucleotides forming the first stretch of contiguous nucleotides is modified.

EMBODIMENT 42

The nucleic acid molecule of any one of embodiments 1 to 41, wherein one or more of the nucleotides forming the second stretch of contiguous nucleotides is modified.

EMBODIMENT 43

The nucleic acid molecule of any one of embodiments 41 and 42, wherein one or more of the nucleotides forming the first stretch of contiguous nucleotides is modified and one or more of the nucleotides forming the second stretch of contiguous nucleotides is modified

EMBODIMENT 44

The nucleic acid molecule of any one of embodiments 1 to 43, wherein one or more of the nucleotides forming the first strand is modified.

EMBODIMENT 45

The nucleic acid molecule of any one of embodiments 1 to 44, wherein one or more of the nucleotides forming the second strand is modified.

EMBODIMENT 46

The nucleic acid molecule of any one of embodiments 44 to 45, wherein one or more of the nucleotides forming the first strand is modified and one or more of the nucleotides forming the second strand is modified.

EMBODIMENT 47

The nucleic acid molecule of any one of embodiments 41 to 46, wherein the modification of the one or more of the nucleotides is a modification of the sugar moiety of the one or more nucleotides and/or a modification of the phosphate moiety of the one or more nucleotides.

EMBODIMENT 48

The nucleic acid molecule of embodiment 47, wherein the modification of the sugar moiety is selected from the group comprising 2'O-methyl and 2'-F.

EMBODIMENT 49

The nucleic acid molecule any one of embodiments 47 to 48, wherein the modification of the phosphate moiety is such that a phosphorothioate linkage is formed between two nucleotides.

EMBODIMENT 50

The nucleic acid molecule of any one of embodiments 41 to 43 and 47 to 49, wherein the one or more of the nucleotides is/are modified depending on the position within the stretch.

EMBODIMENT 51

The nucleic acid molecule of embodiment 50, wherein over the entire length of the first and/or second stretch or part thereof, a nucleotide at an even position of the stretch is modified.

EMBODIMENT 52

The nucleic acid molecule of any one of embodiments 50 and 51, wherein over the entire length of the first and/or second stretch or part thereof a nucleotide at an uneven position of the stretch is modified.

EMBODIMENT 53

The nucleic acid molecule of any one of embodiments 51 to 52, wherein over the entire length of the first and/or the second stretch or part thereof a nucleotide at an even position of the stretch is modified and wherein over the entire length of the first and/or the second stretch or part thereof a nucleotide at an even position of the stretch is modified, wherein the modification of the nucleotide(s) at the even position is different from the modification of the nucleotide(s) at the uneven position.

EMBODIMENT 54

The nucleic acid molecule of any one of embodiments 51 to 53, wherein (a) the modification of the nucleotide(s) at the even position is a 2'-O-methyl modification and the modification of the nucleotides(s) at the uneven position is a 2'-F modification, or (b) the modification of the nucleotide(s) at the uneven position is a 2'-O-methyl modification and the modification of the nucleotides(s) at the even position is a 2'-F modification.

EMBODIMENT 55

The nucleic acid molecule of any one of embodiments 44 to 50, wherein the one or more of the nucleotides is/are modified depending on the position within the strand.

EMBODIMENT 56

The nucleic acid molecule of embodiment 55, wherein over the entire length of the first and/or second strand or part thereof, a nucleotide at an even position of the strand is modified.

EMBODIMENT 57

The nucleic acid molecule of any one of embodiments 55 and 56, wherein over the entire length of the first and/or second strand or part thereof a nucleotide at an uneven position of the strand is modified.

EMBODIMENT 58

The nucleic acid molecule of any one of embodiments 56 to 57, wherein over the entire length of the first and/or the second strand or part thereof a nucleotide at an even position of the strand is modified and wherein over the entire length of the first and/or the second strand or part thereof a nucleotide at an even position of the strand is modified, wherein the modification of the nucleotide(s) at the even position is different from the modification of the nucleotide(s) at the uneven position of the strand.

EMBODIMENT 59

The nucleic acid molecule of any one of embodiments 56 to 58, wherein (a) the modification of the nucleotide(s) at the even position is a 2'-O-methyl modification and the modification of the nucleotides(s) at the uneven position is a 2'-F modification, or (b) the modification of the nucleotide(s) at the uneven position is a 2'-O-methyl modification and the modification of the nucleotides(s) at the even position is a 2'-F modification.

EMBODIMENT 60

The nucleic acid molecule of any one of embodiments 41 to 54, wherein the first stretch comprises at the 5' end at least one, preferably two nucleotides, wherein the at least one nucleotide is 2'-F modified.

EMBODIMENT 61

The nucleic acid molecule of embodiment 60, wherein after the at least one nucleotide the immediately following (in 5'→3' direction) nucleotide and every subsequent second nucleotide is 2' O-methly modified nucleotide over the entire length of the first stretch or part thereof.

EMBODIMENT 62

The nucleic acid molecule of any one of embodiments 60 and 61, wherein starting after the at least one nucleotide the second following (in 5'→3' direction) nucleotide and every subsequent second nucleotide is 2'-F modified nucleotide over the entire length of the first stretch or part thereof.

EMBODIMENT 63

The nucleic acid molecule of any one of embodiments 41 to 55 and 60 to 62, wherein the second stretch comprises at the 5' end at least one, preferably two nucleotides, wherein the at least one nucleotide is 2'-O-methly modified.

EMBODIMENT 64

The nucleic acid molecule of embodiment 63, wherein after the at least one nucleotide the immediately following (in 5'→3' direction) nucleotide and every subsequent second nucleotide is 2'-F modified nucleotide over the entire length of the second stretch or part thereof.

EMBODIMENT 65

The nucleic acid molecule of any one of embodiments 63 and 64, wherein starting after the at least one nucleotide the second following (in 5'→3' direction) nucleotide and every subsequent second nucleotide is 2'-O-methyl modified nucleotide over the entire length of the first stretch or part thereof.

EMBODIMENT 66

The nucleic acid molecule of any one of embodiments 60 to 65, wherein the first stretch comprises at the 5' end at least one, preferably two nucleotides, wherein the at least one nucleotide is 2'-F modified, wherein starting after the at least one nucleotide the second following (in 5'→3' direction) nucleotide and every subsequent second nucleotide is 2'-F modified nucleotide over the entire length of the first stretch or part thereof, wherein the second stretch comprises at the 5' end at least one, preferably two nucleotides, wherein the at least one nucleotide is 2'-O-methly modified, and wherein starting after the at least one nucleotide the second following (in 5'→3' direction) nucleotide and every subsequent second nucleotide is 2'-O-methyl modified nucleotide over the entire length of the first stretch or part thereof.

EMBODIMENT 67

The nucleic acid molecule of any one of embodiments 60 to 66, wherein the first stretch comprises at its 3' end two dT nucleotides and the second stretch comprises at its 3' end two dT nucleotides, wherein the two dT nucleotides are covalently linked through a phosophorothioate bond.

EMBODIMENT 68

The nucleic acid molecule of any one of embodiments 41 to 49 and 55 to 59, wherein the first strand comprises at the 5' end at least one, preferably two nucleotides, wherein the at least one nucleotide is 2'-F modified.

EMBODIMENT 69

The nucleic acid molecule of embodiment 68, wherein after the at least one nucleotide the immediately following (in 5'→3' direction) nucleotide and every subsequent second nucleotide is 2' O-methyl modified nucleotide over the entire length of the first strand or part thereof.

EMBODIMENT 70

The nucleic acid molecule of any one of embodiments 68 and 69, wherein starting after the at least one nucleotide the second following (in 5'→3' direction) nucleotide and every subsequent second nucleotide is 2'-F modified nucleotide over the entire length of the first strand or part thereof.

EMBODIMENT 71

The nucleic acid molecule of any one of embodiments 41 to 49, 55-59 and 68 to 70, wherein the second strand comprises at the 5' end at least one, preferably two nucleotides, wherein the at least one nucleotide is 2'-O-methly modified.

EMBODIMENT 72

The nucleic acid molecule of embodiment 71, wherein after the at least one nucleotide the immediately following (in 5'→3' direction) nucleotide and every subsequent second nucleotide is 2'-F modified nucleotide over the entire length of the second strand or part thereof.

EMBODIMENT 73

The nucleic acid molecule of any one of embodiments 71 and 72, wherein starting after the at least one nucleotide the second following (in 5'→3' direction) nucleotide and every subsequent second nucleotide is 2'-O-methyl modified nucleotide over the entire length of the first strand or part thereof.

EMBODIMENT 74

The nucleic acid molecule of any one of embodiments 68 to 73, wherein the first strand comprises at the 5' end at least one, preferably two nucleotides, wherein the at least one nucleotide is 2'-F modified, wherein starting after the at least one nucleotide the second following (in 5'→3' direction) nucleotide and every subsequent second nucleotide is 2'-F modified nucleotide over the entire length of the first strand or part thereof, wherein the second strand comprises at the 5' end at least one, preferably two nucleotides, wherein the at least one nucleotide is 2'-O-methly modified, and wherein starting after the at least one nucleotide the second following (in 5'→3' direction) nucleotide and every subsequent second nucleotide is 2'-O-methyl modified nucleotide over the entire length of the first strand or part thereof.

EMBODIMENT 75

The nucleic acid molecule of any one of embodiments 68 to 74, wherein the first strand comprises at its 3' end two dT nucleotides and the second strand comprises at its 3' end two dT nucleotides, wherein the two dT nucleotides are covalently linked through a phosphorothioate bond.

EMBODIMENT 76

The nucleic acid molecule of any one of embodiments 1 to 75, wherein the nucleotide sequence

```
                                           (SEQ ID NO: 1)
               5' ACGAGCUGGACCACUGGUC 3'
``` is modified as follows:

```
                                           (SEQ ID NO: 6)
               5' acGaGcUgGaCcAcUgGuC 3',
``` and
the nucleotide sequence

```
                                           (SEQ ID NO: 8)
               5' CGAGCUGGACCACUGGU 3'
``` is modified as follows:

```
                                           (SEQ IO NO: 13)
               5' cgAgCuGgAcCaCuGgU 3',
``` wherein a minor nucleotide indicates that the nucleotide is 2'-F modified and an underlined nucleotide indicates that the nucleotide is 2'-O-methyl modified.

EMBODIMENT 77

The nucleic acid molecule of any one of embodiments 1 to 76, wherein
the nucleotide sequence

```
                                           (SEQ ID NO: 3)
               5' GACCAGUGGUCCAGCUCGU 3'
``` is modified as follows

```
                                           (SEQ ID NO: 7)
               5' GAcCaGuGgUcCaGcUcGu 3',
``` and
the nucleotide sequence 5' ACCAGUGGUCCAGCUCG 3' (SEQ ID NO: 9) is modified as follows 5' <u>AC</u>c<u>AgUgGuCc</u>Ag<u>CuCg</u> 3', (SEQ ID NO: 14)

wherein a minor nucleotide indicates that the nucleotide is 2'-F modified and an underlined nucleotide indicates that the nucleotide is 2'-O-methyl modified.

EMBODIMENT 78

The nucleic acid molecule of any one of embodiments 1 to 77, wherein the first stretch of contiguous nucleotides comprises the following nucleotide sequence:

5' ac<u>GaGcUgGaCcAcUgGuC</u> 3' (SEQ ID NO: 6)
or
5' cg<u>AgCuGgAcCaCuGgU</u> 3', (SEQ IO NO: 13)

wherein a minor nucleotide indicates that the nucleotide is 2'-F modified and an underlined nucleotide indicates that the nucleotide is 2'-O-methyl modified.

EMBODIMENT 79

The nucleic acid molecule of any one of embodiments 1 to 78, wherein the second stretch of contiguous nucleotides comprises the following nucleotide sequence:

5' <u>GA</u>c<u>CaGuGgUcCaGcUcGu</u> 3' (SEQ ID NO: 7)
or
5' <u>AC</u>c<u>AgUgGuCc</u>Ag<u>CuCg</u> 3', (SEQ ID NO: 14)

wherein a minor nucleotide indicates that the nucleotide is 2'-F modified and an underlined nucleotide indicates that the nucleotide is 2'-O-methyl modified.

EMBODIMENT 80

The nucleic acid molecule of any one of embodiments 1 to 79, wherein
a) the first stretch of contiguous nucleotides comprises the following nucleotide sequence:

5' ac<u>GaGcUgGaCcAcUgGuC</u> 3', (SEQ ID NO: 6)

and
the second stretch of contiguous nucleotides comprises the following nucleotide sequence:

5' <u>GA</u>c<u>CaGuGgUcCaGcUcGu</u> 3', (SEQ ID NO: 7)

or
b) the first stretch of contiguous nucleotides comprises the following nucleotide sequence:

5' cg<u>AgCuGgAcCaCuGgU</u> 3', (SEQ IO NO: 13)

and
the second stretch of contiguous nucleotides comprises the following nucleotide sequence:

5' <u>GA</u>c<u>CaGuGgUcCaGcUcGu</u> 3', (SEQ ID NO: 7)

or
c) the first stretch of contiguous nucleotides comprises the following nucleotide sequence:

5' ac<u>GaGcUgGaCcAcUgGuC</u> 3', (SEQ ID NO: 6)

and
the second stretch of contiguous nucleotides comprises the following nucleotide sequence:

5' <u>AC</u>c<u>AgUgGuCc</u>Ag<u>CuCg</u> 3', (SEQ ID NO: 14)

or
d) the first stretch of contiguous nucleotides comprises the following nucleotide sequence:

5' cg<u>AgCuGgAcCaCuGgU</u> 3', (SEQ IO NO: 13)

and
the second stretch of contiguous nucleotides comprises the following nucleotide sequence:

5' <u>AC</u>c<u>AgUgGuCc</u>Ag<u>CuCg</u> 3', (SEQ ID NO: 14)

wherein a minor nucleotide indicates that the nucleotide is 2'-F modified and an underlined nucleotide indicates that the nucleotide is 2'-O-methyl modified.

EMBODIMENT 81

The nucleic acid molecule of any one of embodiments 1 to 80, wherein the nucleic acid molecule consists of a
a) a first stretch of contiguous nucleotides comprises the following nucleotide sequence:

5' ac<u>GaGcUgGaCcAcUgGuC</u> 3', (SEQ ID NO: 6)

and
a second stretch of contiguous nucleotides comprises the following nucleotide sequence:

5' <u>GA</u>c<u>CaGuGgUcCaGcUcGu</u> 3', (SEQ ID NO: 7)

or
b) a first stretch of contiguous nucleotides comprises the following nucleotide sequence:

```
                                          (SEQ IO NO: 13)
         5' cgAgCuGgAcCaCuGgU 3',
``` and
a second stretch of contiguous nucleotides comprises the following nucleotide sequence:

```
                                          (SEQ ID NO: 7)
         5' GAcCaGuGgUcCaGcUcGu 3',
``` or
c) a first stretch of contiguous nucleotides comprises the following nucleotide sequence:

```
                                          (SEQ ID NO: 6)
         5' acGaGcUgGaCcAcUgGuC 3',
``` and
a second stretch of contiguous nucleotides comprises the following nucleotide sequence:

```
                                          (SEQ ID NO: 14)
         5' ACcAgUgGuCcAgCuCg 3',
``` or
d) a first stretch of contiguous nucleotides comprises the following nucleotide sequence:

```
                                          (SEQ IO NO: 13)
         5' cgAgCuGgAcCaCuGgU 3',
``` and
a second stretch of contiguous nucleotides comprises the following nucleotide sequence:

```
                                          (SEQ ID NO: 14)
         5' ACcAgUgGuCcAgCuCg 3',
``` wherein a minor nucleotide indicates that the nucleotide is 2'-F modified and an underlined nucleotide indicates that the nucleotide is 2'-O-methyl modified.

EMBODIMENT 82

The nucleic acid molecule of any one of embodiments 1 to 81, wherein the nucleic acid molecule consists of
a) a first stretch of contiguous nucleotides comprises the following nucleotide sequence:

```
                                          (SEQ ID NO: 6)
         5' acGaGcUgGaCcAcUgGuC 3',
``` and
a second stretch of contiguous nucleotides comprises the following nucleotide sequence:

```
                                          (SEQ ID NO: 7)
         5' GAcCaGuGgUcCaGcUcGu 3',
``` or
b) a first stretch of contiguous nucleotides comprises the following nucleotide sequence:

```
                                          (SEQ IO NO: 13)
         5' cgAgCuGgAcCaCuGgU 3',
``` and
a second stretch of contiguous nucleotides comprises the following nucleotide sequence:

```
                                          (SEQ ID NO: 7)
         5' GAcCaGuGgUcCaGcUcGu 3',
``` or
c) a first stretch of contiguous nucleotides comprises the following nucleotide sequence:

```
                                          (SEQ ID NO: 6)
         5' acGaGcUgGaCcAcUgGuC 3',
``` and
a second stretch of contiguous nucleotides comprises the following nucleotide sequence:

```
                                          (SEQ ID NO: 14)
         5' ACcAgUgGuCcAgCuCg 3',
``` or
d) a first stretch of contiguous nucleotides comprises the following nucleotide sequence:

```
                                          (SEQ IO NO: 13)
         5' cgAgCuGgAcCaCuGgU 3',
``` and
a second stretch of contiguous nucleotides comprises the following nucleotide sequence:

```
                                          (SEQ ID NO: 14)
         5' ACcAgUgGuCcAgCuCg 3',
``` wherein a minor nucleotide indicates that the nucleotide is 2'-F modified and an underlined nucleotide indicates that the nucleotide is 2'-O-methyl modified.

EMBODIMENT 83

The nucleic acid molecule of any one of embodiments 1 to 81, wherein the nucleic acid molecule consists of a
a) a first stretch of contiguous nucleotides comprises the following nucleotide sequence:

```
                                          (SEQ ID NO: 69)
         5' acGaGcUgGaCcAcUgGuCdTsdT 3',
``` and
a second stretch of contiguous nucleotides comprises the following nucleotide sequence:

```
                                          (SEQ ID NO: 70)
         5' GAcCaGuGgUcCaGcUcGudTsdT 3',
``` or
b) a first stretch of contiguous nucleotides comprises the following nucleotide sequence:

5' cgAgCuGgAcCaCuGgUdTsdT 3'    (SEQ ID NO: 71)

and
a second stretch of contiguous nucleotides comprises the following nucleotide sequence:

5' GAcCaGuGgUcCaGcUcGudTsdT 3'    (SEQ ID NO: 70)

or
c) a first stretch of contiguous nucleotides comprises the following nucleotide sequence:

5' acGaGcUgGaCcAcUgGuCdTsdT 3'    (SEQ ID NO: 69)

and
a second stretch of contiguous nucleotides comprises the following nucleotide sequence:

5' ACcAgUgGuCcAgCuCgdTsdT 3'    (SEQ ID NO: 72)

or
d) a first stretch of contiguous nucleotides comprises the following nucleotide sequence:

5' cgAgCuGgAcCaCuGgUdTsdT 3'    (SEQ ID NO: 71)

and
a second stretch of contiguous nucleotides comprises the following nucleotide sequence:

5' ACcAgUgGuCcAgCuCgdTsdT 3'    (SEQ ID NO: 72)

wherein a minor nucleotide indicates that the nucleotide is 2'-F modified and an underlined nucleotide indicates that the nucleotide is 2'-O-methyl modified and
wherein dTsdT indicates that at the 3' end a dinucleotide is attached consisting of two dTs, wherein said two dTs are covalently linked through a phosphorothioate bond.

EMBODIMENT 84

The nucleic acid molecule of any one of embodiments 1 to 83, for use in a method for the treatment and/or prevention of a disease.

EMBODIMENT 85

The nucleic acid molecule of embodiment 84, wherein the disease is a disease which can be treated by decreasing the expression of the Notch 1 gene and more specifically by decreasing the translation of the mRNA coding for Notch 1.

EMBODIMENT 86

The nucleic acid molecule of any one of embodiments 84 to 85, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

EMBODIMENT 87

The nucleic acid molecule of any one of embodiments 84 to 86, wherein the method comprises further the administration of a pharmaceutically active agent.

EMBODIMENT 88

The nucleic acid molecule of embodiment 87, wherein the pharmaceutically active agent is a cytostatic.

EMBODIMENT 89

The nucleic acid molecule of embodiment 88, wherein the pharmaceutically active agent is selected from the group comprising gemcitabine, docetaxel, cisplaint, oxaliplatin, 5-fluorouracil, irinotecan, paclitaxel, dexamethasone and temozolomide.

EMBODIMENT 90

The nucleic acid molecule of any one of embodiments 1 to 83, for use in a method for restoring drug sensitivity of cancer cells.

EMBODIMENT 91

The nucleic acid molecule of embodiment 90, wherein drug sensitivity is drug sensitivity mediated and/or involving NF-kappaB cascade.

EMBODIMENT 92

Use of a nucleic acid molecule of any one of embodiments 1 to 83, for the manufacture of a medicament for the treatment and/or prevention of a disease.

EMBODIMENT 93

Use of a embodiment 92, wherein the disease is a disease which can be treated by decreasing the expression of the Notch 1 gene and more specifically by decreasing the translation of the mRNA coding for Notch 1.

EMBODIMENT 94

Use of any one of embodiments 92 to 93, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

EMBODIMENT 95

Use of any one of embodiments 92 to 94, wherein the medicament is for administration together with a further pharmaceutically active agent.

EMBODIMENT 96

Use of embodiment 95, wherein the pharmaceutically active agent is a cytostatic.

EMBODIMENT 97

Use of embodiment 96, wherein the pharmaceutically active agent is selected from the group comprising gemcitabine, docetaxel, cisplaint, oxaliplatin, 5-fluorouracil, irinotecan, paclitaxel, dexamethasone and temozolomide.

EMBODIMENT 98

Use of a nucleic acid molecule of any one of embodiments 1 to 83, in the manufacture of an agent for restoring drug sensitivity of cancer cells.

EMBODIMENT 99

Use of embodiment 98, wherein drug sensitivity is drug sensitivity mediated and/or involving NF-kappaB cascade.

EMBODIMENT 100

A nanoemulsion comprising a discontinuous phase and a continuous aqueous phase and a nucleic acid molecule according to any one of embodiments 1 to 83.

EMBODIMENT 101

The nanoemulsion of embodiment 100, wherein the discontinuous phase comprises a perfluorocarbon phase.

EMBODIMENT 102

The nanoemulsion of any one of embodiments 1 to 101, wherein the nanoemulsion comprises an endocytosis enhancing surface, preferably the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

EMBODIMENT 103

The nanoemulsion of any one of embodiments 100 to 102, for use in the treatment and/or prevention of a disease.

EMBODIMENT 104

The nanoemulsion of any one of embodiments 100 to 102, for use in a method for restoring drug sensitivity of cancer cells.

EMBODIMENT 105

Use of a nanoemulsion of any one of embodiments 100 to 102, for the manufacture of a medicament for the treatment and/or prevention of a disease.

EMBODIMENT 106

Use of a nanoemulsion of any one of embodiments 100 to 102, in the manufacture of an agent for restoring drug sensitivity of cancer cells.

EMBODIMENT 107

A pharmaceutical composition comprising a nucleic acid molecule of any one of embodiments 1 to 83 and/or a nanoemulsion of any one of embodiments 100 to 102, and a pharmaceutically acceptable excipient.

EMBODIMENT 108

The pharmaceutical composition of embodiment 107, for use in the treatment and/or prevention of a disease.

EMBODIMENT 109

The pharmaceutical composition of embodiment 107, for use in a method for restoring drug sensitivity of cancer cells.

EMBODIMENT 110

A method for the treatment and/or prevention of a disease, wherein the method comprises the administration to a subject of a nucleic acid of any one of embodiments 1 to 83, a nanoemulsion of any one of embodiments 100 to 102, and/or a pharmaceutical composition of embodiment 107.

EMBODIMENT 111

A method for restoring drug sensitivity of cancer cells, wherein the method comprises the administration to a subject of a nucleic acid of any one of embodiments 1 to 83, a nanoemulsion of any one of embodiments 100 to 102, and/or a pharmaceutical composition of embodiment 107, wherein the subject is suffering from cancer and cells of the cancer are drug-resistant.

The present inventors have surprisingly found that a nucleic acid molecule comprising a double-stranded structure, wherein the double-stranded structure is formed by a first strand and a second strand, wherein the first strand comprises a first stretch of contiguous nucleotides and the second strand comprises a second stretch of contiguous nucleotides, wherein the first stretch of contiguous nucleotides comprises a) a nucleotide sequence, wherein the nucleotide sequence is at least 63% identical to

```
        (i) nucleotide sequence
                                      (SEQ ID NO: 1)
        5' ACGAGCUGGACCACUGGUC 3'
        or
        (ii) nucleotide sequence
                                      (SEQ ID NO: 8)
        5' CGAGCUGGACCACUGGU 3';
``` or b) a nucleotide sequence, wherein the nucleotide sequence comprises at least a stretch of 8 or 9 nucleotides of

```
(i) nucleotide sequence
                                    (SEQ ID NO: 1)
5' ACGAGCUGGACCACUGGUC 3'
or (ii) nucleotide sequence
                                    (SEQ ID NO: 8)
5' CGAGCUGGACCACUGGU 3'
``` is capable of causing post-transcriptional silencing of a gene and RNA interference in particular. This nucleic acid, including all of its embodiments, will be referred to herein as the nucleic acid molecule of the invention.

It is within the invention that the nucleic acid molecule of the invention is a small interfering RNA (siRNA). Such siRNA is a particularly preferred embodiment of the nucleic acid molecule of the invention. In an embodiment the siRNA is directed to an expressed RNA transcript of Notch 1 (sometimes referred to as a "target nucleic acid" herein). As preferably used herein, the terms "silence" and "knockdown" when referring to gene expression means a reduction in gene expression. The present invention further relates to processes for making the nucleic acid molecule of the invention.

In an embodiment of the invention, the target nucleic acid is an RNA expressed from a mammalian Notch 1 gene. In one embodiment, the target nucleic acid is an RNA expressed from mouse Notch 1. In another embodiment, the target nucleic acid is an RNA expressed from human Notch 1. In another embodiment, the target nucleic acid is a human Notch 1 mRNA. In another embodiment, the target nucleic acid is a human Notch 1 hnRNA. In another embodiment, the target nucleic acid is an mRNA comprising the sequence of SEQ ID NO: 12.

In an embodiment of the present invention the nucleic acid molecule is not forming a double-stranded structure. In such embodiment the nucleic acid molecule is either formed by two separate single strands which may be present individually, i.e. in a non-hybridized state so that the double-stranded structure is not formed, or in a hybridized form where a double-stranded structure is formed which is different from the double-stranded structure which is required so as to mediate or trigger RNA interference. Alternatively, the nucleic acid molecule forming the double-stranded structure is a single strand nucleic acid molecule, wherein the nucleic acid molecule is not folding back on itself such that the double-stranded structure is formed or such that a double-stranded structure is formed which is different from the double-stranded structure which is required so as to mediate or trigger RNA interference.

In a more preferred embodiment the double-stranded structure is formed under in vivo conditions, and more specifically upon administration of the nucleic acid molecule to a subject, preferably a mammal or mammalian cell.

The siRNA of the present invention are suitable to inhibit the expression of Notch 1. The siRNA according to the present invention is, thus, suitable to trigger the RNA interference response resulting in the reduction of the Notch 1 mRNA in a mammalian cell. The siRNA according to the present invention are further suitable to decrease the expression of Notch 1 protein by decreasing gene expression at the level of mRNA.

siRNA Design:

An siRNA of the present invention comprises two strands of a nucleic acid, a first strand, which is also referred to as antisense strand, comprising a first stretch of contiguous nucleotides, which is also referred to as antisense stretch, and a second strand, which is also referred to as sense strand, comprising a second stretch of contiguous nucleotides which is also referred to as sense stretch. The nucleic acid normally consists of ribonucleotides or modified ribonucleotides however; the nucleic acid may comprise deoxynucleotides (DNA) as described herein. The siRNA further comprises a double-stranded nucleic acid portion or duplex region formed by all or a portion of the antisense strand or the antisense stretch and all or a portion of the sense strand or the sense stretch. Such double-stranded nucleic acid portion or duplex region is herein also referred to as double-stranded structure. The portion of the antisense strand or of the antisense stretch forming the duplex region with the sense strand or with the antisense stretch is the antisense strand duplex region or the antisense stretch region or simply, the antisense duplex region, and the portion of the sense strand or of the sense stretch forming the duplex region with the antisense strand or the antisense stretch is the sense strand duplex region is the sense stretch duplex region or simply, the sense duplex region. The duplex region is defined as beginning with the first base pair formed between the antisense strand or the antisense stretch and the sense strand of the sense stretch and ending with the last base pair formed between the antisense strand or the antisense stretch and the sense strand or the sense stretch, inclusive. The portion of the siRNA on either side of the duplex region is the flanking regions. The portion of the antisense strand or of the antisense stretch on either side of the antisense duplex region is the antisense flanking regions. The portion of the antisense strand or antisense stretch 5' to the antisense duplex region is the antisense 5' flanking region. The portion of the antisense strand or antisense stretch 5' to the antisense duplex region is the antisense 3' flanking region. The portion of the sense strand or of the sense stretch on either side of the sense duplex region is the sense flanking regions. The portion of the sense strand or of the sense stretch 5' to the sense duplex region is the sense 5' flanking region. The portion of the sense strand 5' or of the sense stretch to the sense duplex region is the sense 3' flanking region.

Identity:

In an embodiment, identity of one nucleotide sequence to another nucleotide sequence is an indication of how many nucleotides are shared between both the one nucleotide sequence and the another nucleotide sequence. Identity is expresses as the ratio of the number of nucleotides of the one sequence shared with the another nucleotide sequence to the total number of nucleotides of the another nucleotide sequence. The maximum value of identity is 100%. It will be acknowledged by a person skilled in the art that depending on the length of the one nucleotide sequence and of the another nucleotide sequence on the one hand and the number of nucleotides shared between the one nucleotide sequence and the another nucleotide sequence identity is not always an integer. If such calculated ratio is not an integer, the identity is nevertheless preferably indicated as the integer which gets as close as possible to the calculated ratio and which makes technically sense. According to the present invention, the identity may be 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

Complementarity:

According to the invention, the antisense duplex region and the sense duplex region may be fully complementary and are at least partially complementary to each other. Such complementarity is based on Watson-Crick base pairing (i.e., A:U and G:C base pairing). Depending on the length of a nucleic acid molecule of the invention and an siRNA in particular a perfect match in terms of base complementarity between the antisense and sense duplex regions is not necessarily required however, the antisense and sense strands must be able to hybridize under physiological conditions.

In one embodiment, the complementarity between the antisense strand and sense strand is perfect, i.e. no nucleotide mismatches or additional/deleted nucleotides in either strand.

In one embodiment, the complementarity between the antisense stretch and sense stretch is perfect, i.e. no nucleotide mismatches or additional/deleted nucleotides in either stretch.

In one embodiment, the complementarity between the antisense duplex region and sense duplex region is perfect, i.e. no nucleotide mismatches or additional/deleted nucleotides in the duplex region of either strand.

In another embodiment, the complementarity between the antisense duplex region and the sense duplex region is not perfect. In one embodiment, the identity between the antisense duplex region and the complementary sequence of the sense duplex region is selected from the group consisting of at least 75%, 80%, 85%, 90% and 95%; wherein a siRNA comprising the antisense duplex region and the sense duplex region is suitable for reducing expression of Notch 1. In another embodiment, the siRNA, wherein the identity between the antisense duplex region and complementary sequence of the sense duplex region is selected from the group consisting of at least 75%, 80%, 85%, 90% and 95%, is able to reduce expression of Notch 1 by at least 25%, 50% or 75% of a comparative siRNA having a duplex region with perfect identity between the antisense duplex region and the sense duplex region. As used herein the term "comparative siRNA" is a siRNA that is identical to the siRNA to which it is being compared, except for the specified difference, and which is tested under identical conditions.

RNAi using siRNA involves the formation of a duplex region between all or a portion of the antisense strand or antisense stretch and a portion of the target nucleic acid. The portion of the target nucleic acid that forms a duplex region with the antisense strand or antisense stretch, defined as beginning with the first base pair formed between the antisense strand or antisense stretch and the target sequence and ending with the last base pair formed between the antisense strand or antisense stretch and the target sequence, inclusive, is the target nucleic acid sequence or simply, target sequence. The duplex region formed between the antisense strand or antisense stretch and the sense strand or sense stretch may, but need not be the same as the duplex region formed between the antisense strand or antisense stretch and the target sequence. That is, the sense strand or sense stretch may have a sequence different from the target sequence however; the antisense strand or antisense stretch must be able to form a duplex structure with both the sense strand or sense stretch and the target sequence.

In one embodiment, the complementarity between the antisense strand or antisense stretch and the target sequence is perfect, i.e. no nucleotide mismatches or additional/deleted nucleotides in either nucleic acid.

In one embodiment, the complementarity between the antisense duplex region, i.e. the portion of the antisense strand or antisense stretch forming a duplex region with the sense strand or sense stretch, and the target sequence is perfect, i.e. no nucleotide mismatches or additional/deleted nucleotides in either nucleic acid.

In another embodiment, the complementarity between the antisense duplex region and the target sequence is not perfect. In one embodiment, the identity between the antisense duplex region and the complementary sequence of the target sequence is selected from the group consisting of at least 75%, 80%, 85%, 90% or 95%, wherein a siRNA comprising the antisense duplex region is suitable for reducing expression of Notch 1. In another embodiment, the siRNA, wherein the identity between the antisense duplex region and complementary sequence of the target sequence is selected from the group consisting of at least 75%, 80%, 85%, 90% and 95%, is able to reduce expression of Notch 1 by at least 25%, 50% or 75% of a comparative siRNA with perfect identity to the antisense strand or the antisense stretch and target sequence.

In another embodiment, the siRNA of the invention comprises a duplex region wherein the antisense duplex region has a number of nucleotides selected from the group consisting of 1, 2, 3, 4 and 5 that are not base-paired to a nucleotide in the sense duplex region, and wherein said siRNA is suitable for reducing expression of Notch 1. Lack of base-pairing is due to either lack of complementarity between bases, i.e., no Watson-Crick base pairing, or because there is no corresponding nucleotide on either the antisense duplex region or the sense duplex region such that a bulge is created. In one embodiment, a siRNA comprising an antisense duplex region having a number of nucleotides selected from the group consisting of 1, 2, 3, 4 and 5 that are not base-paired to the sense duplex region, is able to reduce expression of Notch 1 by at least 25%, 50%, 75% of a comparative siRNA wherein all nucleotides of said antisense duplex region are base paired with all nucleotides of said sense duplex region.

In another embodiment, the antisense strand or the antisense stretch has a number of nucleotides selected from 1, 2, 3, 4, 5, 6, 7, 8, 9 or 10 that do not base-pair to the sense strand or the sense stretch, and wherein a siRNA comprising said antisense strand is suitable for reducing expression of Notch 1. Lack of complementarity is due to either lack of complementarity between bases or because there is no corresponding nucleotide on either the antisense strand, or the antisense stretch, or the sense strand, or the sense stretch. The lack of a corresponding nucleotide results in either a single-stranded overhang or a bulge (if in the duplex region), in either the antisense strand, or the antisense stretch, or the sense strand, or the sense stretch. In one embodiment, a siRNA comprising an antisense strand or an antisense stretch having a number of nucleotides selected from 1, 2, 3, 4, 5, 6, 7, 8, 9 or 10 that do not base pair to the sense strand or the sense stretch, is able to reduce expression of Notch 1 by at least 25%, 50%, 75% of a comparative siRNA wherein all nucleotides of said antisense strand or said antisense stretch are complementary to all nucleotides of the sense strand of the sense stretch. In one embodiment, a siRNA comprising an antisense strand or an antisense stretch having a number of nucleotides selected from 1, 2, 3, 4, 5, 6, 7, 8, 9 or 10 that are mismatched to the target sequence, is able to reduce expression of Notch 1 by at least 25%, 50%, 75% of a comparative siRNA wherein all nucleotides of said antisense strand or said antisense strand are complementary to all nucleotides of said sense strand or said sense stretch. In another embodiment, all of the mismatched nucleotides are outside the duplex region.

In another embodiment, the antisense duplex region has a number of nucleotides selected from 1, 2, 3, 4 or 5 that do not base-pair to the sense duplex region, and wherein a siRNA comprising said antisense duplex region is suitable for reducing expression of Notch 1. Lack of complementarity is due to either lack of complementarity between bases or because there is no corresponding nucleotide on either the antisense duplex region or the sense duplex region such that a bulge in created in either the antisense duplex region or the sense duplex region. In one embodiment, a siRNA comprising an antisense duplex region having a number of nucleotides selected from the group consisting of 1, 2, 3, 4 and 5 that do not base pair to the sense duplex region, is able to reduce expression of Notch 1 by at least 25%, 50%, 75% of a comparative siRNA wherein all nucleotides of said antisense duplex region are complementary to all of the nucleotides of said sense duplex region.

In another embodiment, the antisense strand has a number of nucleotides selected from 1, 2, 3, 4, 5, 6, 7, 8, 9 or 10 that do not base-pair to the target sequence, and wherein a siRNA comprising said antisense strand is suitable for reducing expression of Notch 1. Lack of complementarity is due to either lack of complementarity between bases or because there is no corresponding nucleotide on either the antisense strand, or the antisense stretch, or the target sequence. The lack of a corresponding nucleotide results in a bulge in either the antisense strand, or the antisense stretch, or the target sequence. In one embodiment, a siRNA comprising an antisense strand or an antisense stretch having a number of nucleotides selected from 1, 2, 3, 4, 5, 6, 7, 8, 9 or 10 do not base pair to the target sequence, is able to reduce expression of Notch 1 by at least 25%, 50%, 75% of a comparative siRNA wherein all nucleotides of said antisense strand or antisense stretch are complementary to all nucleotides of said target sequence. In one embodiment, a siRNA comprising an antisense strand or an antisense stretch having a number of nucleotides selected from 1, 2, 3, 4, 5, 6, 7, 8, 9 or 10 that are mismatched to the target sequence, is able to reduce expression of Notch 1 by at least 25%, 50% or 75% of a comparative siRNA wherein all nucleotides of said antisense strand or of said antisense stretch are complementary to all nucleotides of said target sequence.

In another embodiment, the complementarity between an antisense duplex region and both a sense duplex region and a target sequence of an siRNA is such that the antisense duplex region and the sense duplex region or the target sequence hybridize to one another under physiological conditions (37° C. in a physiological buffer) and the siRNA is suitable for reducing expression of Notch 1. In one embodiment, the siRNA comprising an antisense duplex region that hybridizes to a sense duplex region and a target sequence under physiological conditions, is able to reduce expression of Notch 1 by at least 25%, 50%, 75% of a comparative siRNA with perfect complementarity between the antisense strand or the antisense stretch and target sequence.

In another aspect, the complementarity between an antisense duplex region and a sense duplex region of a siRNA is such that the antisense duplex region and sense duplex region hybridize under the following conditions: 400 mM NaCl, 40 mM PIPES pH 6.4, 1 mM EDTA, 70° C., and is suitable for reducing expression of Notch 1. In one embodiment, the siRNA comprising an antisense duplex region and a sense duplex region that hybridize to one another under the conditions 400 mM NaCl, 40 mM PIPES pH 6.4, 1 mM EDTA, 70° C., is able to reduce expression of Notch 1 by at least 25%, 50%, 75% of a comparative siRNA with perfect complementarity between the antisense duplex region and sense duplex region.

In another embodiment, the complementarity between an antisense strand or an antisense stretch of a siRNA and a target sequence is such that the antisense strand or antisense stretch and target sequence hybridize under the following conditions: 400 mM NaCl, 40 mM PIPES pH 6.4, 1 mM EDTA, 70° C. and wherein the siRNA is suitable for reducing expression of Notch 1. In one embodiment, the siRNA comprising an antisense strand or an antisense stretch that hybridizes to the target sequence under the following conditions: 400 mM NaCl, 40 mM PIPES pH 6.4, 1 mM EDTA, 70° C., is able to reduce expression of Notch 1 by at least 25%, 50%, 75% of a comparative siRNA with perfect complementarity between the antisense strand or the antisense stretch and the target sequence.

Length:

RNA interference is observed using long nucleic acid molecules comprising several dozen or hundreds of base pairs, although shorter RNAi molecules are generally preferred.

In one embodiment, the length of the siRNA duplex region is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 base pairs. In one embodiment, the length of the siRNA duplex region is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 consecutive base pairs. In another embodiment, the length of the siRNA duplex region is selected from the group consisting of 16, 17, 18, 19, 20, 21, 22, 23, 24, 25, 26, 27, 28, 29, 30, 31, 32, 33, 34 and 35 base pairs. In another embodiment, the length of the siRNA duplex region is selected from the group consisting of 16, 17, 18, 19, 20, 21, 22, 23, 24, 25, 26, 27, 28, 29, 30, 31, 32, 33, 34 and 35 consecutive base pairs.

In one embodiment, the length of the antisense strand is selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense stand is selected from the group consisting of 16, 17, 18, 19, 20, 21, 22, 23, 24, 25, 26, 27, 28, 29, 30, 31, 32, 33, 34 and 35 nucleotides.

In one embodiment, the length of the antisense stretch is selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense stretch is selected from the group consisting of 13, 14, 15, 16, 17, 18, 19, 20, 21, 22, 23, 24, 25, 26, 27, 28, 29, 30, 31, 32, 33, 34 and 35 nucleotides.

In one embodiment, the length of the sense strand is selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the sense stand is selected from the group consisting of 13, 14, 15, 16, 17, 18, 19, 20, 21, 22, 23, 24, 25, 26, 27, 28, 29, 30, 31, 32, 33, 34 and 35 nucleotides.

In one embodiment, the length of the sense stretch is selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the sense stretch is selected from the group consisting of 13, 14, 15, 16, 17, 18, 19, 20, 21, 22, 23, 24, 25, 26, 27, 28, 29, 30, 31, 32, 33, 34 and 35 nucleotides.

In one embodiment, the length of the antisense strand and the length of the sense strand are independently selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense strand and the length of the sense stand are independently selected from the group consisting of 13, 14, 15, 16, 17, 18, 19, 20, 21, 22, 23, 24, 25, 26, 27, 28, 29, 30, 31, 32, 33, 34 and 35 nucleotides. In one embodiment, the antisense strand and the sense strand are equal in length. In another embodiment, the antisense strand and the sense stand are equal in length, wherein the length is selected from the group consisting of 13, 14, 15, 16, 17, 18, 19, 20, 21, 22, 23, 24, 25, 26, 27, 28, 29, 30, 31, 32, 33, 34 and 35 nucleotides.

In one embodiment, the length of the antisense stretch and the length of the sense stretch are independently selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense stretch and the length of the sense stretch are independently selected from the group consisting of 13, 14, 15, 16, 17, 18, 19, 20, 21, 22, 23, 24, 25, 26, 27, 28, 29, 30, 31, 32, 33, 34 and 35 nucleotides. In one embodiment, the antisense stretch and the sense stretch are equal in length. In another embodiment, the antisense stretch and the sense stretch are equal in length, wherein the length is selected from the group consisting of 13, 14, 15, 16, 17, 18, 19, 20, 21, 22, 23, 24, 25, 26, 27, 28, 29, 30, 31, 32, 33, 34 and 35 nucleotides.

In one embodiment, the length of the antisense strand or the antisense stretch is selected from the group consisting of about 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand or antisense stretch comprises the nucleotide sequence of SEQ ID NO: 8 or 1.

In one embodiment, the length of the antisense strand or the antisense stretch is selected from the group consisting of about 17, 18, 19, 20, 21, 22, 23, 24, 25, 26, 27, 28, 29, 30, 31, 32, 33, 34 and 35 nucleotides, wherein the antisense strand or the antisense stretch comprises the nucleotide sequence of SEQ ID NOs: 8 or 1.

In one embodiment, the length of the sense strand or the sense stretch is selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the sense strand or the sense stretch comprises the nucleotide sequence of SEQ ID NOs: 9 or 3.

In one embodiment, the length of the sense strand or of the sense stretch is selected from the group consisting of about 17, 18, 19, 20, 21, 22, 23, 24, 25, 26, 27, 28, 29, 30, 31, 32, 33, 34 and 35 nucleotides, wherein the sense strand comprises the nucleotide sequence of SEQ ID NOs: 9 or 3.

In one embodiment, the length of the antisense strand or of the antisense stretch and the length of the sense strand or the sense stretch are independently selected from the group consisting of about 13 to 35, 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand or antisense stretch comprises the nucleotide sequence of SEQ ID NO. NOs: 8 or 1, and wherein the sense strand or the sense stretch comprises the nucleotide sequence of SEQ ID NOs: 9 or 3.

In one embodiment, the length of the antisense strand and the length of the sense stand are independently selected from the group consisting of 17, 18, 19, 20, 21, 22, 23, 24, 25, 26, 27, 28, 29, 30, 31, 32, 33, 34 and 35 nucleotides, wherein the antisense strand comprises the nucleotide sequence of SEQ ID NO. NOs: 8 or 1, and wherein the sense strand comprises the nucleotide sequence of SEQ ID NOs: 9 or 3.

In one embodiment, the length of the antisense stretch and the length of the sense stretch and are independently selected from the group consisting of 17, 18, 19, 20, 21, 22, 23, 24, 25, 26, 27, 28, 29, 30, 31, 32, 33, 34 and 35 nucleotides, wherein the antisense stretch comprises the nucleotide sequence of SEQ ID NO. NOs: 8 or 1, and wherein the sense stretch comprises the nucleotide sequence of SEQ ID NOs: 9 or 3.

In one embodiment, the antisense strand and the sense strand are equal in length, wherein the antisense strand comprises the nucleotide sequence of SEQ ID NO. NOs: 8 or 1, and wherein the sense strand comprises the nucleotide sequence of SEQ ID NOs: 9 or 3.

In one embodiment, the antisense stretch and the sense stretch are equal in length, wherein the antisense stretch comprises the nucleotide sequence of SEQ ID NO. NOs: 8 or 1, and wherein the sense stretch comprises the nucleotide sequence of SEQ ID NOs: 9 or 3.

In another embodiment, the antisense strand and the sense stand are equal in length, wherein the length is selected from the group consisting of 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand comprises the nucleotide sequence of SEQ ID NO. NOs: 8 or 1, and wherein the sense strand comprises the nucleotide sequence of SEQ ID NOs: 9 or 3.

In another embodiment, the antisense stretch and the sense stretch are equal in length, wherein the length is selected from the group consisting of 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense stretch comprises the nucleotide sequence of SEQ ID NO. NOs: 8 or 1, and wherein the sense stretch comprises the nucleotide sequence of SEQ ID NOs: 9 or 3.

In another embodiment, the antisense strand and the sense stand are equal in length, wherein the length is selected from the group consisting of 17, 18, 19, 20, 21, 22, 23, 24, 25, 26, 27, 28, 29, 30, 31, 32, 33, 34 and 35 nucleotides, wherein the antisense strand comprises the nucleotide sequence of SEQ ID NO. NOs: 8 or 1, and wherein the sense strand comprises the nucleotide sequence of SEQ ID NOs: 9 or 3.

In another embodiment, the antisense stretch and the sense stretch are equal in length, wherein the length is selected from the group consisting of 17, 18, 19, 20, 21, 22, 23, 24, 25, 26, 27, 28, 29, 30, 31, 32, 33, 34 and 35 nucleotides, wherein the antisense stretch comprises the nucleotide sequence of SEQ ID NO. NOs: 8 or 1, and wherein the sense stretch comprises the nucleotide sequence of SEQ ID NOs: 9 or 3.

Certain embodiments provide for antisense and sense strand combinations (identified by SEQ ID NO:): 8 and 9; 1 and 3; 4 and 5; 6 and 7; and 10 and 11.

Certain embodiments provide for antisense and sense stretch combinations (identified by SEQ ID NO:): 8 and 9; 1 and 3; 4 and 5; 6 and 7; and 10 and 11.

Ends (Overhangs and Blunt Ends):

The siRNA of the present invention may comprise an overhang or be blunt ended. An "overhang" as used herein has its normal and customary meaning in the art, i.e., a single stranded portion of a nucleic acid that extends beyond the terminal nucleotide of a complementary strand or stretch in a double strand nucleic acid. The term "blunt end" includes double stranded nucleic acid whereby both strands or stretches terminate at the same position, regardless of whether the terminal nucleotide(s) are base paired. In one embodiment, the terminal nucleotide of an antisense strand or antisense stretch and a sense strand or a sense stretch at a blunt end are base paired. In another embodiment, the terminal nucleotide of an antisense strand or an antisense stretch and a sense strand or a sense stretch at a blunt end are not paired. In another embodiment, the terminal two nucleotides of an antisense strand or an antisense stretch and a sense strand or sense stretch at a blunt end are base paired. In another embodiment, the terminal two nucleotides of a antisense strand or an antisense stretch and a sense strand or sense stretch at a blunt end are not paired.

In one embodiment, the siRNA has an overhang at one end and a blunt end at the other. In another embodiment, the siRNA has an overhang at both ends. In another embodiment, the siRNA is blunt ended at both ends. In one embodiment, the siRNA is blunt ended at one end. In another embodiment, the siRNA is blunt ended at the end with the 5'-end of the antisense strand or of the antisense stretch and the 3'-end of the sense strand or of the sense stretch. In another embodiment, the siRNA is blunt ended at the end with the 3'-end of the antisense strand or of the antisense stretch and the 5'-end of the sense strand or of the sense stretch. In another embodiment, the siRNA is blunt ended at both ends.

In another embodiment, the siRNA comprises a overhang at a 3'- or 5'-end. In one embodiment, the siRNA has a 3'-overhang on the antisense strand or on the antisense stretch. In another embodiment, the siRNA has a 3'-overhang on the sense strand or on the sense stretch. In another embodiment, the siRNA has a 5'-overhang on the antisense strand of the antisense stretch. In another embodiment, the siRNA has a 5'-overhang on the sense strand or at the sense stretch. In another embodiment, the siRNA has an overhang at both the 5'-end and 3'-end of the antisense stand or of the antisense stretch. In another embodiment, the siRNA has an overhang at both the 5'-end and 3'-end of the sense stand or of the sense stretch. In another embodiment, the siRNA has a 5' overhang on the antisense stand or on the antisense stretch and a 3' overhang on the sense strand or on the sense stretch. In another embodiment, the siRNA has a 3' overhang on the antisense stand or on the antisense stretch and a 5' overhang on the sense strand or on the sense stretch. In another embodiment, the siRNA has a 3' overhang on the antisense stand or on the antisense stretch and a 3' overhang on the sense strand or on the sense stretch. In another embodiment, the siRNA has a 5' overhang on the antisense stand or on the antisense stretch and a 5' overhang on the sense strand or on the sense strand.

In one embodiment, the overhang at the 3'-end of the antisense strand or of the antisense stretch has a length selected from the group consisting of 1, 2, 3, 4 and 5 nucleotides. In one embodiment, the overhang at the 3'-end of the sense strand or of the sense stretch has a length selected from the group consisting of 1, 2, 3, 4 and 5 nucleotides. In one embodiment, the overhang at the 5'-end of the antisense strand or of the antisense stretch has a length selected from the group consisting of 1, 2, 3, 4 and 5 nucleotides. In one embodiment, the overhang at the 5'-end of the sense strand or of the sense stretch has a length selected from the group consisting of 1, 2, 3, 4 and 5 nucleotides.

Modification:

Another aspect relates to modifications of the siRNA and, in accordance therewith, the nucleic acid molecule of the invention may be modified as outlined in the following. It is within the present invention that each and any modification and pattern disclosed herein, and any disclosure herein related to such modification and pattern, in particular referring to siRNA may also be applicable to and thus realized in connection with and on a nucleic acid molecule of the invention. It is also within the present invention that to the extent it is referred to an antisense strand and/or a sense strand, particularly when it comes to the modification of the antisense strand and/or a sense strand and the nucleotides forming such antisense strand and/or sense strand, such disclosure equally applies to an antisense stretch and/or sense stretch, particularly when it comes to the modification of the antisense stretch and/or a sense stretch and the nucleotides forming such antisense stretch and/or sense stretch.

siRNA according to the invention are a ribonucleic acid or a modified ribonucleic acid. Chemical modifications of the siRNA of the present invention provides a powerful tool in overcoming potential limitations including, but not limited to, in vitro and in vivo stability and bioavailability inherent to native RNA molecules. Chemically-modified siRNA can also minimize the possibility of activating interferon activity in humans. Chemical modification can further enhance the functional delivery of a siRNA to a target cell. The modified siRNA of the present invention may comprise one or more chemically modified ribonucleotides of either or both of the antisense strand or the sense strand. A ribonucleotide may comprise a chemical modification of the base, sugar or phosphate moieties.

Modifications to Base Moiety:

A secondary aspect relates to modifications to a base moiety. One or more nucleotides of a siRNA of the present invention may comprise a modified base. A "modified base" means a nucleotide base other than an adenine, guanine, cytosine or uracil at the 1' position.

In one aspect, the siRNA comprises at least one nucleotide comprising a modified base. In one embodiment, the modified base in on the antisense strand. In another embodiment, the modified base in on the sense strand. In another embodiment, the modified base is in the duplex region. In another embodiment, the modified base is outside the duplex region, i.e., in a single stranded region. In another embodiment, the modified base is on the antisense strand and is outside the duplex region. In another embodiment, the modified base is on the sense strand and is outside the duplex region. In another embodiment, the 3'-terminal nucleotide of the antisense strand is a nucleotide with a modified base. In another embodiment, the 3'-terminal nucleotide of the sense strand is nucleotide with a modified base. In another embodiment, the 5'-terminal nucleotide of the antisense strand is nucleotide with a modified base. In another embodiment, the 5'-terminal nucleotide of the sense strand is nucleotide with a modified base.

In one embodiment, a siRNA has 1 modified base. In another embodiment, a siRNA has about 2-4 modified bases. In another embodiment, a siRNA has about 4-6 modified bases. In another embodiment, a siRNA has about 6-8 modified bases. In another embodiment, a siRNA has about 8-10 modified bases. In another embodiment, a siRNA has about 10-12 modified bases. In another embodiment, a siRNA has about 12-14 modified bases. In another embodiment, a siRNA has about 14-16 modified bases. In another embodiment, a siRNA has about 16-18 modified bases. In another embodiment, a siRNA has about 18-20 modified bases. In another embodiment, a siRNA has about 20-22 modified bases. In another embodiment, a siRNA has about 22-24 modified bases. In another embodiment, a siRNA has about 24-26 modified bases. In another embodiment, a siRNA has about 26-28 modified bases. In each case the siRNA comprising said modified bases retains at least 50% of its activity as compared to the same siRNA but without said modified bases.

In one embodiment, the modified base is a purine. In another embodiment, the modified base is a pyrimidine. In another embodiment, at least half of the purines are modified. In another embodiment, at least half of the pyrimidines are modified. In another embodiment, all of the purines are modified. In another embodiment, all of the pyrimidines are modified.

In another embodiment, the siRNA comprises a nucleotide comprising a modified base, wherein the base is selected from the group consisting of 2-aminoadenosine, 2,6-diaminopurine, inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

In another aspect, a siRNA of the present invention comprises an abasic nucleotide. The term "abasic" as used herein, refers to moieties lacking a base or having other chemical groups in place of a base at the 1' position, for example a 3',3'-linked or 5',5'-linked deoxyabasic ribose derivative. As used herein, a nucleotide with a modified base does not include abasic nucleotides. In one aspect, the siRNA comprises at least one abasic nucleotide. In one embodiment, the abasic nucleotide is on the antisense strand. In another embodiment, the abasic nucleotide is on the sense strand. In another embodiment, the abasic nucleotide is in the duplex region. In another embodiment, the abasic nucleotide is outside the duplex region. In another embodiment, the abasic nucleotide is on the antisense strand and is outside the duplex region. In another embodiment, the abasic nucleotide is on the sense strand and is outside the duplex region. In another embodiment, the 3'-terminal nucleotide of the antisense strand is an abasic nucleotide. In another embodiment, the 3'-terminal nucleotide of the sense strand is an abasic nucleotide. In another embodiment, the 5'-terminal nucleotide of the antisense strand is an abasic nucleotide. In another embodiment, the 5'-terminal nucleotide of the sense strand is an abasic nucleotide. In another embodiment, a siRNA has a number of abasic nucleotides selected from the group consisting of 1, 2, 3, 4, 5 and 6.

Modifications to Sugar Moiety:

Another secondary aspect relates to modifications to a sugar moiety. One or more nucleotides of an siRNA of the present invention may comprise a modified ribose moiety.

Modifications at the 2'-position wherein the 2'-OH is substituted include the non-limiting examples selected from the group consisting of alkyl, substituted alkyl, alkaryl-, aralkyl-, —F, —Cl, —Br, —CN, –CF3, —OCF3, —OCN, —O-alkyl, —S-alkyl, HS-alkyl-O, —O-alkenyl, —S-alkenyl, —N-alkenyl, —SO-alkyl, -alkyl-OSH, -alkyl-OH, —O-alkyl-OH, —O-alkyl-SH, —S-alkyl-OH, —S— alkyl-SH, -alkyl-S-alkyl, -alkyl-O-alkyl, —ONO2, —NO2, —N3, —NH2, alkylamino, dialkylamino-, aminoalkyl-, aminoalkoxy, aminoacid, aminoacyl-, —ONH2, —O-aminoalkyl, —O-aminoacid, —O-aminoacyl, heterocycloalkyl-, heterocycloalkaryl-, aminoalkylamino-, polyalklylamino-, substituted silyl-, methoxyethyl-(MOE), alkenyl and alkynyl. "Locked" nucleic acids (LNA) in which the 2' hydroxyl is connected, e.g., by a methylene bridge, to the 4' carbon of the same ribose sugar is further included as a 2' modification of the present invention. Preferred substitutents are 2'-methoxyethyl, 2'-OCH3, 2'-O-allyl, 2'-C-allyl, and 2'-fluoro.

In one embodiment, the siRNA comprises 1-5 2'-modified nucleotides. In another embodiment, the siRNA comprises 5-10 2'-modified nucleotides. In another embodiment, the siRNA comprises 15-20 2'-modified nucleotides. In another embodiment, the siRNA comprises 20-25 2'-modified nucleotides. In another embodiment, the siRNA comprises 25-30 2'-modified nucleotides.

In one embodiment, the antisense strand comprises 1-2 2'-modified nucleotides. In one embodiment, the antisense strand comprises about 2-4 2'-modified nucleotides. In one embodiment, the antisense strand comprises about 4-6 2'-modified nucleotides. In one embodiment, the antisense strand comprises about 6-8 2'-modified nucleotides. In one embodiment, the antisense strand comprises about 8-10 2'-modified nucleotides. In one embodiment, the antisense strand comprises about 10-12 2'-modified nucleotides. In one embodiment, the antisense strand comprises about 12-14 2'-modified nucleotides. In one embodiment, the antisense strand comprises about 14-16 2'-modified nucleotides. In one embodiment, the antisense strand comprises about 16-18 2'-modified nucleotides. In one embodiment, the antisense strand comprises about 18-20 2'-modified nucleotides. In one embodiment, the antisense strand comprises about 22-24 2'-modified nucleotides. In one embodiment, the antisense strand comprises about 24-26 2'-modified nucleotides.

In one embodiment, the sense strand comprises 1-2 2'-modified nucleotides. In one embodiment, the sense strand comprises about 2-4 2'-modified nucleotides. In one embodiment, the sense strand comprises about 4-6 2'-modified nucleotides. In one embodiment, the sense strand comprises about 6-8 2'-modified nucleotides. In one embodiment, the sense strand comprises about 8-10 2'-modified nucleotides. In one embodiment, the sense strand comprises about 10-12 2'-modified nucleotides. In one embodiment, the sense strand comprises about 12-14 2'-modified nucleotides. In one embodiment, the sense strand comprises about 14-16 2'-modified nucleotides. In one embodiment, the sense strand comprises about 16-18 2'-modified nucleotides. In one embodiment, the sense strand comprises about 18-20 2'-modified nucleotides. In one embodiment, the sense strand comprises about 22-24 2'-modified nucleotides. In one embodiment, the sense strand comprises about 24-26 2'-modified nucleotides.

In one embodiment, the siRNA comprises 1-5 2'-OCH3 modified nucleotides. In another embodiment, the siRNA comprises 5-10 2'-OCH3 modified nucleotides. In another embodiment, the siRNA comprises 15-20 2'-OCH3 modified nucleotides. In another embodiment, the siRNA comprises 20-25 2'-OCH3 modified nucleotides. In another embodiment, the siRNA comprises 25-30 2'-OCH3 modified nucleotides.

In one embodiment, the antisense strand comprises 1-2 2'-OCH3 modified nucleotides. In one embodiment, the antisense strand comprises about 2-4 2'-OCH3 modified nucleotides. In one embodiment, the antisense strand comprises about 4-6 2'-OCH3 modified nucleotides. In one embodiment, the antisense strand comprises about 6-8 2'-OCH3 modified nucleotides. In one embodiment, the antisense strand comprises about 8-10 2'-OCH3 modified nucleotides. In one embodiment, the antisense strand comprises about 10-12 2'-OCH3 modified nucleotides.

In one embodiment, the antisense strand comprises about 12-14 2'-OCH3 modified nucleotides. In one embodiment, the antisense strand comprises about 14-16 2'-OCH3 modified nucleotides. In one embodiment, the antisense strand comprises about 16-18 2'-OCH3 modified nucleotides. In one embodiment, the antisense strand comprises about 18-20 2'-OCH3 modified nucleotides. In one embodiment, the antisense strand comprises about 22-24 2'-OCH3 modified nucleotides. In one embodiment, the antisense strand comprises about 24-26 2'-OCH3 modified nucleotides.

In one embodiment, the sense strand comprises 1-2 2'-OCH3 modified nucleotides. In one embodiment, the sense strand comprises about 2-4 2'-OCH3 modified nucleotides. In one embodiment, the sense strand comprises about 4-6 2'-OCH3 modified nucleotides. In one embodiment, the sense strand comprises about 6-8 2'-OCH3 modified nucleotides. In one embodiment, the sense strand comprises about 8-10 2'-OCH3 modified nucleotides. In one embodiment, the sense strand comprises about 10-12 2'-OCH3 modified nucleotides. In one embodiment, the sense strand comprises about 12-14 2'-OCH3 modified nucleotides. In one embodiment, the sense strand comprises about 14-16 2'-OCH3 modified nucleotides. In one embodiment, the sense strand comprises about 16-18 2'-OCH3 modified nucleotides. In one embodiment, the sense strand comprises about 18-20 2'-OCH3 modified nucleotides. In one embodiment, the sense strand comprises about 22-24 2'-OCH3 modified nucleotides. In one embodiment, the sense strand comprises about 24-26 2'-OCH3 modified nucleotides.

In one embodiment, the siRNA duplex region comprises 1-5 2'-OCH3 modified nucleotides. In another embodiment, the siRNA duplex region comprises 5-10 2'-OCH3 modified nucleotides. In another embodiment, the siRNA duplex region comprises 15-20 2'-OCH3 modified nucleotides. In another embodiment, the siRNA duplex region comprises 20-25 2'-OCH3 modified nucleotides. In another embodiment, the siRNA duplex region comprises 25-30 2'-OCH3 modified nucleotides.

In one embodiment, the antisense duplex region comprises 1-2 2'-OCH3 modified nucleotides. In one embodiment, the antisense duplex region comprises about 2-4 2'-OCH3 modified nucleotides. In one embodiment, the antisense duplex region comprises about 4-6 2'-OCH3 modified nucleotides. In one embodiment, the antisense duplex region comprises about 6-8 2'-OCH3 modified nucleotides. In one embodiment, the antisense duplex region comprises about 8-10 2'-OCH3 modified nucleotides. In one embodiment, the antisense duplex region comprises about 10-12 2'-OCH3 modified nucleotides. In one embodiment, the antisense duplex region comprises about 12-14 2'-OCH3 modified nucleotides. In one embodiment, the antisense duplex region comprises about 14-16 2'-OCH3 modified nucleotides. In one embodiment, the antisense duplex region comprises about 16-18 2'-OCH3 modified nucleotides. In one embodiment, the antisense duplex region comprises about 18-20 2'-OCH3 modified nucleotides. In one embodiment, the antisense duplex region comprises about 22-24 2'-OCH3 modified nucleotides. In one embodiment, the antisense duplex region comprises about 24-26 2'-OCH3 modified nucleotides.

In one embodiment, the sense duplex region comprises 1-2 2'-OCH3 modified nucleotides. In another embodiment, the sense duplex region comprises about 2-4 2'-OCH3 modified nucleotides. In another embodiment, the sense duplex region comprises about 4-6 2'-OCH3 modified nucleotides. In another embodiment, the sense duplex region comprises about 6-8 2'-OCH3 modified nucleotides. In another embodiment, the sense duplex region comprises about 8-10 2'-OCH3 modified nucleotides. In another embodiment, the sense duplex region comprises about 10-12 2'-OCH3 modified nucleotides. In another embodiment, the sense duplex region comprises about 12-14 2'-OCH3 modified nucleotides. In another embodiment, the sense duplex region comprises about 14-16 2'-OCH3 modified nucleotides. In another embodiment, the sense duplex region comprises about 16-18 2'-OCH3 modified nucleotides. In another embodiment, the sense duplex region comprises about 18-20 2'-OCH3 modified nucleotides. In another embodiment, the sense duplex region comprises about 22-24 2'-OCH3 modified nucleotides. In another embodiment, the sense duplex region comprises about 24-26 2'-OCH3 modified nucleotides.

In one embodiment, the siRNA comprises an antisense strand 19 nucleotides in length and a sense strand 19 nucleotides in length, wherein said antisense strand comprises 2'-OCH3 modifications at nucleotides 1, 3, 5, 7, 9, 11, 13, 15, 17 and 19, and wherein said sense strand comprises 2'-OCH3 modifications at nucleotides 2, 4, 6, 8, 10, 12, 14, 16 and 18, wherein said antisense strand is numbered from 5'-3' and said sense strand is numbered from 3'-5'. In another embodiment, the siRNA comprises an antisense strand 20 nucleotides in length and a sense strand 20 nucleotides in length, wherein said antisense strand comprises 2'-OCH3 modifications at nucleotides 1, 3, 5, 7, 9, 11, 13, 15, 17 and 19, and wherein said sense strand comprises 2'-OCH3 modifications at nucleotides 2, 4, 6, 8, 10, 12, 14, 16, 18 and 20 wherein said antisense strand is numbered from 5'-3' and said sense strand is numbered from 3'-5'. In another embodiment, the siRNA comprises an antisense strand 21 nucleotides in length and a sense strand 21 nucleotides in length, wherein said antisense strand comprises 2'-OCH3 modifications at nucleotides 1, 3, 5, 7, 9, 11, 13, 15, 17, 19 and 21, and wherein said sense strand comprises 2'-OCH3 modifications at nucleotides 2, 4, 6, 8, 10, 12, 14, 16, 18 and 20, wherein said antisense strand is numbered from 5'-3' and said sense strand is numbered from 3'-5'. In another embodiment, the siRNA comprises an antisense strand 22 nucleotides in length and a sense strand 22 nucleotides in length, wherein said antisense strand comprises 2'-OCH3 modifications at nucleotides 1, 3, 5, 7, 9, 11, 13, 15, 17, 19 and 21, and wherein said sense strand comprises 2'-OCH3 modifications at nucleotides 2, 4, 6, 8, 10, 12, 14, 16, 18, 20 and 22, wherein said antisense strand is numbered from 5'-3' and said sense strand is numbered from 3'-5'. In another embodiment, the siRNA comprises an antisense strand 23 nucleotides in length and a sense strand 23 nucleotides in length, wherein said antisense strand comprises 2'-OCH3 modifications at nucleotides 1, 3, 5, 7, 9, 11, 13, 15, 17, 19, 21 and 23, and wherein said sense strand comprises 2'-OCH3 modifications at nucleotides 2, 4, 6, 8, 10, 12, 14, 16, 18, 20 and 22 wherein said antisense strand is numbered from 5'-3' and said sense strand is numbered from 3'-5'.

In another embodiment, the siRNA comprises an antisense strand 18-23 nucleotides in length and a sense strand 18-23 nucleotides in length, wherein said antisense strand comprises 2'-OCH3 modifications at nucleotides 3, 5, 7, 9, 11, 13, 15 and 17, and wherein said sense strand comprises 2'-OCH3 modifications at nucleotides 4, 6, 8, 10, 12, 14 and 16, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 5, 7, 9, 11, 13 and 15, and wherein said sense strand comprises 2'-OCH3 modifications at nucleotides 6, 8, 10, 12 and 14, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7, 9, 11, 13 and wherein said sense strand comprises 2'-OCH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7, 9 and 11, and wherein said sense strand comprises 2'-OCH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7 and 9, and wherein said sense strand comprises 2'-OCH3 modifications at nucleotides 8 and 10, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 9 and 11, and wherein said sense strand comprises 2'-OCH3 modifications at nucleotides 8 and 10, wherein said antisense strand is numbered from 5'-3' and said sense strand is numbered from 3'-5'.

In further embodiments, the siRNA comprises the following nucleotide sequences, wherein the sequences comprise 2'-OCH3 modifications on nucleotides indicated with a capital letter:

In another embodiment, the antisense strand comprises 1, 2, 3, 4, 5, 6, 7, 8, 9, 10, 11, 12, 13, 14, 15, 16, 17, 18, 19, 20, 21, 22, 23, 24 or 25 2'-deoxy nucleotides.

In another embodiment, the sense strand comprises 1, 2, 3, 4, 5, 6, 7, 8, 9, 10, 11, 12, 13, 14, 15, 16, 17, 18, 19, 20, 21, 22, 23, 24 or 25 2'-deoxy nucleotides.

In another embodiment, the antisense strand comprises 1, 2, 3, 4, 5, 6, 7, 8, 9, 10, 11, 12, 13, 14, 15, 16, 17, 18, 19, 20, 21, 22, 23, 24 or 25 2'-fluoro nucleotides.

In another embodiment, the sense strand comprises 1, 2, 3, 4, 5, 6, 7, 8, 9, 10, 11, 12, 13, 14, 15, 16, 17, 18, 19, 20, 21, 22, 23, 24 or 25 2'-fluoro nucleotides.

In another embodiment, the pyrimidine nucleotides in the antisense strand are 2'-O-methyl pyrimidine nucleotides.

In another embodiment, of the purine nucleotides in the antisense strand are 2'-O-methyl purine nucleotides.

In another embodiment, the pyrimidine nucleotides in the antisense strand are 2'-deoxy pyrimidine nucleotides.

In another embodiment, the purine nucleotides in the antisense strand are 2'-deoxy purine nucleotides.

In another embodiment, the pyrimidine nucleotides in the antisense strand are 2'-fluoro pyrimidine nucleotides.

In another embodiment, the purine nucleotides in the antisense strand are 2'-fluoro purine nucleotides.

In another embodiment, the pyrimidine nucleotides in the sense strand are 2'-O-methyl pyrimidine nucleotides.

In another embodiment, of the purine nucleotides in the sense strand are 2'-O-methyl purine nucleotides.

In another embodiment, the pyrimidine nucleotides in the sense strand are 2'-deoxy pyrimidine nucleotides.

In another embodiment, the purine nucleotides in the sense strand are 2'-deoxy purine nucleotides.

In another embodiment, the pyrimidine nucleotides in the sense strand are 2'-fluoro pyrimidine nucleotides.

In another embodiment, the purine nucleotides in the sense strand are 2'-fluoro purine nucleotides.

In another embodiment, the pyrimidine nucleotides in the antisense duplex region are 2'-O-methyl pyrimidine nucleotides.

In another embodiment, of the purine nucleotides in the antisense duplex region are 2'-O-methyl purine nucleotides.

In another embodiment, the pyrimidine nucleotides in the antisense duplex region are 2'-deoxy pyrimidine nucleotides.

In another embodiment, the purine nucleotides in the antisense duplex region are 2'-deoxy purine nucleotides.

In another embodiment, the pyrimidine nucleotides in the antisense duplex region are 2'-fluoro pyrimidine nucleotides.

In another embodiment, the purine nucleotides in the antisense duplex region are 2'-fluoro purine nucleotides.

In another embodiment, the pyrimidine nucleotides in the sense duplex region are 2'-O-methyl pyrimidine nucleotides.

In another embodiment, of the purine nucleotides in the sense duplex region are 2'-O-methyl purine nucleotides.

In another embodiment, the pyrimidine nucleotides in the sense duplex region are 2'-deoxy pyrimidine nucleotides.

In another embodiment, the purine nucleotides in the sense duplex region are 2'-deoxy purine nucleotides.

In another embodiment, the pyrimidine nucleotides in the sense duplex region are 2'-fluoro pyrimidine nucleotides.

In another embodiment, the purine nucleotides in the sense duplex region are 2'-fluoro purine nucleotides.

In another embodiment, the pyrimidine nucleotides in the antisense duplex flanking regions are 2'-O-methyl pyrimidine nucleotides.

In another embodiment, of the purine nucleotides in the antisense duplex flanking regions are 2'-O-methyl purine nucleotides.

In another embodiment, the pyrimidine nucleotides in the antisense duplex flanking regions are 2'-deoxy pyrimidine nucleotides.

In another embodiment, the purine nucleotides in the antisense duplex flanking regions are 2'-deoxy purine nucleotides.

In another embodiment, the pyrimidine nucleotides in the antisense duplex flanking regions are 2'-fluoro pyrimidine nucleotides.

In another embodiment, the purine nucleotides in the antisense duplex flanking regions are 2'-fluoro purine nucleotides.

In another embodiment, the pyrimidine nucleotides in the sense duplex flanking regions are 2'-O-methyl pyrimidine nucleotides.

In another embodiment, of the purine nucleotides in the sense duplex flanking regions are 2'-O-methyl purine nucleotides.

In another embodiment, the pyrimidine nucleotides in the sense duplex flanking regions are 2'-deoxy pyrimidine nucleotides.

In another embodiment, the purine nucleotides in the sense duplex flanking regions are 2'-deoxy purine nucleotides.

In another embodiment, the pyrimidine nucleotides in the sense duplex flanking regions are 2'-fluoro pyrimidine nucleotides.

In another embodiment, the purine nucleotides in the sense duplex flanking regions are 2'-fluoro purine nucleotides.

Pattern:

It is within the present invention that any disclosure related to pattern provided herein specifically referring to an antisense strand equally applies to an antisense stretch, and any disclosure related to pattern provided herein specifically referring to an sense strand equally applies to a sense stretch In one embodiment, the antisense duplex region comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense duplex region is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense duplex region comprise a modified base. In another embodiment, the nucleotides of said modified groups comprise a modified phosphate backbone. In another embodiment, the nucleotides of said modified groups comprise a modified 2' position.

In another aspect, the sense duplex region comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense duplex region is identical. In another embodiment, each flanking group has an equal number of nucleotides. In another embodiment, each flanking group is identical. In another embodiment, the nucleotides of said modified groups in the sense duplex region comprise a modified base. In another embodiment, the nucleotides of said modified groups comprise a modified phosphate backbone. In another embodiment, the nucleotides of said modified groups comprise a modified 2' position.

In another aspect, the antisense duplex region and the sense duplex region each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense duplex region and the sense duplex region are identical. In another embodiment, each flanking group in the antisense duplex region and the sense duplex region has an equal number of nucleotides. In another embodiment, each flanking group in the antisense duplex region and in the sense duplex region are identical. In another embodiment, the nucleotides of said modified groups in the antisense duplex region and the sense duplex region each comprise the same modified groups and the same flanking groups. In another embodiment, the nucleotides of said modified groups in the antisense duplex region and the sense duplex region each comprise a modified base. In another embodiment, the nucleotides of said modified groups in the antisense duplex region and the sense duplex region each comprise a modified phosphate backbone. In another embodiment, the nucleotides of said modified groups in the antisense duplex region and the sense duplex region each comprise a modified 2' position.

In one aspect, the antisense strand comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense strand is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense strand comprise a modified base. In another embodiment, the nucleotides of said modified groups comprise a modified phosphate backbone. In another embodiment, the nucleotides of said modified groups comprise a modified 2' position.

In another aspect, the sense strand comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense strand is identical. In another embodiment, each flanking group has an equal number of nucleotides. In another embodiment, each flanking group is identical. In another embodiment, the nucleotides of said modified groups in the sense strand comprise a modified base. In another embodiment, the nucleotides of said modified groups comprise a modified phosphate backbone. In another embodiment, the nucleotides of said modified groups comprise a modified 2' position.

In another aspect, the antisense strand and the sense strand each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense strand and the sense strand are identical. In another embodiment, each flanking group in the antisense strand and the sense strand each have an equal number of nucleotides. In another embodiment, each flanking group in the antisense strand and in the sense strand are identical. In another embodiment, the nucleotides of said modified groups in the antisense strand and the sense strand each comprise the same modified groups and the same flanking groups. In another embodiment, the nucleotides of said modified groups in the antisense strand and the sense strand each comprise a modified base. In another embodiment, the nucleotides of said modified groups in the antisense strand and the sense strand each comprise a modified phosphate backbone. In another embodiment, the nucleotides of said modified groups in the antisense strand and the sense strand each comprise a modified 2' position.

In another aspect, the modified groups and the flanking groups form a regular pattern on the antisense stand. In another aspect, the modified groups and the flanking groups form a regular pattern on the sense strand. In one embodiment, the modified groups and the flanking groups form a regular pattern on the both the antisense strand and the sense strand. In another embodiment, the modified groups and the flanking groups form a regular pattern on the antisense duplex region. In another aspect, the modified groups and the flanking groups form a regular pattern on the sense duplex region. In one embodiment, the modified groups and the flanking groups form a regular pattern on the both the antisense duplex region and the sense duplex region.

In another aspect, the pattern is a spatial or positional pattern. A spatial or positional pattern means that (a) nucleotide(s) are modified depending on their position within the nucleotide sequence of a double-stranded portion. Accordingly, it does not matter whether the nucleotide to be modified is a pyrimidine or a purine. Rather the position of a modified nucleotide is dependent upon: (a) its numbered position on a strand of nucleic acid, wherein the nucleotides are numbered from the 5'-end to the 3'-end with the 5'-end nucleotide of the strand being position one (both the antisense strand and sense strand are numbered from their respective 5'-end nucleotide), or (b) the position of the modified group relative to a flanking group. Thus, according to this embodiment, the modification pattern will always be the same, regardless of the sequence which is to be modified.

In another embodiment, the number of modified groups on the antisense strand is selected from 1, 2, 3, 4, 5, 6, 7, 8, 9, 10, 11, 12, 13 or 14. In another embodiment, the number of modified groups on the sense strand is selected from 1, 2, 3, 4, 5, 6, 7, 8, 9, 10, 11, 12, 13 or 14. In another embodiment, the number of flanking groups on the antisense strand of nucleic acid is selected from 1, 2, 3, 4, 5, 6, 7, 8, 9, 10, 11, 12, 13 or 14. In another embodiment, the number of flanking groups on the sense strand of nucleic acid is selected from 1, 2, 3, 4, 5, 6, 7, 8, 9, 10, 11, 12, 13 or 14.

In one embodiment, the number of modified groups and the number of flanking groups on either or both the antisense strand and the sense strand are the same.

In another embodiment, the number of modified groups on the antisense duplex region is selected 1, 2, 3, 4, 5, 6, 7, 8, 9, 10, 11, 12, 13 or 14. In another embodiment, the number of modified groups on the sense duplex region is selected from 1, 2, 3, 4, 5, 6, 7, 8, 9, 10, 11, 12, 13 or 14. In another embodiment, the number of flanking groups on the antisense duplex region of nucleic acid is 1, 2, 3, 4, 5, 6, 7, 8, 9, 10, 11, 12, 13 or 14. In another embodiment, the number of flanking groups on the sense duplex region of nucleic acid is selected from 1, 2, 3, 4, 5, 6, 7, 8, 9, 10, 11, 12, 13 or 14. In one embodiment, the number of modified groups and the number of flanking groups on either or both the antisense duplex region and the sense duplex region are the same.

In one embodiment, the number of modified groups and the number of flanking groups on a strand or on a duplex region are the same. In another embodiment, the number of modified groups and the number of flanking groups on a strand or on a duplex region are the same, wherein the number is selected from 1, 2, 3, 4, 5, 6, 7, 8, 9, 10, 11, 12, 13 or 14.

In another embodiment, the number of nucleotides in a modified group is selected from 1, 2, 3, 4, 5, 6, 7, 8, 9, 10, 11, 12, 13 or 14. In another embodiment, the number of nucleotides in a flanking group is selected from 1, 2, 3, 4, 5, 6, 7, 8, 9, 10, 11, 12, 13 or 14.

In one embodiment, each modified group on both the antisense strand and the sense strand is identical. In one embodiment, each modified group on both the antisense duplex region and the sense duplex region is identical. In another embodiment, each modified group and each flanking group on both the antisense strand and the sense strand are identical. In one embodiment, each modified group and each flanking group on both the antisense duplex region and the sense duplex region are identical.

In one embodiment, each modified group, each modified group position, each flanking group and each flanking group position on both the antisense strand and the sense strand are identical. In one embodiment, each modified group, each modified group position, each flanking group and each flanking group position on both the antisense duplex region and the sense duplex region are identical. In another embodiment, the modified groups on the antisense strand are complementary with the modified groups on the sense strand (the modified groups on the antisense strand and the sense strand are perfectly aligned across from one another). In another embodiment, there are no mismatches in the modified groups such that each modified group on the antisense strand is base paired with each modified group on the sense strand. In another embodiment, each modified group on the sense strand is shifted by 1, 2, 3, 4 or 5 nucleotides relative to the modified groups on the antisense strand. For example, if each modified group on the sense strand is shifted by one nucleotide and a modified group started at position one on the antisense strand, a modified group on the sense strand would begin at position two. In another embodiment, the modified groups of the antisense strand do not overlap the modified groups of the sense strand, i.e., no nucleotide of a modified group on the antisense strand is base paired with a nucleotide of a modified group on the sense strand.

In one embodiment, deoxyribonucleotides at an end of a strand of nucleic acid are not considered when determining a position of a modified group, i.e., the positional numbering begins with the first ribonucleotide or modified ribonucleotide. In another embodiment, abasic nucleotides at an end of a strand of nucleic acid are not considered when determining a position of a modified group.

In one aspect, a modified group comprises a 5'-end nucleotide of either or both of the antisense strand and the sense strand. In another embodiment, a flanking group comprises the 5'-end nucleotide of either or both of the antisense strand and the sense strand. In another embodiment, the 5'-end nucleotide of either or both of the antisense strand and the sense strand is unmodified. In another embodiment, a modified group comprises the 5'-most nucleotide of either or both of the antisense duplex region and sense duplex region. In another embodiment, a flanking group comprises the 5'-most nucleotide of either or both of the antisense duplex region or the sense duplex region. In another embodiment, the 5'-most nucleotide of either or both of the antisense duplex region or the sense duplex region is unmodified. In another embodiment, the nucleotide at position 10 of the antisense strand is unmodified. In another embodiment, the nucleotide at position 10 of the sense strand is modified. In another embodiment, a modified group comprises the nucleotide at position 10 of the sense strand.

In one embodiment, the modification at the 2' position is selected from the group comprising amino, fluoro, methoxy, alkoxy and $C_1$-$C_3$-alkyl. In another embodiment, the modification is 2'-O-methyl.

In another aspect, each modified group consists of one nucleotide and each flanking group consists of one nucleotide. In one embodiment, each modified group on the antisense strand is aligned with a flanking group on the sense strand.

In another aspect, each modified group consists of one 2'-O-methyl modified nucleotide and each flanking group consists of one nucleotide. In one embodiment, each flanking group consists of one unmodified nucleotide. In one embodiment, each flanking group consists of one 2'-O-methyl modified nucleotide. In another embodiment, each modified group on both the antisense strand and the sense strand consists of one 2'-O-methyl modified nucleotide and each flanking group on both the antisense strand and the sense strand consists of one nucleotide, wherein no modified group on one strand is either aligned or both aligned and base paired with another modified group on the other strand and no flanking group on one strand is either aligned or both aligned and base paired with a flanking group on the other strand. In another embodiment, excluding any optional overhangs, each modified group on each strand is either aligned or both aligned and based paired with a flanking group on the other strand. In one embodiment, the flanking group is unmodified. In another embodiment, the nucleotide of position one on the antisense strand is 2'-O-methyl modified. In another embodiment, the 5'-most nucleotide of the antisense duplex region is 2'-O-methyl modified.

Positional modification schemes are described in international patent application WO 2004/015107, incorporated by reference in its entirety.

Modifications to Phosphate Backbone:

It is within the present invention that any disclosure related to modification to phosphate backbone provided herein specifically referring to an antisense strand or nucleotides forming such antisense strand equally applies to an antisense stretch or nucleotides forming such antisense stretch, and any disclosure related to modification to phosphate backbone provided herein specifically referring to a sense strand or nucleotides forming such sense strand equally applies to a sense stretch or nucleotides forming such sense stretch.

In one embodiment, the nucleic acid molecule of the invention and the siRNA of the invention in particular bear, have or display one or several modifications to a phosphate backbone, whereby such modification is preferably one described herein.

All or a portion of the nucleotides of the siRNA of the invention may be linked through phosphodiester bonds, as found in unmodified nucleic acid. A siRNA of the present invention however, may comprise a modified phosphodiester linkage. The phosphodiester linkages of either the antisense stand or the sense strand may be modified to independently include at least one heteroatom selected from the group consisting of nitrogen and sulfur. In one embodiment, a phosphoester group connecting a ribonucleotide to an adjacent ribonucleotide is replaced by a modified group. In one embodiment, the modified group replacing the phosphoester group is selected from the group consisting of phosphothioate, methylphosphonate or phosphoramidate group.

In one embodiment, all of the nucleotides of the antisense strand are linked through phosphodiester bonds. In another embodiment, all of the nucleotides of the antisense duplex region are linked through phosphodiester bonds. In another embodiment, all of the nucleotides of the sense strand are linked through phosphodiester bonds. In another embodiment, all of the nucleotides of the sense duplex region are linked through phosphodiester bonds. In another embodiment, the antisense strand comprises a number of modified phosphodiester groups selected from 1, 2, 3, 4, 5, 6, 7, 8, 9 or 10. In another embodiment, the antisense duplex region comprises a number of modified phosphodiester groups selected from 1, 2, 3, 4, 5, 6, 7, 8, 9 or 10. In another embodiment, the sense strand comprises a number of modified phosphodiester groups selected from 1, 2, 3, 4, 5, 6, 7, 8, 9 or 10. In another embodiment, the sense duplex region comprises a number of modified phosphodiester groups selected from 1, 2, 3, 4, 5, 6, 7, 8, 9 or 10.

In another embodiment, one or more nucleotides forming the antisense duplex region, the sense duplex region or the overhang(s) are linked through phosphorothioate bonds. In a preferred embodiment, the nucleotides forming the overhang are linked to each other by one or more phosphorothioate bonds.

5' and 3' End Modifications:

It is within the present invention that any disclosure related to 5' and 3' end modifications provided herein specifically referring to an antisense strand or nucleotides forming such antisense strand equally applies to an antisense stretch or nucleotides forming such antisense stretch, and any disclosure related to 5' and 3' end modifications modification provided herein specifically referring to a sense strand or nucleotides forming such sense strand equally applies to a sense stretch or nucleotides forming such sense stretch.

In one embodiment, the nucleic acid molecule of the invention and the siRNA of the invention in particular bear, have or display a 5' and/or 3' modification, whereby such modification is preferably one described herein.

The siRNA of the present invention may include nucleic acid molecules comprising one or more modified nucleotides, abasic nucleotides, acyclic or deoxyribonucleotide at the terminal 5'- or 3'-end on either or both of the sense or antisense strands. In one embodiment, the 5'- and 3'-end nucleotides of both the sense and antisense strands are unmodified. In another embodiment, the 5'-end nucleotide of the antisense strand is modified. In another embodiment, the 5'-end nucleotide of the sense strand is modified. In another embodiment, the 3'-end nucleotide of the antisense strand is modified. In another embodiment, the 3'-end nucleotide of the sense strand is modified. In another embodiment, the 5'-end nucleotide of the antisense strand and the 5'-end nucleotide of the sense strand are modified. In another embodiment, the 3'-end nucleotide of the antisense strand and the 3'-end nucleotide of the sense strand are modified. In another embodiment, the 5'-end nucleotide of the antisense strand and the 3'-end nucleotide of the sense strand are modified. In another embodiment, the 3'-end nucleotide of the antisense strand and the 5'-end nucleotide of the sense strand are modified. In another embodiment, the 3'-end nucleotide of the antisense strand and both the 5'- and 3'-end nucleotides of the sense strand are modified. In another embodiment, both the 5'- and 3'-end nucleotides of the antisense strand are modified. In another embodiment, both the 5'- and 3'-end nucleotides of the sense strand are modified.

In another embodiment, the 5'-end nucleotide of the antisense strand is phosphorylated. In another embodiment, the 5'-end nucleotide of the sense strand is phosphorylated. In another embodiment, the 5'-end nucleotides of both the antisense strand and the sense strand are phosphorylated. In another embodiment, the 5'-end nucleotide of the antisense strand is phosphorylated and the 5'-end nucleotide of the sense strand has a free hydroxyl group (5'-OH). In another embodiment, the 5'-end nucleotide of the antisense strand is phosphorylated and the 5'-end nucleotide of the sense strand is modified.

Modifications to the 5'- and 3'-end nucleotides are not limited to the 5' and 3' positions on these terminal nucleotides. Examples of modifications to end nucleotides include, but are not limited to, biotin, inverted (deoxy) abasics, amino, fluoro, chloro, bromo, CN, CF, methoxy, imidazole, caboxylate, thioate, C1 to C10 lower alkyl, substituted lower alkyl, alkaryl or aralkyl, OCF3, OCN, O—, S—, or N-alkyl; O—, S—, or N-alkenyl; SOCH3; SO2CH3; ONO2; NO2, N3; heterozycloalkyl; heterozycloalkaryl; aminoalkylamino; polyalkylamino or substituted silyl, as, among others, described, e.g., in PCT patent application WO 99/54459, European patents EP 0 586 520 B1 or EP 0 618 925 B1, incorporated by reference in their entireties. As used herein, "alkyl" means C1-C12-alkyl and "lower alkyl" means C1-C6-alkyl, including C1-, C2-, C3-, C4-, C5- and C6-alkyl.

In another aspect, the 5'-end of the antisense strand, the 5'-end of the sense strand, the 3'-end of the antisense strand or the 3'-end of the sense strand is covalently connected to a prodrug moiety. In one embodiment, the moiety is cleaved in an endosome. In another the moiety is cleaved in the cytoplasm.

Various possible non-limiting embodiments of the siRNA of the present invention having different kinds of end modification(s) are presented in the following Table.

Various embodiments of the interfering ribonucleic acid according to the present invention

| | | Antisense strand | Sense strand |
|---|---|---|---|
| 1.) | 5'-end | free OH | free OH |
| | 3'-end | free OH | free OH |
| 2.) | 5'-end | free OH | free OH |
| | 3'-end | end modification | end modification |
| 3.) | 5'-end | free OH | free OH |
| | 3'-end | free OH | end modification |
| 4.) | 5'-end | free OH | free OH |
| | 3'-end | end modification | free OH |
| 5.) | 5'-end | free OH | end modification |
| | 3'-end | free OH | free OH |
| 6.) | 5'-end | free OH | end modification |
| | 3'-end | end modification | free OH |
| 7.) | 5'-end | free OH | end modification |
| | 3'-end | free OH | end modification |
| 8.) | 5'-end | free OH | end modification |
| | 3'-end | end modification | end modification |

In another embodiment, the terminal 3' nucleotide or two terminal 3'-nucleotides on either or both of the antisense strand or sense strand is a 2'-deoxynucleotide. In another embodiment, the 2'-deoxynucleotide is a 2'-deoxy-pyrimidine. In another embodiment, the 2'-deoxynucleotide is a 2' deoxy-thymidine.

shRNA and Linked siRNA:

It is within the present invention that any disclosure related to shRNA and linked siRNA provided herein specifically referring to an antisense strand or nucleotides forming such antisense strand equally applies to an antisense stretch or nucleotides forming such antisense stretch, and any disclosure related to 5' and 3' end modifications modification provided herein specifically referring to a sense strand or nucleotides forming such sense strand equally applies to a sense stretch or nucleotides forming such sense stretch.

In one embodiment, the nucleic acid molecule of the invention and the siRNA of the invention in particular are shRNA and/or linked siRNA, whereby such shRNA and/or linked siRNA is preferably one described herein.

It is within the present invention that the double-stranded structure is formed by two separate strands, i.e. the antisense strand and the sense strand. However, it is also with in the present invention that the antisense strand and the sense strand are covalently linked to each other. Such linkage may occur between any of the nucleotides forming the antisense strand and sense strand, respectively. Such linkage can be formed by covalent or non-covalent linkages. Covalent linkage may be formed by linking both strands one or several times and at one or several positions, respectively, by a compound preferably selected from the group comprising methylene blue and bifunctional groups. Such bifunctional groups are preferably selected from the group comprising bis(2-chloroethyl)amine, N-acetly-N'-(p-glyoxylbenzoyl) cystamine, 4-thiouracile and psoralene.

In one embodiment, the antisense strand and the sense strand are linked by a loop structure. In another embodiment, of the loop structure is comprised of a non-nucleic acid polymer. In another embodiment, the non-nucleic acid polymer is polyethylene glycol. In another embodiment, the 5'-end of the antisense strand is linked to the 3'-terminus of the sense strand. In another embodiment, the 3'-end of the antisense strand is linked to the 5'-end of the sense strand.

In another embodiment, the loop consists of a nucleic acid. As used herein, locked nucleic acid (LNA) (Elayadi and Corey (2001) Curr Opin Investig Drugs. 2(4):558-61) and peptide nucleic acid (PNA) (reviewed in Faseb J. (2000) 14:1041-1060) are regarded as nucleic acids and may also be used as loop forming polymers. In one embodiment, the nucleic acid is ribonucleic acid. In one embodiment, the 5'-terminus of the antisense strand is linked to the 3'-terminus of the sense strand. In another embodiment, the 3'-end of the antisense strand is linked to the 5'-terminus of the sense strand. The loop consists of a minimum length of four nucleotides or nucleotide analogues. In one embodiment, the loop consists of a length of nucleotides or nucleotide analogues selected from 4, 5, 6, 7, 8, 9, 10, 11, 12, 13, 14 or 15. In one embodiment, the length of the loop is sufficient for linking the two strands covalently in a manner that a back folding can occur through a loop structure or similar structure. The ribonucleic acid constructs may be incorporated into suitable vector systems. Preferably the vector comprises a promoter for the expression of RNAi. Preferably the respective promoter is pol III and more preferably the promoters are the U6, H1, 7SK promoter as described in Good et al. (1997) Gene Ther. 4, 45-54.

In another embodiment, the nucleic acid according to the present invention comprises a phosphorothioate internucleotide linkage. In one embodiment, a phosphorothioate internucleotide linkage is within 5 nucleotides from the 3'-end or the 5'-end of either or both of the antisense strand and the sense strand. The antisense strand can comprise about one to about five phosphorothioate internucleotide linkages.

COMBINATIONS OF EMBODIMENTS

It is within the present invention that any disclosure related to combinations of embodiments provided herein specifically referring to an antisense strand or nucleotides forming such antisense strand equally applies to an antisense stretch or nucleotides forming such antisense stretch, and any disclosure related to 5' and 3' end modifications modification provided herein specifically referring to a sense strand or nucleotides forming such sense strand equally applies to a sense stretch or nucleotides forming such sense stretch.

In one embodiment, an overhang at the 3'-end of the sense strand is selected from consisting of 1, 2, 3, 4 and 5 nucleotides in length. In one embodiment, an overhang at the 5'-end of the antisense strand is selected from consisting of 1, 2, 3, 4 and 5 nucleotides in length. In one embodiment, an overhang at the 5'-end of the sense strand is selected from consisting of 1, 2, 3, 4 and 5 nucleotides in length.

In one embodiment, the siRNA molecule is blunt-ended on both ends and has a length selected from the group consisting of 16, 17, 18, 19, 20, 21, 22, 23, 24, 25, 26, 27, 28 or 29 consecutive nucleotides.

In one embodiment, the siRNA molecule is blunt-ended on one end and the double stranded portion of the siRNA molecule has a length selected from the group consisting of 16, 17, 18, 19, 20, 21, 22, 23, 24, 25, 26, 27, 28 or 29 consecutive nucleotides.

In one embodiment, the siRNA molecule has overhangs on both ends and the double stranded portion of the siRNA molecule has a length selected from the group consisting of 16, 17, 18, 19, 20, 21, 22, 23, 24, 25, 26, 27, 28 or 29 consecutive nucleotides.

In one embodiment, the siRNA molecule comprises an overhang, said overhang comprising at least one deoxyribonucleotide. In one embodiment, the siRNA molecule comprises an overhang, said overhang comprising two deoxyribonucleotides.

In one embodiment, the siRNA molecule has overhangs on the 3'-end of the antisense strand and at the 3'-end of the sense strand, said overhangs comprising at least one deoxyribonucleotide. In one embodiment, the siRNA molecule has overhangs on the 3'-end of the antisense strand and at the 3'-end of the sense strand, said overhangs consisting two deoxyribonucleotides.

The nucleotide(s) forming the overhang may be (a) desoxyribonucleotide(s), (a) ribonucleotide(s) or a combination thereof. In one embodiment, the antisense strand and/or the sense strand comprise a TT dinucleotide at the 3' end.

In a preferred embodiment dT as used herein is indicative of a deoxyribonucleotide, namely T, in a molecule which is otherwise an RNA or which consists of ribonucleotides which may, for example, be modified as indicated herein.

Processes of Making:

The nucleic acid of the present invention can be produced using routine methods in the art including chemically synthesis or expressing the nucleic acid either in vitro (e.g., run off transcription) or in vivo. In one embodiment, the siRNA is produced using solid phase chemical synthesis. In another embodiment, the nucleic acid is produced using an expression vector. In one embodiment, the expression vector produced the nucleic acid of the invention in the target cell. Accordingly, such vector can be used for the manufacture of a medicament. Methods for the synthesis of the nucleic acid molecule described herein are known to the ones skilled in the art. Such methods are, among others, described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311 (each incorporated herein by reference in their entireties).

As used herein in connection with any aspect of the invention a wording defining the limits of a range of length such as, e. g., "from 13 to 35" means any integer from 13 to 35, i. e. 13, 14, 15, 16, 17, 18, 19, 20, 21, 22, 23, 24, 25, 26, 27, 28, 29, 30, 31, 32, 33, 34 and 35. In other words, any range defined by two integers explicitly mentioned is meant to comprise and disclose any integer defining said limits and any integer comprised within said range.

Delivery/Formulations:

siRNA can be delivered to cells, both in vitro and in vivo, by a variety of methods known to those of skill in the art, including direct contact with cells ("naked" siRNA) or by in combination with one or more agents that facilitate targeting or delivery into cells. Such agents and methods include nanoemulsions (WO 2009/141257 A1), lipoplexes, liposomes, iontophoresis, hydrogels, cyclodextrins, nanocapsules, micro- and nanospheres and proteinaceous vectors (e.g., Bioconjugate Chem. (1999) 10:1068-1074 and WO 00/53722). The nucleic acid/vehicle combination may be locally delivered in vivo by direct injection or by use of an infusion pump. The siRNA of the invention can be delivered in vivo by various means including intravenous subcutaneous, intramuscular or intradermal injection or inhalation. The molecules of the instant invention can be used as pharmaceutical agents. Preferably, pharmaceutical agents prevent, modulate the occurrence, or treat (alleviate a symptom to some extent, preferably all of the symptoms) of a disease state in a subject. Accordingly, the present invention is related in a further aspect to a composition comprising a nucleic acid molecule of the invention and one of such agents; preferably such composition is for delivery of the nucleic acid molecule of the invention in any of the methods described herein.

The nanoemulsion as described in international patent application WO 2009/141257 A1 is a stable perfluorcarbon nanoemulsion having an endocytosis enhancing surface, whereby the nanoemulsion has a discontinuous perfluorcarbon phase and a buffered continuous aqueous phase and comprises (a) a perfluorcarbon component comprising at least one least one perfluorocarbon compound; (b) an emulsifying component; and (c) an endocytosis enhancing component comprising at least one compound inducing cellular uptake of the nanoemulsion via endocytosis. The nanoemulsion may have a particle size of below 100 nm, preferably the nanoemulsion consists of particles having an average size of about 50 nm. Methods for measuring particle sizes are known in the art and, for example, described in Murdock R C et al. (R. C. Murdock, et al., "Characterization of nanomaterial dispersion in solution prior to in vitro exposure using dynamic light scattering technique," *Toxicol. Sci.* 101(2), 239 (2008)) or in Bootz et al. (A. Bootz, V. Vogel, D. Schubert, and J. Kreuter, "Comparison of scanning electron microscopy, dynamic light scattering and analytical ultracentrifugation for the sizing of poly(butyl cyanoacrylate) nanoparticles," *Eur. J. Pharm. Biopharm.* 57(2), 369 (2004).) Typically, the buffered aqueous phase represents 25 to 60 wt. % of the nanoemulsion. In an embodiment, the at least one compound inducing cellular uptake via endocytosis is selected from transferrin, apolipoprotein A1, glycosylphosphatidylinositol(GIP)-anchored proteins, megalinbinding proteins, atennapedia proteins, fragments and derivatives of said compounds and compounds having an analogous effect, most preferably said compound is transferrin or a fragment or derivative thereof. In another embodiment, the at least one perfluorocarbon compound is selected from $C_mF_{2m+1}X$, $XC_mF_{2m}X$, $XC_nF_{2n}OC_oF_{2o}X$, $N(C_oF_{2o}X)_3$ and $N(C_oF_{2o+1})_3$ (wherein m is an integer from 3 to 10, n and o are integers from 1 to 5, and X is independently from further occurrence selected from Cl, Br and I), preferably the perfluorcarbon is selected from perfluoroocytlbromide and perfluorotributylamine and mixtures thereof. The emulsifying component may comprise at least one phospholipid as the essential emulsifying component and one or more helper lipids. The least one phospholipid is selected from compounds represented by the formula I

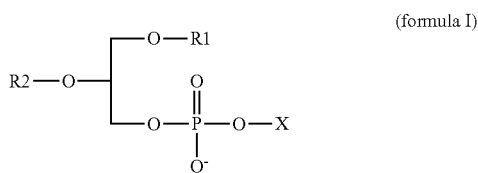
(formula I)

wherein $R^1$ und $R^2$ are independently selected from H and $C_{16-24}$ acyl residues, which may be saturated or unsaturated and may carry 1 to 3 residues $R^3$ and wherein one or more of the C-atoms may be substituted by 0 or $NR^4$, and X is selected from H, $-(CH_2)_p-N(R^4)_3^+$, $-(CH_2)_p-CH(N(R^4)_3^+)-COO-$, $-(CH_2)_p-CH(OH)-CH_2OH$ and $-CH_2(CHOH)_p-CH_2OH$ (wherein p is an integer from 1 to 5; $R^3$ is independently selected from H, lower alkyl, F, Cl, CN und OH; and $R^4$ is independently selected from H, $CH_3$ und $CH_2CH_3$) or a pharmacologically acceptable salt thereof, preferably $R^1$ and $R^2$ are independently selected from Hand unsubstituted $C_{16-24}$ acyl residues, which may be saturated or unsaturated, and X is selected from a choline, serine, ethanolamine and inositol residue, most preferably the phospholipid component is selected from phosphatidylcholine, Iysophoshatidylcholine, phophatidylethanolamine and mixtures thereof. The helper lipid may be selected from fatty acids, steroids, vitamins and mixtures thereof. In a preferred embodiment the nanoemulsion comprises perfluoroocytlbromide as perfluorcarbon component (a), an emulsifying component (b) comprising phosphatidylcholine, sphingomyelin, cholesterol and Iysophosphatidylcholine, as phospholipid, and transferrin as the endocytosis enhancing component (c).

Lipid nanoparticles comprising phosphatidylcholine which can also be used in the formulation and delivery of the nucleic acid molecule of the invention are, for example, described in Torchilin V P (V. P. Torchilin, "Recent advances with liposomes as pharmaceutical carriers," *Nat. Rev. Drug Discov.* 4(2), 145 (2005)), Ozpolat B et al. (B. Ozpolat, A. K. Sood, and G. Lopez-Berestein, "Nanomedicine based approaches for the delivery of siRNA in cancer," *J Intern. Med.* 267(1), 44 (2010)) or Abbasalipourkabir R et al. (R. Abbasalipourkabir, A. Salehzadeh, and R. Abdullah, "Characterization and stability of nanostructured lipid carriers as drug delivery system," *Pak. J. Biol. Sci.* 15(3), 141 (2012)).

Another means which can be used for the formulation and/or delivery of a nucleic acid molecule of the invention are surface-modified liposomes containing poly (ethylene glycol) lipids (PEG-modified, or long-circulating liposomes or stealth liposomes). These formulations offer a method for increasing stability of a liposome or lipoplex solutions by preventing their aggregation and fusion. The formulations also have the added benefit in vivo of resisting opsonization and elimination by the mononuclear phagocytic system (MPS or RES), thereby enabling longer blood circulation times and enhanced tissue exposure for the encapsulated drug. Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24780; Choi et al., International PCT Publication No. WO 96/10391; Ansell et al., International PCT Publication No. WO 96/10390; Holland et al., International PCT Publication No. WO 96/10392). Long-circulating liposomes also protect the siRNA from nuclease degradation.

A further means which can be used in the formulation and/or delivery of a nucleic acid molecule of the invention are lipoplexes as, for example, described in WO 2005/105152. In a preferred embodiment such lipoplex is a positively charged liposome consisting of:
(a) about 50 mol % ß-arginyl-2,3-diaminopropionic acid-N-palmityl-N-oleyl-amide trihydrochloride, preferably β-(L-arginyl)-2,3-L-diaminopropionic acid-N-palmityl-N-oleyl-amide tri-hydrochloride, (b) about 48 to 49 mol % 1,2-diphytanoyl-sn-glycero-3-phosphoethanolamine (DPhyPE), and (c) about 1 to 2 mol % 1,2-distearoyl-sn-glycero-3-phosphoethanolamine-polyethylen-glycole, preferably N-(Carbonyl-methoxypolyethyleneglycol-2000)-1,2-distearoyl-sn-glycero-3-phosphoethanolamine sodium salt.

Pharmaceutical Compositions

The nucleic acid molecule of the invention may be formulated as pharmaceutical compositions. The pharmaceutical compositions may be used as medicaments or as diagnostic agents, alone or in combination with other agents. The pharmaceutical compositions may be used in any method of the invention.

For example, one or more nucleic acid molecules and/or one or more siRNAs of the invention can be combined with a delivery vehicle (e.g., nanoemulsion or liposomes) and excipients, such as carriers, diluents. In a preferred embodiment a pharmaceutical composition is a composition as described in section "delivery/formulations" herein.

Other agents such as preservatives and stabilizers can also be added. Methods for the delivery of nucleic acid molecules are known in the art and described, e.g., in Akhtar et al., 1992, Trends Cell Bio., 2, 139; Delivery Strategies for Antisense Oligonucleotide Therapeutics, ed. Akhtar, 1995, Maurer et al., 1999, Mol. Memb. Biol., 16, 129-140; Hofland and Huang, 1999, Handb. Exp. Pharmacol., 137, 165-192; and Lee et al., 2000, ACS Symp. Ser., 752, 184-192, U.S. Pat. No. 6,395,713 and PCT WO 94/02595 (each of which are incorporated herein by reference in their entireties). The siRNA of the present invention can also be administered in combination with other therapeutic compounds, either administrated separately or simultaneously, e.g., as a combined unit dose. In one embodiment, the invention includes a pharmaceutical composition comprising one or more siRNA according to the present invention in a physiologically/pharmaceutically acceptable excipient, such as a stabilizer, preservative, diluent, buffer, and the like.

Dosage levels for the medicament and pharmaceutical compositions of the invention can be determined by those skilled in the art by routine experimentation. In one embodiment, a unit dose contains between about 0.01 mg/kg and about 100 mg/kg body weight of siRNA. In one embodiment, the dose of siRNA is about 10 mg/kg and about 25 mg/kg body weight. In one embodiment, the dose of siRNA is about 1 mg/kg and about 10 mg/kg body weight. In one embodiment, the dose of siRNA is about 0.05 mg/kg and about 5 mg/kg body weight. In another embodiment, the dose of siRNA is about 0.1 mg/kg and about 5 mg/kg body weight. In another embodiment, the dose of siRNA is about 0.1 mg/kg and about 1 mg/kg body weight. In another embodiment, the dose of siRNA is about 0.1 mg/kg and about 0.5 mg/kg body weight. In another embodiment, the dose of siRNA is about 0.5 mg/kg and about 1 mg/kg body weight.

In one aspect, the pharmaceutical composition is a sterile injectable aqueous suspension or solution. In one aspect, the pharmaceutical composition is in lyophilized form. In one embodiment the pharmaceutical composition comprises a nanoemulsion comprising a siRNA molecule of the invention. In one embodiment, the pharmaceutical composition comprises lyophilized lipoplexes, wherein the lipoplexes comprises a siRNA of the present invention. In another embodiment, the pharmaceutical composition comprises an aqueous suspension of lipoplexes, wherein the lipoplexes comprises a siRNA of the present invention.

The pharmaceutical compositions and medicaments of the present invention may be administered to a subject (mammal) in the disclosed methods of treatment. In one embodiment, the mammal is selected from the group consisting humans, dogs, cats, horses, cattle, pig, goat, sheep, mouse, rat, hamster and guinea pig. In one embodiment, the mammal is a human. In another embodiment, the mammal is a non-human mammal.

Kits

In a further aspect the invention is related to a kit. The kit comprises a nucleic acid molecule of the invention, preferably a siRNA of the invention, and at least one selected from the group of a container, an instruction leaflet, a buffer, a positive control, a negative control, a delivery agent or delivery agent, whereby the delivery agent is preferably one disclosed herein, and a reaction mixture. The kit is useful in/suitable for the practicing of any method of the invention. In an embodiment the kit is for use in any method of the invention.

Methods of Treatment

The nucleic acid molecule of the invention is useful in and may be used in the treatment and/or prevention of a disease. In an embodiment, the method comprises the administration of a nucleic acid to a subject. Preferably, the subject is suffering from the disease or at risk of suffering from the disease. Preferably, the subject is a mammal. As preferably used herein, a mammal is an animal selected from the group comprising man, ape, monkey, mouse, rat rabbit, cat, dog, cattle, horse, domestic animal, working animal and companion animal. More preferably, the subject is man.

The nucleic acid molecule of the invention is administered to the subject at an effective amount. Preferably such effective amount is a pharmaceutically effective amount or a therapeutically effective amount.

The nucleic acid molecule of the invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficacy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels.

In a preferred embodiment the nucleic acid molecule of the invention is a siRNA of the invention.

In an embodiment, the method for the treatment and/or prevention of a disease is a disease which can be treated by decreasing the expression of the Notch 1 gene and more specifically by decreasing the translation of the mRNA coding for Notch 1. Specific diseases and medical conditions falling within this group of diseases are known to a person skilled in the art. Furthermore, methods for determining this kind of disease are equally known to a person skilled in the art. A preferred disease is cancer, preferably those forms of cancer where Notch 1 is up-regulated, Notch 1 is expressed in an altered manner compared to non-disease tissue or non-diseased tissue and/or where a therapeutic effect may be achieved by decreasing the expression of the Notch 1 gene and more specifically by decreasing the translation of the mRNA coding for Notch 1.

In an embodiment the disease is one of the following group, where the involvement of Notch 1 has been demonstrated and, respectively, Notch 1 been identified as a drugable target: Esophageal cancer (see, Streppel, E. A. Montgomery, and A. Maitra, "New Advances in the Pathogenesis and Progression of Barrett's Esophagus," *Curr. Mol. Med.* (2013)), oral squamous cell carcinoma (see, R. Yoshida, et al., "The pathological significance of Notch1 in oral squamous cell carcinoma," *Lab Invest* (2013)), head and neck cancer (see, J. T. Lin, et al., "Association of high levels of Jagged-1 and Notch-1 expression with poor prognosis in head and neck cancer," *Ann. Surg. Oncol.* 17(11), 2976 (2010)), tongue cancer (see Y. H. Joo, C. K. Jung, M. S. Kim, and D. I. Sun, "Relationship between vascular endothelial growth factor and Notch1 expression and lymphatic metastasis in tongue cancer," *Otolaryngol. Head Neck Surg.* 140(4), 512 (2009)), leukemia (see E. Kanamori, et al., "Flow cytometric analysis of Notch1 and Jagged1 expression in normal blood cells and leukemia cells," *Exp. Ther. Med.* 4(3), 397 (2012); and Zhang J et al. (J. Zhang, et al., "Prognostic impact of delta-like ligand 4 and Notch1 in acute myeloid leukemia," *Oncol. Rep.* 28(4), 1503 (2012)), renal cell carcinoma (see, Q. Ai, et al., "High-level expression of Notch1 increased the risk of metastasis in Ti stage clear cell renal cell carcinoma," *PLoS. One.* 7(4), e35022 (2012) and J. Sjolund, et al., "The notch and TGF-beta signaling pathways contribute to the aggressiveness of clear cell renal cell carcinoma," *PLoS. One.* 6(8), e23057 (2011)), gastric cancer (see, T. S. Yeh, et al., "The activated Notch1 signal pathway is associated with gastric cancer progression through cyclooxygenase-2," *Cancer Res.* 69(12), 5039 (2009), and Y. Sun, et al., "Differential Notch1 and Notch2 expression and frequent activation of Notch signaling in gastric cancers," *Arch. Pathol. Lab Med.* 135(4), 451 (2011)), colon adenocarcinoma (see, M. Reedijk, et al., "Activation of Notch signaling in human colon adenocarcinoma," *Int J. Oncol.* 33(6), 1223 (2008) and M. Reedijk, et al., "Activation of Notch signaling in human colon adenocarcinoma," *Int J. Oncol.* 33(6), 1223 (2008)), endometrial cancer/uterine corpus (see Y. Mitsuhashi, et al., "Prognostic significance of Notch signalling molecules and their involvement in the invasiveness of endometrial carcinoma cells," *Histopathology* 60(5), 826 (2012)), cervical cancer/uterine cervix (see, L. Santos, et al., "Identification of differential expressed transcripts in cervical cancer of Mexican patients," *Tumour. Biol.* 32(3), 561 (2011)), intrahepatic cholangiocarcinoma (see, Q. Zhou, et al., "The roles of Notch1 expression in the migration of intrahepatic cholangiocarcinoma," *BMC. Cancer* 13, 244 (2013), and S. Zender, et al., "A critical role for notch signaling in the formation of cholangiocellular carcinomas," *Cancer Cell* 23(6), 784 (2013)), hepatocellular carcinoma (see, A. Villanueva, et al., "Notch signaling is activated in human hepatocellular carcinoma and induces tumor formation in mice," *Gastroenterology* 143(6), 1660 (2012), and R. Fan, et al., "Cooperation of deregulated Notch signaling and Ras pathway in human hepatocarcinogenesis," *J. Mol. Histol.* 42(5), 473 (2011)), osteosarcoma (see, J. Yang and W. Zhang, "New molecular insights into osteosarcoma targeted therapy," *Curr. Opin. Oncol.* 25(4), 398 (2013)), urinary bladder carcinoma (see, A. G. Abdou, et al., "Immunohistochemical analysis of the role and relationship between Notch-1 and Oct-4 expression in urinary bladder carcinoma," *APMIS* (2013)), malignant melanoma (see, C. S. Muller, "Notch signaling and malignant melanoma," *Adv. Exp. Med. Biol.* 727, 258 (2012)), thyroid cancer (see, H. S. Park, et al., "Notch1 receptor as a marker of lymph node metastases in papillary thyroid cancer," *Cancer Sci.* 103(2), 305 (2012)), lung adenocarcinoma (see K. A. Hassan, et al., "Notch pathway activity identifies cells with cancer stem cell-like properties and correlates with worse survival in lung adenocarcinoma," *Clin. Cancer Res.* 19(8), 1972 (2013), and B. Westhoff, et al., "Alterations of the Notch pathway in lung cancer," *Proc. Natl. Acad. Sci. U. S. A* 106(52), 22293 (2009)), prostata cancer (see, H. Zhu, et al., "Elevated Jagged-1 and Notch-1 expression in high grade and metastatic prostate cancers," *Am. J. Transl. Res.* 5(3), 368 (2013)) and M. Kashat, et al., "Inactivation of AR and Notch-1 signaling by miR-34a attenuates prostate cancer aggressiveness," *Am. J. Transl. Res.* 4(4), 432 (2012)), breast cancer (see, J. Speiser, et al., "Notch-1 and Notch-4 biomarker expression in triple-negative breast cancer," *Int J. Surg. Pathol.* 20(2), 139 (2012), and S. Mittal, et al., "Cooperation of Notch and Ras/MAPK signaling pathways in human breast carcinogenesis," *Mol. Cancer* 8, 128 (2009)), ovarian cancer (see, S. L. Rose, M. Kunnimalaiyaan, J. Drenzek, and N. Seiler, "Notch 1 signaling is active in ovarian cancer," *Gynecol. Oncol.* 117(1), 130 (2010)), pancreatic cancer (see, F. H. Sarkar, S. Banerjee, and Y. Li, "Pancreatic cancer: pathogenesis, prevention and treatment," *Toxicol. Appl. Pharmacol.* 224(3), 326 (2007), O. JP De La, et al., "Notch and Kras reprogram pancreatic acinar cells to ductal intraepithelial neoplasia," Proc. Natl. Acad. Sci. U. S. A 105(48), 18907 (2008), E. Ristorcelli and D. Lombardo, "Targeting Notch signaling in pancreatic cancer," Expert. Opin. Ther. Targets. 14(5), 541 (2010), Z. Wang, et al., "Notch-1 downregulation by curcumin is associated with the inhibition of cell growth and the induction of apoptosis in pancreatic cancer cells," Cancer 106(11), 2503 (2006), P. Buchler, et al., "The Notch signaling pathway is related to neurovascular progression of pancreatic cancer," Ann. Surg. 242(6), 791, discussion (2005), Z. Wang, et al., "Down-regulation of Notch-1 contributes to cell growth inhibition and apoptosis in pancreatic cancer cells," Mol. Cancer Ther. 5(3), 483 (2006), Z. Wang, et al., "Down-regulation of notch-1 inhibits invasion by inactivation of nuclear factor-kappaB, vascular endothelial growth factor, and matrix metalloproteinase-9 in pancreatic cancer cells," Cancer Res. 66(5), 2778 (2006)), and glioma (see, X. Zhang, et al., "Notch1 promotes glioma cell migration and invasion by stimulating beta-catenin and NF-kappaB signaling via AKT activation," Cancer Sci. 103(2), 181 (2012), L. Jiang, et al., "Notch1 expression is upregulated in glioma and is associated with tumor progression," J. Clin. Neurosci. 18(3), 387 (2011), J. Li, et al., "Notch1 is an independent prognostic factor for patients with glioma," J. Surg. Oncol. 103(8), 813 (2011), and S. Puget, et al., "Candidate genes on chromosome 9q33-34 involved in the progression of childhood ependymomas," J. Clin. Oncol. 27(11), 1884 (2009)).

It is within the present invention that in addition to a nucleic acid molecule of the invention at least one further therapeutically or pharmaceutically active agent (also referred to herein as "second of further agent") is used in the methods of treatment. Such method of treatment is also referred to as combination therapy.

"Combination therapy" (or "co-therapy") includes the administration of a nucleic acid molecule of the invention and at least a second or further agent as part of a specific treatment regimen intended to provide the beneficial effect from the co-action of these therapeutic agents, i. e. the medicament of the present invention and said second or further agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may be, but generally is not, intended to encompass the administration of two or more of these therapeutic agents as part of separate monotherapy regimens.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically. Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In accordance therewith such further therapeutically or pharmaceutically active agent is also administered to the subject. In an embodiment, the further therapeutically or pharmaceutically active agent is administered prior, together with or after the nucleic acid molecule of the invention. In an embodiment the further therapeutically or pharmaceutically active agent is one selected from the group comprising taxane derivates such as docetaxel, paclitaxel (see, Q. F. Ye, et al., "siRNA-mediated silencing of Notch-1 enhances docetaxel induced mitotic arrest and apoptosis in prostate cancer cells," Asian Pac. J. Cancer Prev. 13(6), 2485 (2012), C. C. Zhang, et al., "Synergistic effect of the gamma-secretase inhibitor PF-03084014 and docetaxel in breast cancer models," Stem Cells Transl. Med. 2(3), 233 (2013), K. A. Hassan, et al., "Notch pathway activity identifies cells with cancer stem cell-like properties and correlates with worse survival in lung adenocarcinoma," Clin. Cancer Res. 19(8), 1972 (2013), Y. P. Liu, et al., "Cisplatin selects for multidrug-resistant CD133+ cells in lung adenocarcinoma by activating Notch signaling," Cancer Res. 73(1), 406 (2013), and S. Zang, et al., "RNAi-mediated knockdown of Notch-1 leads to cell growth inhibition and enhanced chemosensitivity in human breast cancer," Oncol. Rep. 23(4), 893 (2010)), platinum derivatives such as cisplatin and oxaliplatin (see, K. A. Hassan, et al., "Notch pathway activity identifies cells with cancer stem cell-like properties and correlates with worse survival in lung adenocarcinoma," Clin. Cancer Res. 19(8), 1972 (2013) and Z. P. Zhang, et al., "Correlation of Notch1 expression and activation to cisplatin-sensitivity of head and neck squamous cell carcinoma," Ai. Zheng. 28(2), 100 (2009)), Nucleoside analogues such as 5-fluorouracil (see, R. D. Meng, et al., "gamma-Secretase inhibitors abrogate oxaliplatin-induced activation of the Notch-1 signaling pathway in colon cancer cells resulting in enhanced chemosensitivity," Cancer Res. 69(2), 573 (2009)), topoisomerase I inhibitors such as irinotecan (see, R. D. Meng, et al., "gamma-Secretase inhibitors abrogate oxaliplatin-induced activation of the Notch-1 signaling pathway in colon cancer cells resulting in enhanced chemosensitivity," Cancer Res. 69(2), 573 (2009), intercalating substances such as doxorubicin (see, Y. P. Liu, et al., "Cisplatin selects for multidrug-resistant CD133+ cells in lung adenocarcinoma by activating Notch signaling," Cancer Res. 73(1), 406 (2013)), nucleoside analogues such as gemcitabine (see, X. Du, et al., "Notch1 contributes to chemoresistance to gemcitabine and serves as an unfavorable prognostic indicator in pancreatic cancer," World J. Surg. 37(7), 1688 (2013), S. Yabuuchi, et al., "Notch signaling pathway targeted therapy suppresses tumor progression and metastatic spread in pancreatic cancer," Cancer Lett. 335(1), 41 (2013), and S. Richter, et al., "A phase I study of the oral gamma secretase inhibitor R04929097 in combination with gemcitabine in patients with advanced solid tumors (PHL-078/CTEP 8575)," Invest New Drugs (2013)), synthetic glucocorticoids such as dexamethasone (see, Q. Zhou, et al., "The roles of Notch1 expression in the migration of intrahepatic cholangiocarcinoma," BMC. Cancer 13, 244 (2013)) and alkylating agents such as temozolomide (see, C. A. Gilbert, M. C. Daou, R. P. Moser, and A. H. Ross, "Gamma-secretase inhibitors enhance temozolomide treatment of human gliomas by inhibiting neurosphere repopulation and xenograft recurrence," Cancer Res. 70(17), 6870 (2010)).

An embodiment of the method of the invention whereby the method of treatment is a combination therapy is one where rather than administering at least one further pharmaceutically or therapeutically active agent the subject receives radiotherapy.

Radiotherapy (also referred to X-ray therapy or irradiation) is the use of ionizing radiation to kill cancer cells. Radiotherapy is used in the medical art to treat almost every type of solid tumor. Irradiation is also used to treat leukemia and lymphoma. Radiotherapy injures or destroys cells in the area being treated by damaging their genetic material, making it impossible for these cells to continue to grow and divide. The effects of radiotherapy are localized and confined to the region being treated. Radiation dose to each site depends on a number of factors, including the radiosensitivity of each cancer type and whether there are tissues and organs nearby that may be damaged by radiation. The goal of radiotherapy is to damage as many cancer cells as possible, while limiting harm to nearby healthy tissue.

In a further embodiment of the method of the invention for the treatment and/or prevention of a disease comprising the administration of a nucleic acid molecule of the invention, preferably a siRNA of the invention, to a subject, whereby the disease is preferably cancer and more preferably a cancer as disclosed herein, the method is actually an adjunct therapy of adjunctive therapy. The purpose of such adjunct therapy is to assist a primary treatment, preferably a primary cancer treatment.

The nucleic acid molecule of the invention is useful in and may be used in a method for restoring drug sensitivity of cancer cells. In an embodiment, the method comprises the administration of a nucleic acid of the invention to a subject, whereby the subject is suffering from a disease, preferably cancer, and cancer cells which are involved in the disease and/or cells which are to be addressed, damaged and/or destroyed by any therapy supplied to the subject or by any pharmaceutically or therapeutically active agent administered to the subject in the treatment of the disease, are not or no longer susceptible to such therapy and/or such pharmaceutically or therapeutically active agent. Typically, after administration of the nucleic acid molecule of the invention, said cells become susceptible to such therapy and/or pharmaceutically or therapeutically active agent again, at least to a therapeutically and/or pharmaceutically relevant level. Such therapy is preferably cancer therapy including, but not limited to, cytostatic based therapy and radiation therapy, and such pharmaceutically or therapeutically active agent is one used in cancer therapy. Preferably, the nucleic acid molecule of the invention is a siRNA of the invention.

Insofar, the method for restoring drug sensitivity of cancer cells is a method for re-sensitizing cancer cells which are not or no longer susceptible to cancer therapy and/or pharmaceutically or therapeutically active agent used in cancer therapy. It will also be acknowledged that the method for restoring drug sensitivity of cancer is an adjunct therapy for a method for the treatment of cancer.

It will be acknowledged that what is disclosed herein in connection with the method for the treatment and/or prevention of a disease is equally applicable to the method for restoring drug sensitivity of cancer cells. This applies in particular to the aspects of such method related to the subject of the method, the administration and administration routes of the nucleic acid of the invention and the like. Insofar, the method for restoring drug sensitivity of cancer cells is an embodiment of the method for the treatment and/or prevention of a disease. Preferred forms of cancer which may establish a resistance to a therapy typically applied to a subject suffering from such forms of cancer, are the followings:

Esophageal cancer (see, Streppel, E. A. Montgomery, and A. Maitra, "New Advances in the Pathogenesis and Progression of Barrett's Esophagus," *Curr. Mol. Med.* (2013)), oral squamous cell carcinoma (see, R. Yoshida, et al., "The pathological significance of Notch1 in oral squamous cell carcinoma," *Lab Invest* (2013)), head and neck cancer (see, J. T. Lin, et al., "Association of high levels of Jagged-1 and Notch-1 expression with poor prognosis in head and neck cancer," *Ann. Surg. Oncol.* 17(11), 2976 (2010)), tongue cancer (see Y. H. Joo, C. K. Jung, M. S. Kim, and D. I. Sun, "Relationship between vascular endothelial growth factor and Notch1 expression and lymphatic metastasis in tongue cancer," *Otolaryngol. Head Neck Surg.* 140(4), 512 (2009)), leukemia (see E. Kanamori, et al., "Flow cytometric analysis of Notch1 and Jagged1 expression in normal blood cells and leukemia cells," *Exp. Ther. Med.* 4(3), 397 (2012); and Zhang J et al. (J. Zhang, et al., "Prognostic impact of delta-like ligand 4 and Notch1 in acute myeloid leukemia," *Oncol. Rep.* 28(4), 1503 (2012)), renal cell carcinoma (see, Q. Ai, et al., "High-level expression of Notch1 increased the risk of metastasis in Ti stage clear cell renal cell carcinoma," *PLoS. One.* 7(4), e35022 (2012) and J. Sjolund, et al., "The notch and TGF-beta signaling pathways contribute to the aggressiveness of clear cell renal cell carcinoma," *PLoS. One.* 6(8), e23057 (2011)), gastric cancer (see, T. S. Yeh, et al., "The activated Notch1 signal pathway is associated with gastric cancer progression through cyclooxygenase-2," *Cancer Res.* 69(12), 5039 (2009), and Y. Sun, et al., "Differential Notch1 and Notch2 expression and frequent activation of Notch signaling in gastric cancers," *Arch. Pathol. Lab Med.* 135(4), 451 (2011)), colon adenocarcinoma (see, M. Reedijk, et al., "Activation of Notch signaling in human colon adenocarcinoma," *Int J. Oncol.* 33(6), 1223 (2008) and M. Reedijk, et al., "Activation of Notch signaling in human colon adenocarcinoma," *Int J. Oncol.* 33(6), 1223 (2008)), endometrial cancer/uterine corpus (see Y. Mitsuhashi, et al., "Prognostic significance of Notch signalling molecules and their involvement in the invasiveness of endometrial carcinoma cells," *Histopathology* 60(5), 826 (2012)), cervical cancer/uterine cervix (see, L. Santos, et al., "Identification of differential expressed transcripts in cervical cancer of Mexican patients," *Tumour. Biol.* 32(3), 561 (2011)), intrahepatic cholangiocarcinoma (see, Q. Zhou, et al., "The roles of Notch1 expression in the migration of intrahepatic cholangiocarcinoma," *BMC. Cancer* 13, 244 (2013), and S. Zender, et al., "A critical role for notch signaling in the formation of cholangiocellular carcinomas," *Cancer Cell* 23(6), 784 (2013)), hepatocellular carcinoma (see, A. Villanueva, et al., "Notch signaling is activated in human hepatocellular carcinoma and induces tumor formation in mice," *Gastroenterology* 143(6), 1660 (2012), and R. Fan, et al., "Cooperation of deregulated Notch signaling and Ras pathway in human hepatocarcinogenesis," *J. Mol. Histol.* 42(5), 473 (2011)), osteosarcoma (see, J. Yang and W. Zhang, "New molecular insights into osteosarcoma targeted therapy," *Curr. Opin. Oncol.* 25(4), 398 (2013)), urinary bladder carcinoma (see, A. G. Abdou, et al., "Immunohistochemical analysis of the role and relationship between Notch-1 and Oct-4 expression in urinary bladder carcinoma," *APMIS* (2013)), malignant melanoma (see, C. S. Muller, "Notch signaling and malignant melanoma," *Adv. Exp. Med. Biol.* 727, 258 (2012)), thyroid cancer (see, H. S. Park, et al., "Notch1 receptor as a marker of lymph node metastases in papillary thyroid cancer," *Cancer Sci.* 103(2), 305 (2012)), lung adenocarcinoma (see K. A. Hassan, et al., "Notch pathway activity identifies cells with cancer stem cell-like properties and correlates with worse survival in lung adenocarcinoma," *Clin. Cancer Res.* 19(8), 1972 (2013), and B. Westhoff, et al., "Alterations of the Notch pathway in lung cancer," *Proc. Natl. Acad. Sci. U. S. A* 106(52), 22293 (2009)), prostata cancer (see, H. Zhu, et al., "Elevated Jagged-1 and Notch-1 expression in high grade and metastatic prostate cancers," *Am. J. Transl. Res.* 5(3), 368 (2013)) and M. Kashat, et al., "Inactivation of AR and Notch-1 signaling by miR-34a attenuates prostate cancer aggressiveness," *Am. J Transl. Res.* 4(4), 432 (2012)), breast cancer (see, J. Speiser, et al., "Notch-1 and Notch-4 biomarker expression in triple-negative breast cancer," *Int J. Surg. Pathol.* 20(2), 139 (2012), and S. Mittal, et al., "Cooperation of Notch and Ras/MAPK signaling pathways in human breast carcinogenesis," *Mol. Cancer* 8, 128 (2009)), ovarian cancer (see, S. L. Rose, M. Kunnimalaiyaan, J. Drenzek, and N. Seiler, "Notch 1 signaling is active in ovarian cancer," *Gynecol. Oncol.* 117(1), 130 (2010)), pancreatic cancer (see, F. H. Sarkar, S. Banerjee, and Y. Li, "Pancreatic cancer: pathogenesis, prevention and treatment," Toxicol. Appl. Pharmacol. 224(3), 326 (2007), O. JP De La, et al., "Notch and Kras reprogram pancreatic acinar cells to ductal intraepithelial neoplasia," Proc. Natl. Acad. Sci. U. S. A 105(48), 18907 (2008), E. Ristorcelli and D. Lombardo, "Targeting Notch signaling in pancreatic cancer," Expert. Opin. Ther. Targets. 14(5), 541 (2010), Z. Wang, et al., "Notch-1 down-regulation by curcumin is associated with the inhibition of cell growth and the induction of apoptosis in pancreatic cancer cells," Cancer 106(11), 2503 (2006), P. Buchler, et al., "The Notch signaling pathway is related to neurovascular progression of pancreatic cancer," Ann. Surg. 242(6), 791, discussion (2005), Z.

Wang, et al., "Down-regulation of Notch-1 contributes to cell growth inhibition and apoptosis in pancreatic cancer cells," Mol. Cancer Ther. 5(3), 483 (2006), Z. Wang, et al., "Down-regulation of notch-1 inhibits invasion by inactivation of nuclear factor-kappaB, vascular endothelial growth factor, and matrix metalloproteinase-9 in pancreatic cancer cells," Cancer Res. 66(5), 2778 (2006)), and glioma (see, X. Zhang, et al., "Notch1 promotes glioma cell migration and invasion by stimulating beta-catenin and NF-kappaB signaling via AKT activation," Cancer Sci. 103(2), 181 (2012), L. Jiang, et al., "Notch1 expression is upregulated in glioma and is associated with tumor progression," J. Clin. Neurosci. 18(3), 387 (2011), J. Li, et al., "Notch1 is an independent prognostic factor for patients with glioma," J. Surg. Oncol. 103(8), 813 (2011), and S. Puget, et al., "Candidate genes on chromosome 9q33-34 involved in the progression of childhood ependymomas," J. Clin. Oncol. 27(11), 1884 (2009)).

Resistance of cancer cells which can be overcome by the method for restoring drug sensitivity is Notch 1-induced resistance and Notch 1-induced chemoresistance in particular. Insofar, the method for restoring drug sensitivity of cancer cells is a method for reversing Notch 1-induced resistance and Notch 1-induced chemoresistance in particular. Whether a cell and a cancer cell in particular is resistant to chemotherapeutics may be determined by routine tests known to a person skilled in the art such as the MMT (3-(4,5-dimethylthiazol-2-yl)-2,5-diphenyltetrazolium bromide)-assay and flow cytometry.

The MMT (3-(4,5-dimethylthiazol-2-yl)-2,5-diphenyltetrazolium bromide)-assay measures the reduction of MTT by cellular enzymes. By measuring this metabolic activity via NAD(P)H-dependent enzymes it is possible to estimate the number of viable cells. Tetrazolium dye assays allow measurements of both cytotoxicity and cytostatic activity of chemotherapeutic agents.

In flow cytometry cells are suspended in a fluid-stream and pass through a detector. Using Laser-technology, it allows to determine the number of cells and to identify biomarkers. A large number of particles can be simultaneous analyzed for biophysical and chemical parameters. Using this technique, it is possible to discriminate viable from apoptotic cells to measure the effects of pharmaceutical agents.

Notch 1 induced chemoresistance is, for example, described in K. M. Capaccione and S. R. Pine (K. M. Capaccione and S. R. Pine, "The Notch signaling pathway as a mediator of tumor survival," Carcinogenesis 34(7), 1420 (2013)). From this and other references it is plausible that by inhibition the expression of Notch 1 and thus by using the nucleic acid molecule of the invention Notch 1 induced chemoresistance can be overcome. Such other references include, but are not limited to Ye, Q F et al. (Q. F. Ye, et al., "siRNA-mediated silencing of Notch-1 enhances docetaxel induced mitotic arrest and apoptosis in prostate cancer cells," Asian Pac. J. Cancer Prev. 13(6), 2485 (2012)) for prostate cancer, Zhang C C et al. (C. C. Zhang, et al., "Synergistic effect of the gamma-secretase inhibitor PF-03084014 and docetaxel in breast cancer models," Stem Cells Transl. Med. 2(3), 233 (2013)) or Zang S et al. (S. Zang, et al., "RNAi-mediated knockdown of Notch-1 leads to cell growth inhibition and enhanced chemosensitivity in human breast cancer," Oncol. Rep. 23(4), 893 (2010)) for breast cancer, Hassan K A et al. (K. A. Hassan, et al., "Notch pathway activity identifies cells with cancer stem cell-like properties and correlates with worse survival in lung adenocarcinoma," Clin. Cancer Res. 19(8), 1972 (2013)) for lung cancer, Zhang Z P et al. (Z. P. Zhang, et al., "Correlation of Notch1 expression and activation to cisplatin-sensitivity of head and neck squamous cell carcinoma," Ai. Zheng. 28(2), 100 (2009)) for squamous cell carcinomas, Meng R D et al. (R. D. Meng, et al., "gamma-Secretase inhibitors abrogate oxaliplatin-induced activation of the Notch-1 signaling pathway in colon cancer cells resulting in enhanced chemosensitivity," Cancer Res. 69(2), 573 (2009)) for colon cancer, Liu Y P et al. (Y. P. Liu, et al., "Cisplatin selects for multidrug-resistant CD133+ cells in lung adenocarcinoma by activating Notch signaling," Cancer Res. 73(1), 406 (2013)) for non-small lung cancer, Du X et al. (X. Du, et al., "Notch1 contributes to chemoresistance to gemcitabine and serves as an unfavorable prognostic indicator in pancreatic cancer," World J. Surg. 37(7), 1688 (2013)) or Yabuuchi S et al (S. Yabuuchi, et al., "Notch signaling pathway targeted therapy suppresses tumor progression and metastatic spread in pancreatic cancer," Cancer Lett. 335(1), 41 (2013)) for pancreatic cancer, Zhou Q et al. (Q. Zhou, et al., "The roles of Notch1 expression in the migration of intrahepatic cholangiocarcinoma," BMC. Cancer 13, 244 (2013)) for leukemia and T-cell acute lymphoblastic leukemia in particular, and Gilbert Calif. et al. (C. A. Gilbert, M. C. Daou, R. P. Moser, and A. H. Ross, "Gamma-secretase inhibitors enhance temozolomide treatment of human gliomas by inhibiting neurosphere repopulation and xenograft recurrence," Cancer Res. 70(17), 6870 (2010)) for glioma.

Apart from overcoming Notch 1 induced resistance, the nucleic acid molecule of the invention is also suitable to overcome resistance to radiation as evident from Hovinga K E (K. E. Hovinga, et al., "Inhibition of notch signaling in glioblastoma targets cancer stem cells via an endothelial cell intermediate," Stem Cells 28(6), 1019 (2010)) and Wang J et al. (J. Wang, et al., "Notch promotes radioresistance of glioma stem cells," Stem Cells 28(1), 17 (2010)).

The present invention is further illustrated by the figures, examples and the sequence listing from which further features, embodiments and advantages may be taken, wherein FIGS. 1A-1B are diagrams indicating the relative expression of Notch 1 upon transfection of C4-2 cells using various siRNAs;

Figure 4:
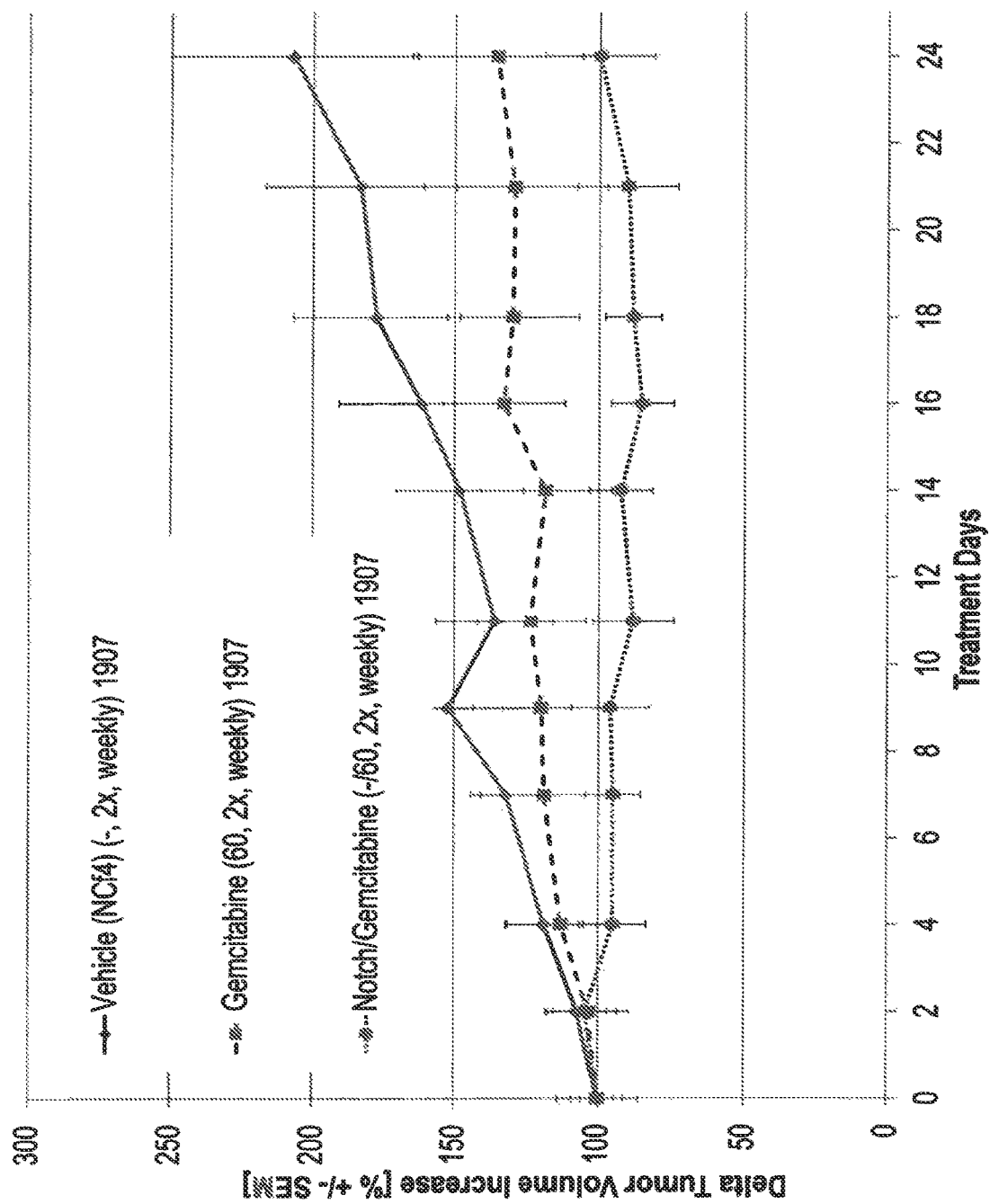
Figure 5:
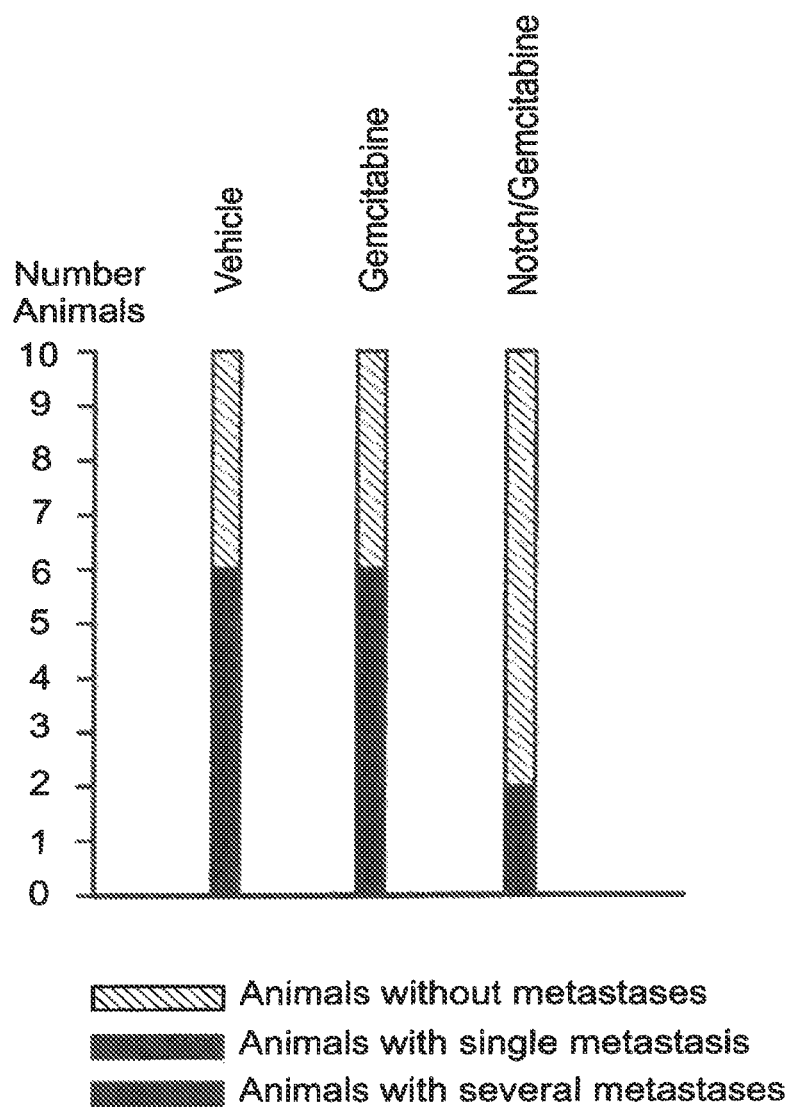

FIG. 4 is a diagram showing the relative increase in tumour volume (indicated as %±SEM) in a xenograft mouse model using PANC-1 cells; and FIG. 5 is a diagram showing the number of animals in a PANC-1 orthotopic tumor model without metastases, with several metastases and with single metastases upon treatment of the animal model with control, gemcitabine or a combination of gemcitabine and nanocarrier comprising the siRNA of the invention.

EXAMPLE 1: MATERIALS AND METHODS siRNAs

The siRNAs represented in Table 1 were prepared using standard chemical synthesis:

TABLE 1

| duplex ID | SS ID | synthesized sense strand sequence (5'-3') | AS ID | synthesized antisense strand sequence (5'-3') |
|---|---|---|---|---|
| XD-00388 | X01324 | GCGCUCGCCGCACGAGGCCdTdT | X01325 | GGCCUCGUGCGGCGAGCGCdTdT |
| XD-00389 | X01326 | CUUCGUGGGCCCGCGAUGCdTdT | X01327 | GCAUCGCGGGCCCACGAAGdTdT |
| XD-00390 | X01328 | AAGAACGCCGGGACAUGCCdTdT | X01329 | GGCAUGUCCCGGCGUUCUUdTdT |
| XD-00391 | X01330 | CAUGCCACGUGGUGGACCGdTdT | X01331 | CGGUCCACCACGUGGCAUGdTdT |
| XD-00392 | X01332 | CGGAGUACAAGUGCCGCUGdTdT | X01333 | CAGCGGCACUUGUACUCCGdTdT |
| XD-00393 | X01334 | UGCCGGCAGGAUGUCAACGdTdT | X01335 | CGUUGACAUCCUGCCGGCAdTdT |
| XD-00394 | X01336 | GAGGGUGUGCACUGCGAGGdTdT | X01337 | CCUCGCAGUGCACACCCUCdTdT |
| XD-00395 | X01338 | GGACCCAACACUUACACCUdTdT | X01339 | AGGUGUAAGUGUUGGGUCCdTdT |
| XD-00396 | X01340 | CUGCAAGGACGGCGUCGCCdTdT | X01341 | GGCGACGCCGUCCUUGCAGdTdT |
| XD-00397 | X01342 | GCACGUGUAUUGACGACGUdTdT | X01343 | ACGUCGUCAAUACACGUGCdTdT |
| XD-00398 | X01344 | CACGUGUAUUGACGACGUUdTdT | X01345 | AACGUCGUCAAUACACGUGdTdT |
| XD-00399 | X01346 | ACGUGUAUUGACGACGUUGdTdT | X01347 | CAACGUCGUCAAUACACGUdTdT |
| XD-00400 | X01348 | GGACGAGUGCUCACCCAGCdTdT | X01349 | GCUGGGUGAGCACUCGUCCdTdT |
| XD-00401 | X01350 | CCAUCAAGCGUGCCGCCGAdTdT | X01351 | UCGGCGGCACGCUUGAUGGdTdT |
| XD-00402 | X01352 | CCGGUUCGAGGAGCCCGUGdTdT | X01353 | CACGGGCUCCUCGAACCGGdTdT |
| XD-00403 | X01354 | CCGGGACAUCACGGAUCAUdTdT | X01355 | AUGAUCCGUGAUGUCCCGGdTdT |
| XD-00404 | X01356 | GACAUCGCACAGGAGCGCAdTdT | X01357 | UGCGCUCCUGUGCGAUGUCdTdT |
| XD-00405 | X01358 | CAGAGCGGCAUGGUGCCGAdTdT | X01359 | UCGGCACCAUGCCGCUCUGdTdT |
| XD-00406 | X01360 | CAUGGUGCCGAACCAAUACdTdT | X01361 | GUAUUGGUUCGGCACCAUGdTdT |
| XD-00407 | X01362 | UGGUGCCGAACCAAUACAAdTdT | X01363 | UUGUAUUGGUUCGGCACCAdTdT |
| XD-00408 | X01364 | CUCGCCUGUGGACAACACCdTdT | X01365 | GGUGUUGUCCACAGGCGAGdTdT |
| XD-00409 | X01366 | GACCAGUGGUCCAGCUCGUdTdT | X01367 | ACGAGCUGGACCACUGGUCdTdT |
| XD-00410 | X01368 | CAUUCCAACGUCUCCGACUdTdT | X01369 | AGUCGGAGACGUUGGAAUGdTdT |
| XD-00411 | X01370 | AUUCCAACGUCUCCGACUGdTdT | X01371 | CAGUCGGAGACGUUGGAAUdTdT |
| XD-00412 | X01372 | UUCCAACGUCUCCGACUGGdTdT | X01373 | CCAGUCGGAGACGUUGGAAdTdT |
| XD-00413 | X01374 | CAACGUCUCCGACUGGUCCdTdT | X01375 | GGACCAGUCGGAGACGUUGdTdT |
| XD-00414 | X01376 | ACGUCUCCGACUGGUCCGAdTdT | X01377 | UCGGACCAGUCGGAGACGUdTdT |

The above Table 1 is represented again as Table 1a including the sequence identifiers.

TABLE 1a

| duplex ID | SS ID | synthesized sense strand sequence (5'-3') | AS ID | synthesized antisense strand sequence (5'-3') |
|---|---|---|---|---|
| XD-00388 | X01324 | GCGCUCGCCGCACGAGGCCdTdT (SEQ ID NO: 73) | X01325 | GGCCUCGUGCGGCGAGCGCdTdT (SEQ ID NO: 74) |
| XD-00389 | X01326 | CUUCGUGGGCCCGCGAUGCdTdT (SEQ ID NO: 75) | X01327 | GCAUCGCGGGCCCACGAAGdTdT (SEQ ID NO: 76) |
| XD-00390 | X01328 | AAGAACGCCGGGACAUGCCdTdT (SEQ ID NO: 77) | X01329 | GGCAUGUCCCGGCGUUCUUdTdT (SEQ ID NO: 78) |
| XD-00391 | X01330 | CAUGCCACGUGGUGGACCGdTdT (SEQ ID NO: 79) | X01331 | CGGUCCACCACGUGGCAUGdTdT (SEQ ID NO: 80) |
| XD-00392 | X01332 | CGGAGUACAAGUGCCGCUGdTdT (SEQ ID NO: 81) | X01333 | CAGCGGCACUUGUACUCCGdTdT (SEQ ID NO: 82) |
| XD-00393 | X01334 | UGCCGGCAGGAUGUCAACGdTdT (SEQ ID NO: 83) | X01335 | CGUUGACAUCCUGCCGGCAdTdT (SEQ ID NO: 84) |
| XD-00394 | X01336 | GAGGGUGUGCACUGCGAGGdTdT (SEQ ID NO: 85) | X01337 | CCUCGCAGUGCACACCCUCdTdT (SEQ ID NO: 86) |
| XD-00395 | X01338 | GGACCCAACACUUACACCUdTdT (SEQ ID NO: 87) | X01339 | AGGUGUAAGUGUUGGGUCCdTdT (SEQ ID NO: 88) |
| XD-00396 | X01340 | CUGCAAGGACGGCGUCGCCdTdT (SEQ ID NO: 89) | X01341 | GGCGACGCCGUCCUUGCAGdTdT (SEQ ID NO: 90) |
| XD-00397 | X01342 | GCACGUGUAUUGACGACGUdTdT (SEQ ID NO: 91) | X01343 | ACGUCGUCAAUACACGUGCdTdT (SEQ ID NO: 92) |
| XD-00398 | X01344 | CACGUGUAUUGACGACGUUdTdT (SEQ ID NO: 93) | X01345 | AACGUCGUCAAUACACGUGdTdT (SEQ ID NO: 94) |
| XD-00399 | X01346 | ACGUGUAUUGACGACGUUGdTdT (SEQ ID NO: 95) | X01347 | CAACGUCGUCAAUACACGUdTdT (SEQ ID NO: 96) |
| XD-00400 | X01348 | GGACGAGUGCUCACCCAGCdTdT (SEQ ID NO: 97) | X01349 | GCUGGGUGAGCACUCGUCCdTdT (SEQ ID NO: 98) |
| XD-00401 | X01350 | CCAUCAAGCGUGCCGCCGAdTdT (SEQ ID NO: 99) | X01351 | UCGGCGGCACGCUUGAUGGdTdT (SEQ ID NO: 100) |
| XD-00402 | X01352 | CCGGUUCGAGGAGCCCGUGdTdT (SEQ ID NO: 101) | X01353 | CACGGGCUCCUCGAACCGGdTdT (SEQ ID NO: 102) |
| XD-00403 | X01354 | CCGGGACAUCACGGAUCAUdTdT (SEQ ID NO: 103) | X01355 | AUGAUCCGUGAUGUCCCGGdTdT (SEQ ID NO: 104) |
| XD-00404 | X01356 | GACAUCGCACAGGAGCGCAdTdT (SEQ ID NO: 105) | X01357 | UGCGCUCCUGUGCGAUGUCdTdT (SEQ ID NO: 106) |
| XD-00405 | X01358 | CAGAGCGGCAUGGUGCCGAdTdT (SEQ ID NO: 107) | X01359 | UCGGCACCAUGCCGCUCUGdTdT (SEQ ID NO: 108) |
| XD-00406 | X01360 | CAUGGUGCCGAACCAAUACdTdT (SEQ ID NO: 109) | X01361 | GUAUUGGUUCGGCACCAUGdTdT (SEQ ID NO: 110) |
| XD-00407 | X01362 | UGGUGCCGAACCAAUACAAdTdT (SEQ ID NO: 111) | X01363 | UUGUAUUGGUUCGGCACCAdTdT (SEQ ID NO: 112) |
| XD-00408 | X01364 | CUCGCCUGUGGACAACACCdTdT (SEQ ID NO: 113) | X01365 | GGUGUUGUCCACAGGCGAGdTdT (SEQ ID NO: 114) |
| XD-00409 | X01366 | GACCAGUGGUCCAGCUCGUdTdT (SEQ ID NO: 115) | X01367 | ACGAGCUGGACCACUGGUCdTdT (SEQ ID NO: 116) |
| XD-00410 | X01368 | CAUUCCAACGUCUCCGACUdTdT (SEQ ID NO: 117) | X01369 | AGUCGGAGACGUUGGAAUGdTdT (SEQ ID NO: 118) |
| XD-00411 | X01370 | AUUCCAACGUCUCCGACUGdTdT (SEQ ID NO: 119) | X01371 | CAGUCGGAGACGUUGGAAUdTdT (SEQ ID NO: 120) |
| XD-00412 | X01372 | UUCCAACGUCUCCGACUGGdTdT (SEQ ID NO: 121) | X01373 | CCAGUCGGAGACGUUGGAAdTdT (SEQ ID NO: 122) |

TABLE 1a-continued

| duplex ID | SS ID | synthesized sense strand sequence (5'-3') | AS ID | synthesized antisense strand sequence (5'-3') |
|---|---|---|---|---|
| XD-00413 | X01374 | CAACGUCUCCGACUGGUCCdTdT (SEQ ID NO: 123) | X01375 | GGACCAGUCGGAGACGUUGdTdT (SEQ ID NO: 124) |
| XD-00414 | X01376 | ACGUCUCCGACUGGUCCGAdTdT (SEQ ID NO: 125) | X01377 | UCGGACCAGUCGGAGACGUdTdT (SEQ ID NO: 126) |

Out of this group the following some siRNAs were modified. The modified siRNAs are indicated in Table 2.

TABLE 2 a) XD-00395 sense strand:     5' GGACCCAACACUUACACCUdTdT 3' (SEQ ID NO: 87)
antisense strand: 5' AGGUGUAAGUGUUGGGUCCdTdT 3' (SEQ ID NO: 88)

b) XD-00404 sense strand:     5' GACAUCGCACAGGAGCGCAdTdT 3' (SEQ ID NO: 105)
antisense strand: 5' UGCGCUCCUGUGCGAUGUCdTdT 3' (SEQ ID NO: 106)

c) XD-00406 sense strand:     5' CAUGGUGCCGAACCAAUACdTdT 3' (SEQ ID NO: 109)
antisense strand: 5' GUAUUGGUUCGGCACCAUGdTdT 3' (SEQ ID NO: 110)

d) XD-00407 sense strand:     5' UGGUGCCGAACCAAUACAAdTdT 3' (SEQ ID NO: 111)
antisense strand: 5' UUGUAUUGGUUCGGCACCAdTdT 3' (SEQ ID NO: 112)

e) XD-00409 sense strand:     5' GACCAGUGGUCCAGCUCGUdTdT 3' (SEQ ID NO: 115)
antisense strand: 5' ACGAGCUGGACCACUGGUCdTdT 3' (SEQ ID NO: 116)

f) XD-00410 sense strand:     5' CAUUCCAACGUCUCCGACUdTdT 3' (SEQ ID NO: 117)
antisense strand: 5' AGUCGGAGACGUUGGAAUGdTdT 3' (SEQ ID NO: 118)

Fully Stabilized siRNA siRNAs XD-00404 and XD-00409 of Table 2 were subject to full stabilization. The thus fully stabilized siRNAs are as follow.

a) XD-00409
(SEQ ID NO: 70)
sense strand:
5' $\underline{GA}c\underline{C}a\underline{Gu}\underline{Gg}\underline{Uc}\underline{Ca}\underline{Gc}\underline{Uc}\underline{Gu}dT_SdT$ 3' antisense strand:
(SEQ ID NO: 69)
5' ac$\underline{Ga}\underline{Gc}\underline{Ug}\underline{Ga}\underline{Cc}\underline{Ac}\underline{Ug}\underline{Gu}\underline{C}dT_SdT$ 3' b) XD-00404
sense strand:
(SEQ ID NO: 128)
5' $\underline{GA}c\underline{Au}\underline{Cg}\underline{Ca}\underline{Ca}\underline{Gg}\underline{Ag}\underline{Cg}\underline{C}adT_SdT$ 3' antisense strand:
(SEQ ID NO: 127)
5' ug$\underline{Cg}\underline{Cu}\underline{Cc}\underline{Ug}\underline{Ug}\underline{Cg}\underline{Au}\underline{Gu}\underline{C}dT_SdT$ 3', wherein a minor nucleotide indicates that the nucleotide is 2'-F modified and an underlined nucleotide indicates that the nucleotide is 2'-O-methyl modified and
wherein dTsdT indicates that at the 3' end a dinucleotide is attached consisting of two dTs, wherein said two dTs are covalently linked through a phosphorothioate bond Intermediately Stabilized siRNA The intermediately stabilized siRNAs differ from the fully stabilized siRNAs such that lack the dTsdT overhang and did not exhibit any 2'-F modification.

Cultivation of C4-2 Cells

C4-2 cells were cultivated according to standard procedures described for this cell line using RPMI 1640 medium.

Transfection of C4-2 Cells

C4-2 cells were transfected with various concentrations of siRNA using Lipofectamine 2000. Concentrations of siRNA were 50 nM, 10 nM, 1 nM or 0.1 nM in the transfection experiment. Incubation time was 24 h. Otherwise a standard protocol was used. Transfection efficiency was determined by measuring housekeeper siRNA; transfection efficacy was at least 93% in all cases.

Determining the IC 50 of siRNAs

IC50 values were determined using standard procedures. More specifically, siRNA concentration was determined at which expression of Notch 1 mRNA was decreased to 50% using C4-2 cells transfected as described using the various siRNAs indicated.

Nanocarrier

For preparation of the nanocarrier, which is a perfluorocarbon nanocarrier, perfluoroocytlbromide (Perflubron) was emulsified with a mixture of phospholipids. One gram of the mixture contains phosphatidylcholine (980 mg), sphingomyelin (10 mg), cholesterol (5 mg), lysophoshatidylcholine (5 mg), in distilled water and 75 mM sodium dihydrogen phosphate ($NaH_2PO_4$) buffer. To gain 1000 µl of the perfluorcarbon nanocarrier, 475 µl perfluorooctylbromide, 36 mg phospholipids, 200 µl 75 mM $NaH_2PO_4$ at pH 7.4 and 325 µl distilled water was used.

First, phospholipids, sodium dihydrogen phosphate buffer and distilled water were mixed and subsequently the perfluorcarbon (PFC) solution was adjoined. Within 40 seconds, the composite had to be mixed by a shaker for 60 s and without any interruption homogenized twice by an ultrasonic device at a frequency of 1100 kHz for 120 s with intervals of 30 s. The sonication unit is kept at a temperature of 4° C. For the final emulsion of the otherwise insoluble PFC, the mixture is given into a high pressure homogenizer. Within six passages of homogenization at 2500 bar the milky composite turns into a transparent, bluish emulsion. This change to transparency is a macroscopic marker for the turn of the perfluorcarbon particles size below the visible wavelengths. The lowest visible wavelength (blue/violet) of $\lambda=400$ nm defines the particles size as $\lambda/2$ when the mixture becomes transparent. Four additional cycles of homogenization are added at this point. The particles size was measured in electron microscopy as 50 nm (mean) with all particles below 100 nm. To gain the functional nanocarrier, 4 mg holotransferrin is solved in 60 µl sterile 0.9% NaCl. Directly afterwards, the transferrin is homogenized for 2 s by the cooled ultrasonic device. The solved transferrin is added to 1000 µl perfluorocarbon emulsion to obtain an end concentration of 4 mg/ml. Again, the compound is directly put on a shaker for 30 s.

This nanocarrier is also referred to as unloaded carrier or NCf4.

Notch siRNA-Loaded Nanocarriers

Notch siRNA-loaded nanocarriers were prepared based on the Nanocarrier described above. For loading purposes the desired siRNA species was added to the nanocarriers and the thus obtained mixture subject to homogenization by ultrasound using 500 W for 15 s.

Animal Study—Xenograft Model

Sixty female athymic nude Foxn1$^{nu}$ mice bearing tumours from subcutaneously inoculated PANC-1 human pancreatic tumours were selected from a pool of 112. This animal model is an established animal model for pancreatic cancer and pancreatic tumor, respectively, using PANC-1 cell line which has been first described by Lieber M et al. (M. Lieber, et al., "Establishment of a continuous tumor-cell line (panc-1) from a human carcinoma of the exocrine pancreas," Int J. Cancer 15(5), 741 (1975)), and biochemically as well as morphologically characterized by Madden M E and Sarras M P (M. E. Madden and M. P. Sarras, Jr., "Morphological and biochemical characterization of a human pancreatic ductal cell line (PANC-1)," Pancreas 3(5), 512 (1988)). Such cell line and the established animal model using such cell line has been used in the evaluation of anti-cancer agents Schultz R M et al. (R. M. Schultz, et al., "Evaluation of new anticancer agents against the MIA PaCa-2 and PANC-1 human pancreatic carcinoma xenografts," Oncol. Res. 5(6-7), 223 (1993)).

Thirty-three days post-inoculation, the mice were randomised by tumour size into six groups of ten (Day 0).

Mice in each group were treated twice weekly with Vehicle Control (unloaded nanocarrier, NCf4) or Gemcitabine at 60 mg/kg via intraperitoneal injection, or a combination of Notch/Gemcitabine, each in the manner described, whereby Notch was Notch siRNA-loaded nanocarriers (prepared as described in Example 1 using fully stabilized XD-00409) treated via intravenous injection.

Treatments commenced on Day 0 and seven doses were administered. Clinical observations were made daily. Body weight and tumour size measurements were made three times weekly for the duration of the study.

Upon termination of the study (Day 24), tumours were harvested from all mice in all treatment groups, weighed and cut in half. One portion was preserved in RNAlater solution for isolation of RNA and qRT-PCR analysis. The remaining portion was preserved in formalin for paraffin embedding and microscopic assessment of necrosis.

Animal Study—Orthotopic Model

Sixty-six female athymic nude Foxn1$^{nu}$ mice were orthotopically inoculated with PANC-1 human pancreatic tumour cells. Take-rate was assessed in three mice each on Days 20 and 27 post-inoculation. Thirty-two days post-inoculation, the remaining 60 mice were randomised by body weight into six groups of ten (Day 0).

Mice in each group were treated twice weekly with Vehicle Control (unloaded nanocarrier, NCf4) Gemcitabine at 60 mg/kg via intraperitoneal injection, or a combination of Notch/Gemcitabine, each in the manner described, whereby Notch was Notch siRNA-loaded nanocarriers (prepared as described in Example 1 using fully stabilized XD-00409) treated via intravenous injection.

Treatments commenced on Day 0 and five doses were administered.

Clinical observations were made daily. Body weight measurements were made three times weekly for the duration of the study.

Upon termination of the study (Day 18), the intact tumor+pancreas was harvested from all mice in all treatment groups and weighed. Tumors were removed from the pancreas and cut in half. One portion was preserved in RNAlater solution for optional isolation of RNA and qRT-PCR analysis (not performed). The remaining portion was preserved in formalin for paraffin embedding and microscopic assessment of necrosis. The lungs and liver were harvested from all mice at termination. Both were weighed and assessed for surface metastases. The lungs and livers were preserved in formalin for paraffin embedding. Livers were assessed for the presence of micro-metastases.

EXAMPLE 2: EFFICACY OF NON-MODIFIED SIRNA TARGETING HUMAN NOTCH 1

Figure 1A:
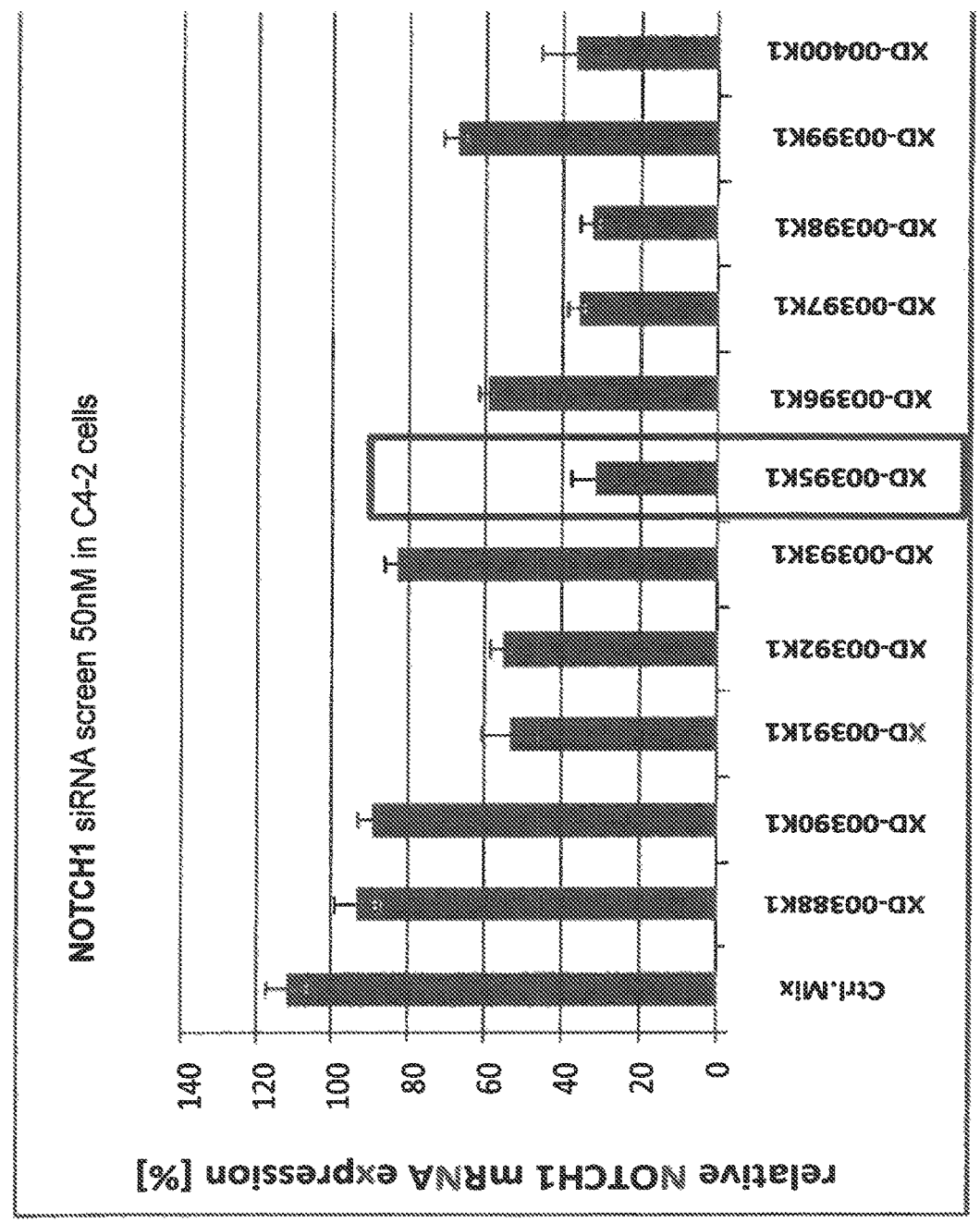
Figure 1B:
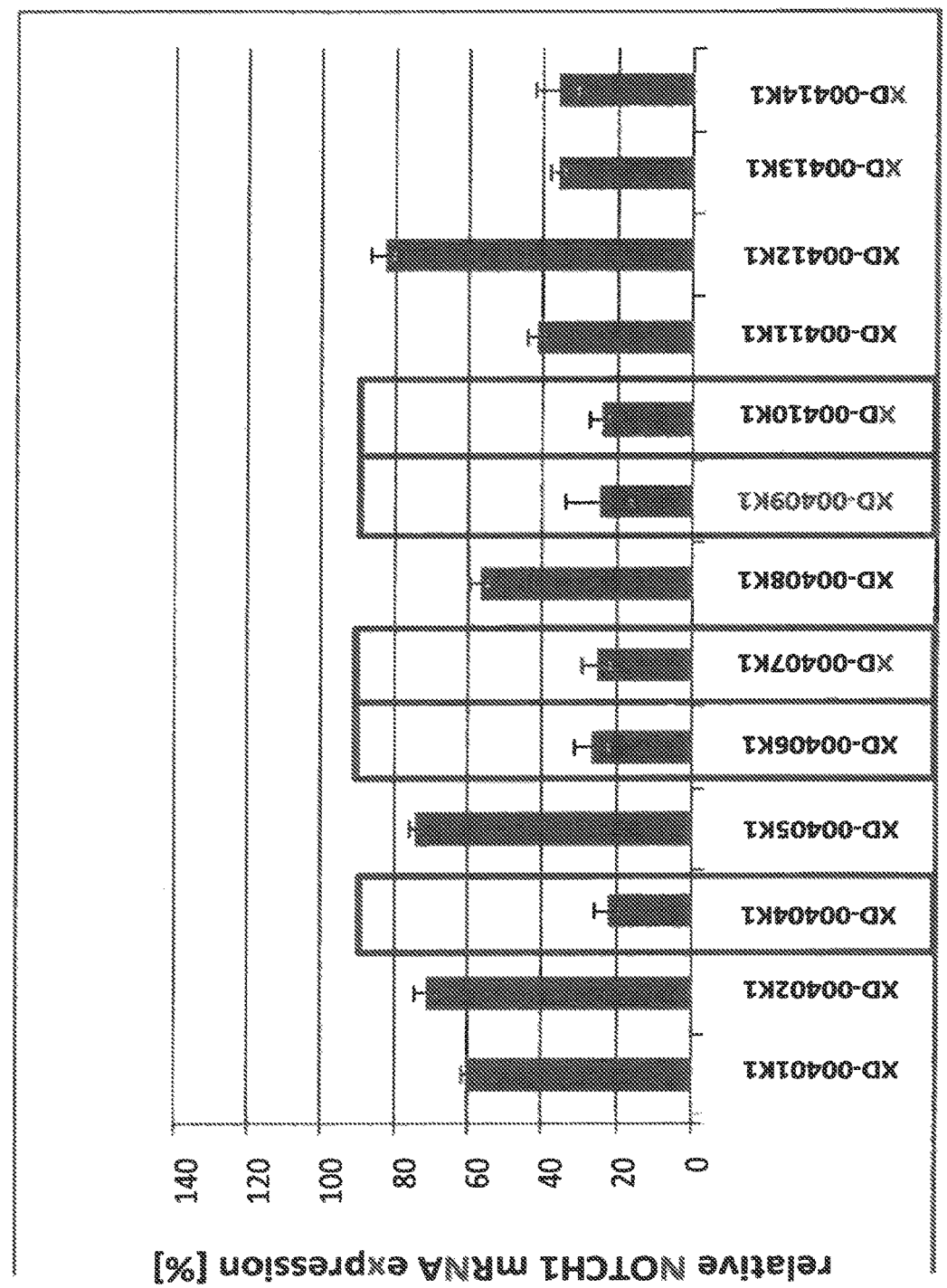
Figure 2A:
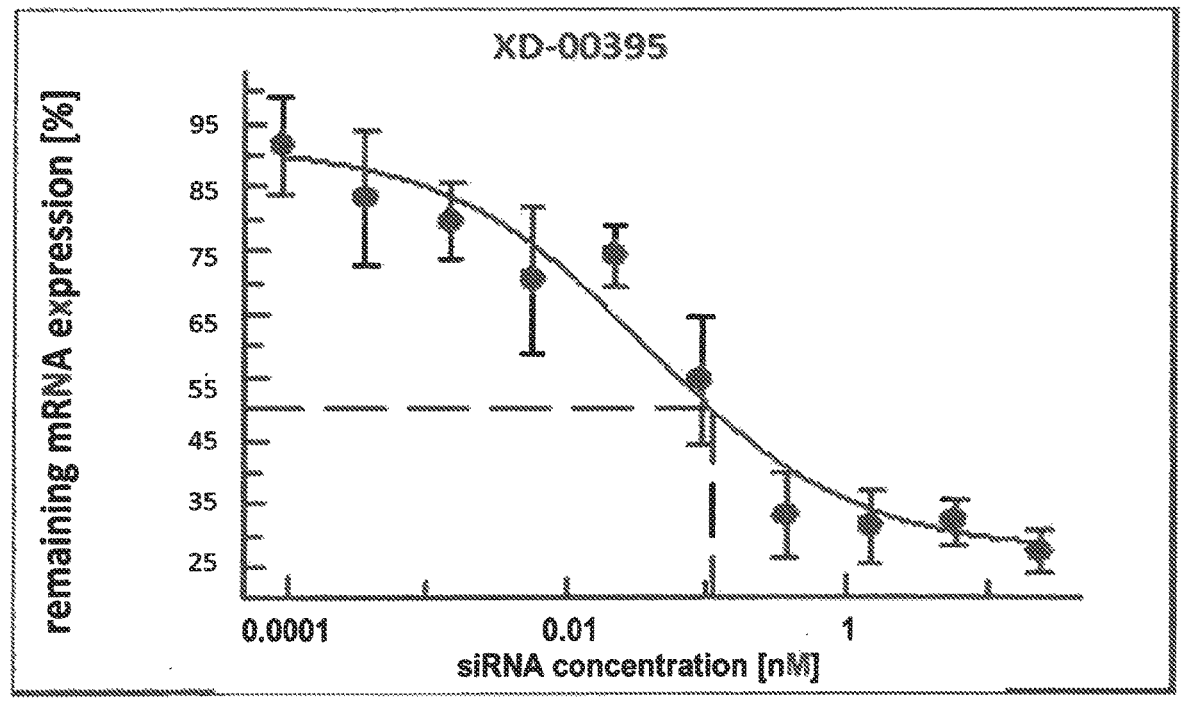
FIGS. 2A-2F are diagrams for various siRNAs indicating the remaining relative Notch 1 mRNA expression as a function of the concentration of the individual siRNA allowing the determination of the IC50 value for each siRNA.
Figure 2B:
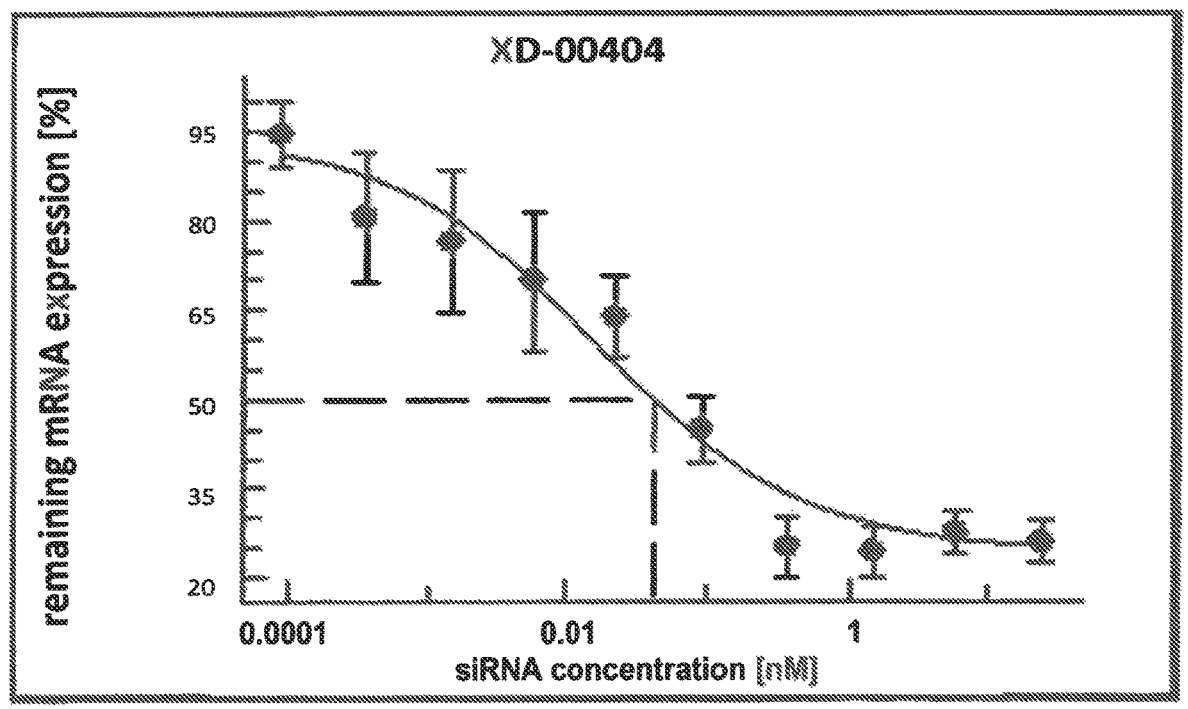
Figure 2C:
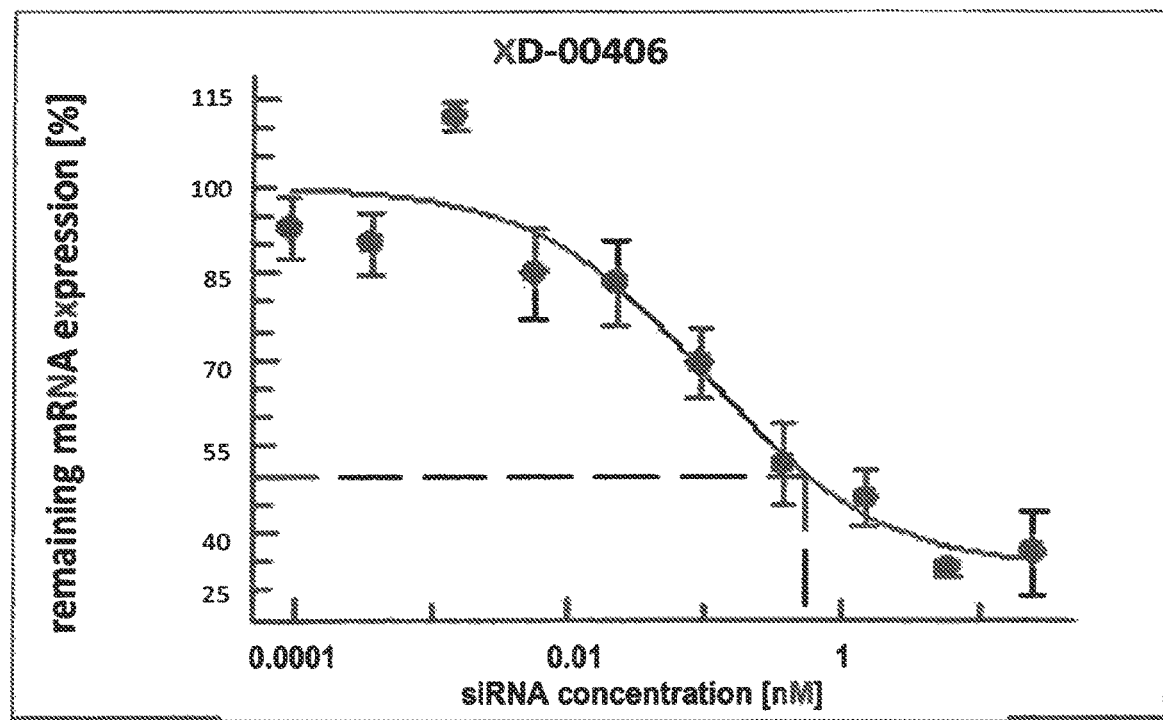
Figure 2D:
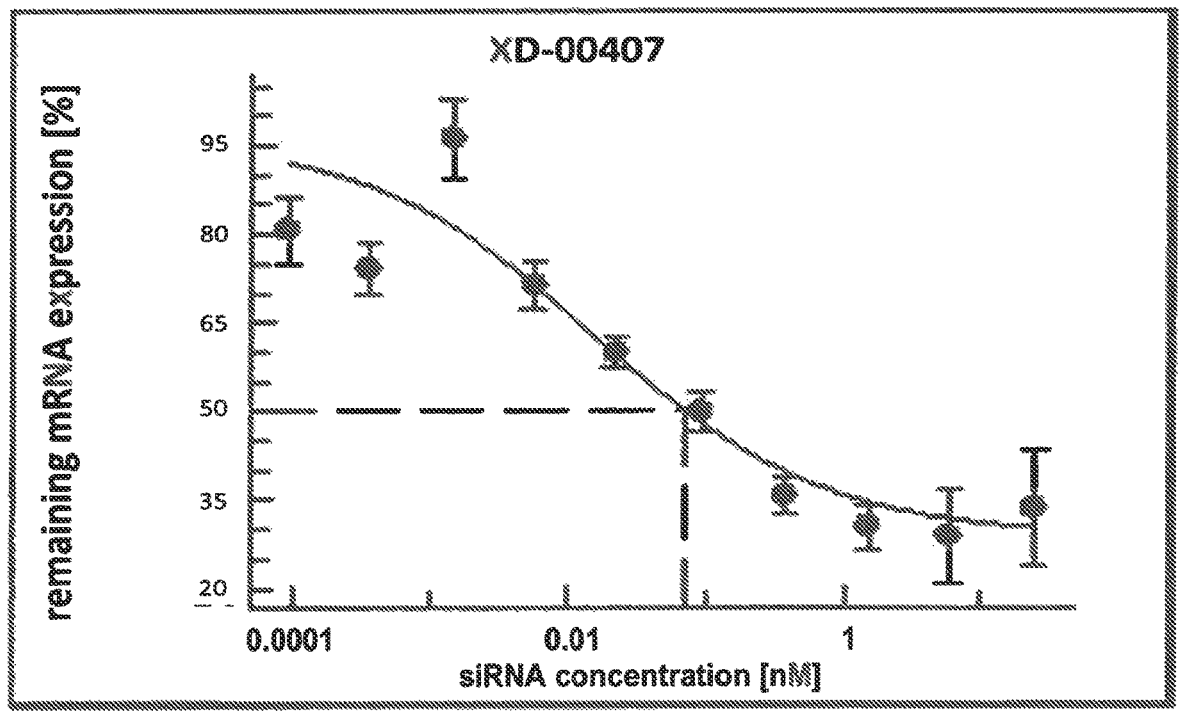
Figure 2E:
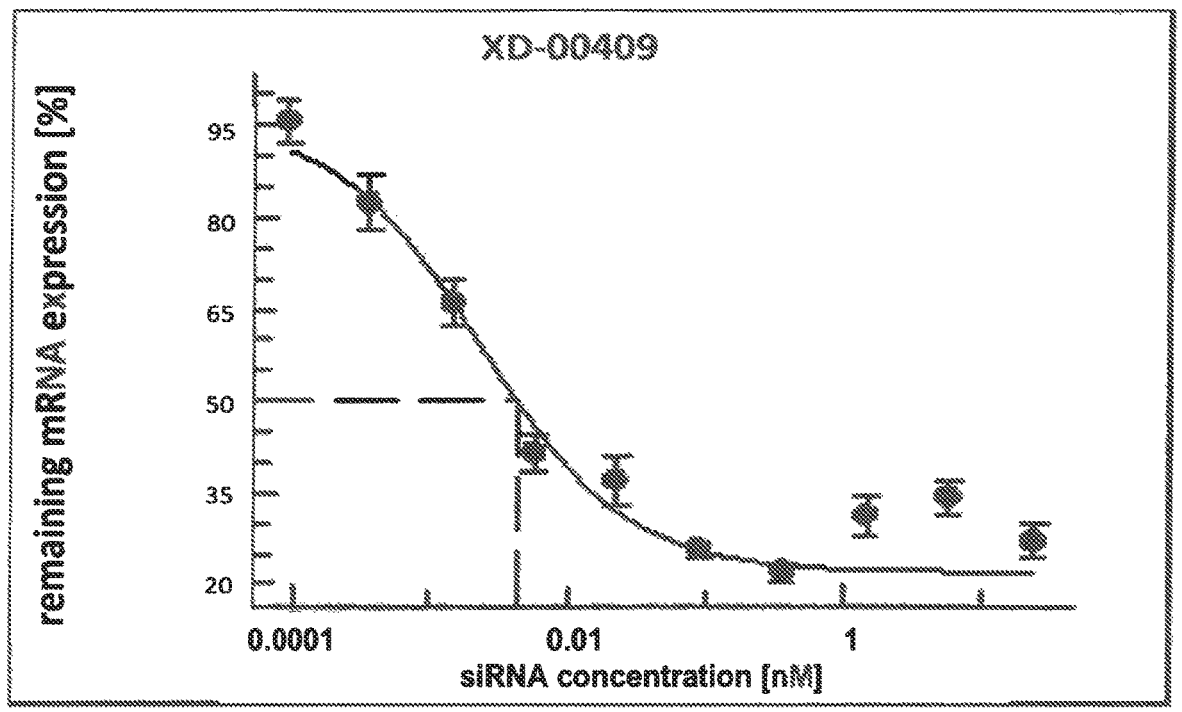
Figure 2F:
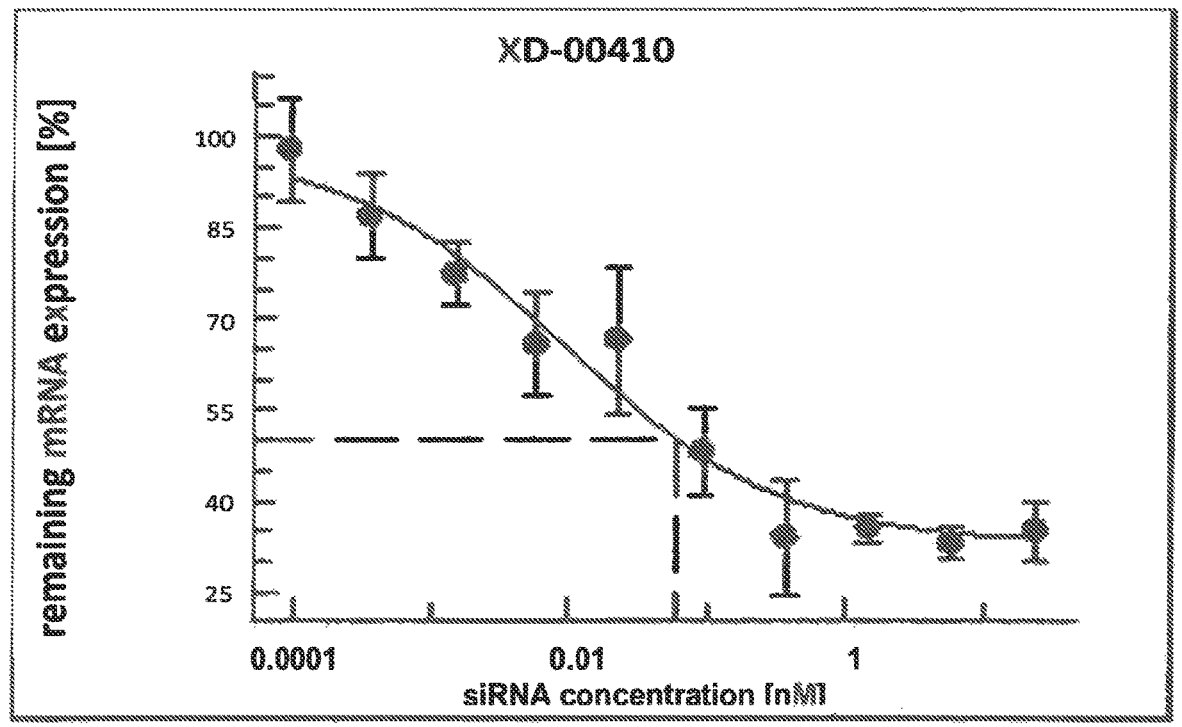

C4-2 cells were cultivated and transfected with the various siRNAs indicated in Table 1 as described in Example 1, whereby siRNA concentration was 50 nM. The results are shown in FIGS. 1A-1B. FIGS. 1A-1B are diagrams indicating the relative expression of Notch 1 upon transfection of C4-2 cells using various siRNAs. Expression is normalized to the expression of Notch 1 in C4-2 cells using a control. Control was a siRNA which is did not target any known mRNA coding for a protein.

As may be taken from FIGS. 1A-1B the best siRNAs show a knockdown of Notch 1 mRNA of almost 80%. It is also evident from FIGS. 1A-1B that a significant difference in efficacy of the various siRNAs exists.

The 6 siRNAs showing best knock-down are the ones of Table 2. These siRNAs were characterized further in terms of their IC50. The result is shown in FIGS. 2A-2F.

FIGS. 2A-2F are diagrams for each siRNA of Table 2 indicating the remaining relative Notch 1 mRNA expression as a function of the concentration of each siRNA. From said diagrams the IC50 for each of said siRNAs was calculated. The IC 50 values for said siRNA molecules are summarized in Table 3.

TABLE 3

| siRNA | $IC_{50}$ |
|---|---|
| XD-00409 | 0.0043 |
| XD-00404 | 0.042 |
| XD-00410 | 0.061 |
| XD-00407 | 0.073 |
| XD-00395 | 0.111 |
| XD-00406 | 0.545 |

As may be taken from both FIGS. 2A-2F and Table 3 the best siRNA molecule in terms of IC50 is XD-00409 having an IC50 of 4.3 pM.

EXAMPLE 3: EFFICACY OF MODIFIED SIRNA TARGETING HUMAN NOTCH 1 siRNA molecules XD00404 and XD-00409 of Tables 1 and 2 were subject to intermediate stabilization and full stabilization as also described in Example 1. The accordingly modified siRNA molecules are as follows
a) XD-00404 with intermediate stabilization (also referred to as XD-00751):
b) XD-00404 with full stabilization (also referred to as XD-00752):
c) XD-00409 with intermediate stabilization (also referred to as XD-00753):
d) XD-00409 with full stabilization (also referred to as XD-00754):

These siRNA molecules were tested as to their efficacy in C4-2 cells upon transfection of said C4-2 cells as described in Example 1, whereby the concentration of the siRNA was 10 nM, 1 nM or 0.1 nM in the transfection experiment.

Figure 3A:
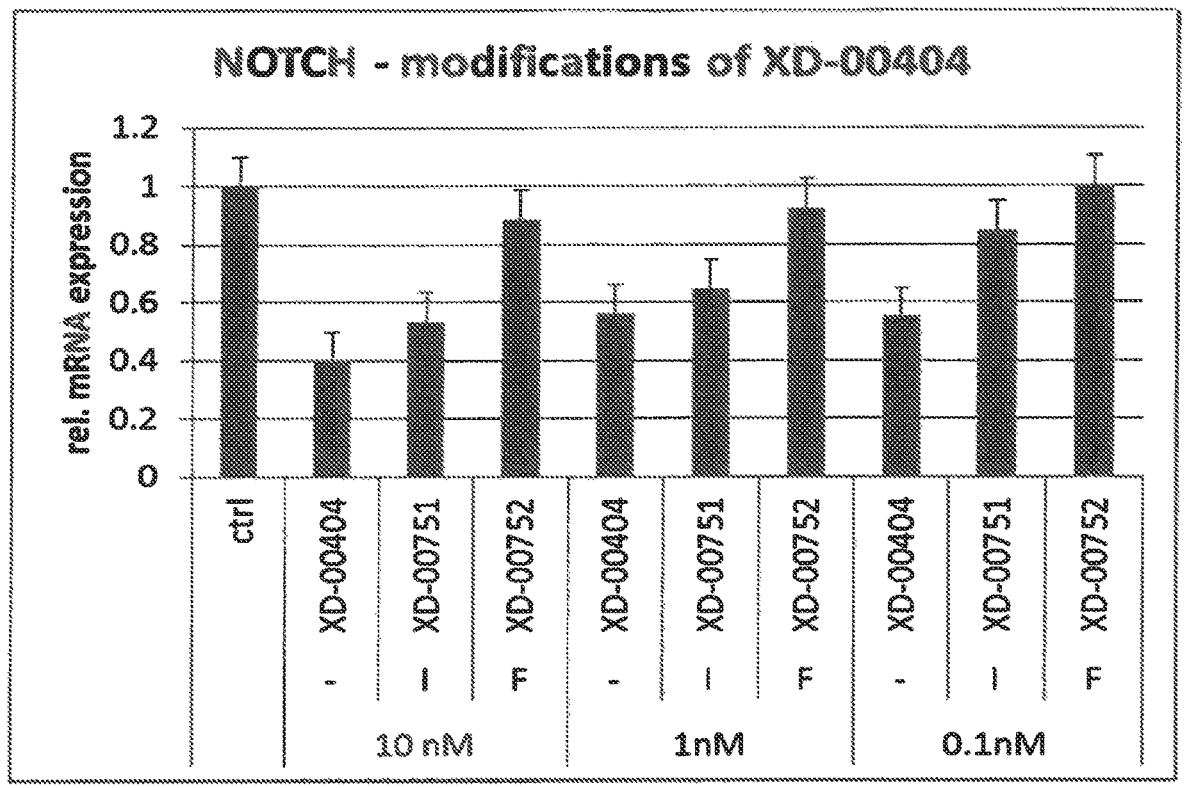
FIGS. 3A and 3B are diagrams showing relative Notch 1 mRNA expression upon exposure of C4-2 cells to siRNA XD-00404 (FIG. 3A) or XD-00409 (FIG. 3B) in its unmodified, intermediate or fully modified form at a concentration of 10 nM, 1 nm and 0.1 nM.
Figure 3B:
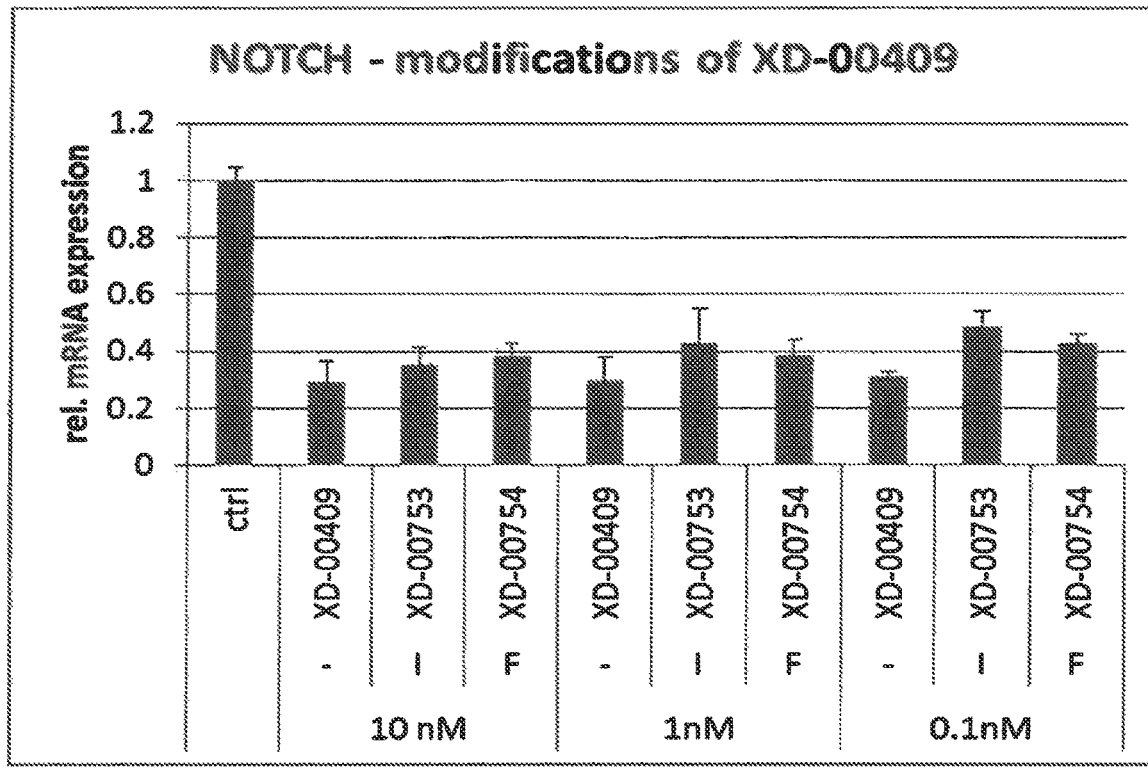

The results of such experiments are shown in FIG. 3A for siRNA XD-00404 in its unmodified, intermediate or fully modified form and for siRNA XD-00409 in its unmodified, intermediate or fully modified form and in FIG. 3B as relative mRNA expression using a control. Control was a siRNA which is did not target any known mRNA coding for a protein.

As may be taken from FIGS. 3A-3B, although modification of the siRNA molecule is beneficial in terms of stability, it is evident that modification of both siRNAs (XD-00404 and XD-00409) is reducing its efficacy of the knock-down of the expression of the Notch 1 mRNA. It has, however, surprisingly found that the impact of modification on XD-00409 is less pronounced and factually not existing compared to the impact of modification on XD-00404. Insofar, siRNA DX-00409 shows surprising and unexpected effects.

EXAMPLE 4: EFFECT OF SIRNA TARGETING HUMAN NOTCH 1 IN A XENOGRAFT PANCREAS TUMOR MODEL

The animal study using PANC-1 human pancreatic tumours as described in Example 1 was carried out. The siRNA species used was fully stabilized XD-00409.

The results of the study can be summarized as follows:
Body weight loss was not evident. A small mass was present under the front leg in a total of 10 mice in the study.
Mild tumour inhibition was evident following treatment with Gemcitabine monotherapy, and combination of Notch/Gemcitabine, indicated by measurements of percentage tumour growth and tumour weight, but only Notch/Gemcitabine combination therapy was significantly different to the Vehicle in regards to tumour weight. A synergistic response in tumour inhibition, measured by percentage tumour growth, was exhibited by combination therapy Notch/Gemcitabine.
Mice treated with Gemcitabine monotherapy and Notch/Gemcitabine combination therapy had the lowest occurrence of tumour necrosis.

The result of said animal study is also shown in FIG. 4. FIG. 4 is a diagram showing the relative increase in tumour volume (indicated as %±SEM) over time using control ("Vehicle (NCF4)"), gemcitabine ("Gemcitabine") and a combination of gemcitabine and the Notch siRNA-loaded nanocarrier ("Notch/Gemcitabine"). Each of the agents or combination agent was administered 2× weekly.

EXAMPLE 5: EFFECT OF SIRNA TARGETING HUMAN NOTCH 1 IN AN ORTHOTOPIC PANCREATIC TUMOR MODEL

The animal study using PANC-1 human pancreatic tumours as described in Example 1 was carried out. The siRNA species used was fully stabilized XD-00409.

The results of the study can be summarized as follows:
The number of animals without metastases based on PANC-1 cells was significantly reduced as shown in FIG. 5 in case of the animals which received a combination of gemcitabine and the Notch siRNA-loaded nanocarrier compared to the animals receiving either control or only gemcitabine. More specifically, upon treatment of ten animals with vehicle alone, three animals had several metastases, three animals had single metastasis and four animals were without metastases; upon treatment of ten animals with Gemcitabine alone, two animals had several metastases, four animals had single metastasis and four animals were without metastases; and upon treatment of ten animals with both gemcitabine and siRNA-loaded nanocarriers using fully modified XD-00409, one animal had several metastases, one animal had single metastasis and eight animals were without metastases.

Furthermore, treatment with Gemcitabine in combination with Notch 1 specific siRNA (fully stabilized XD-00409), was associated with significant mean body weight loss and with loss of body condition in two mice.

The content and disclosure of the various references recited herein is incorporated herein by reference in their entirety.

The features of the present invention disclosed in the specification, the claims and/or the drawings may both separately and in any combination thereof be material for realizing the invention in various forms thereof.

The invention claimed is:

1. A nucleic acid molecule comprising a double-stranded structure, wherein the double-stranded structure is formed by a first strand and a second strand, wherein the first strand comprises the following nucleotide sequence Seq ID No.: 14
　　5' ACGAGCUGGACCACUGGUC 3', and the second strand comprises the following nucleotide sequence Seq ID No.: 3
　　5' GACCAGUGGUCCAGCUCGU 3'.

2. A nucleic acid molecule comprising a double-stranded structure, wherein the double-stranded structure is formed by a first strand and a second strand, wherein the first strand comprises the following nucleotide sequence Seq ID No.: 4
　　5' ACGAGCUGGACCACUGGUCdTsdT 3', and the second strand comprises the following nucleotide sequence Seq ID No.: 5
　　5' GACCAGUGGUCCAGCUCGUdTsdT 3', wherein dTsdT indicates that at the 3' end a dinucleotide is attached consisting of two dT nucleotides, wherein said two dTs are covalently linked through a phosphorothioate bond.

3. The nucleic acid molecule of claim 1, wherein the nucleic acid molecule is capable of causing post-transcriptional silencing of a gene.

4. The nucleic acid molecule of claim 3, wherein the gene is human Notch 1.

5. The nucleic acid molecule of claim 1, wherein post-transcriptional silencing is RNA interference.

6. The nucleic acid molecule of claim 3, wherein post-transcriptional silencing is RNA interference.

7. The nucleic acid molecule of claim 4, wherein post-transcriptional silencing is RNA interference.

8. A method for restoring drug sensitivity of cancer cells by administering the nucleic acid molecule of claim 1 to the cancer cells, wherein the cancer cells exhibit Notch 1 induced chemoresistance.

9. A method for restoring drug sensitivity of cancer cells by administering the nucleic acid molecule of claim 4 to the cancer cells, wherein the cancer cells exhibit Notch 1 induced chemoresistance.

10. The nucleic acid molecule of claim 4, wherein said nucleic acid molecule is used in a method for restoring drug sensitivity of cancer cells, and wherein the cancer cells exhibit Notch 1 induced chemoresistance.

11. A nanoemulsion comprising a discontinuous phase and a continuous aqueous phase and a nucleic acid molecule of claim 1.

12. A nanoemulsion comprising a discontinuous phase and a continuous aqueous phase and a nucleic acid molecule of claim 3.

13. A nanoemulsion comprising a discontinuous phase and a continuous aqueous phase and a nucleic acid molecule of claim 4.

14. The nanoemulsion of claim 11, wherein the discontinuous phase comprises a perfluorocarbon phase.

15. The nanoemulsion of claim 12, wherein the discontinuous phase comprises a perfluorocarbon phase.

16. The nanoemulsion of claim 13, wherein the discontinuous phase comprises a perfluorocarbon phase.

17. The nanoemulsion of claim 11, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

18. The nanoemulsion of claim 12, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

19. The nanoemulsion of claim 13, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

20. The nanoemulsion of claim 14, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

21. The nanoemulsion of claim 15, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

22. The nanoemulsion of claim 16, wherein the nanoemulsion comprises an endocytosis enhancing surface, the endocytosis enhancing surface comprises an endocytosis enhancing component, wherein the endocytosis enhancing component is selected from the group comprising at least one compound inducing cellular uptake of the nanoemulsion or particles of the nanoemulsion via endocytosis.

23. A method of treating a disease in a subject comprising administering the nanoemulsion of claim 11 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

24. A method of treating a disease in a subject comprising administering the nanoemulsion of claim 12 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

25. A method of treating a disease in a subject comprising administering the nanoemulsion of claim 13 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

26. A method of treating a disease in a subject comprising administering the nanoemulsion of claim 14 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

27. A method of treating a disease in a subject comprising administering the nanoemulsion of claim 15 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

28. A method of treating a disease in a subject comprising administering the nanoemulsion of claim 16 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

29. A method of treating a disease in a subject comprising administering the nanoemulsion of claim 17 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

30. A method of treating a disease in a subject comprising administering the nanoemulsion of claim 18 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

31. A method of treating a disease in a subject comprising administering the nanoemulsion of claim 18 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

32. A method of treating a disease in a subject comprising administering the nanoemulsion of claim 19 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

33. A method of treating a disease in a subject comprising administering the nanoemulsion of claim 21 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

34. A method of treating a disease in a subject comprising administering the nanoemulsion of claim 22 to the subject, wherein the disease is selected from the group comprising esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

35. The nanoemulsion of claim 11, further comprising a pharmaceutically active agent.

36. A method for restoring drug sensitivity of cancer cells, by administering the microemulsion of claim 11, wherein the cancer cells exhibit Notch 1 induced chemoresistance.

37. A pharmaceutical composition comprising a nucleic acid molecule of claim 1, and at least one pharmaceutically active excipient.

38. A pharmaceutical composition comprising a nucleic acid molecule of claim 3, and at least one pharmaceutically active excipient.

39. A pharmaceutical composition comprising a nucleic acid molecule of claim 4, and at least one pharmaceutically active excipient.

40. A pharmaceutical composition comprising a nucleic acid molecule of claim 5, and at least one pharmaceutically active excipient.

41. A pharmaceutical composition, wherein said composition comprises the nanoemulsion of claim 11 and at least one pharmaceutically active ingredient.

42. A kit comprising a nucleic acid molecule of claim 1.
43. A kit comprising a nucleic acid molecule of claim 3.
44. A kit comprising a nucleic acid molecule of claim 4.
45. A kit comprising a nucleic acid molecule of claim 5.
46. A kit comprising a nucleic acid molecule of claim 6.
47. A kit comprising a nucleic acid molecule of claim 7.
48. A kit comprising a nanoemulsion of claim 11.
49. A kit comprising a nanoemulsion of claim 12.
50. A kit comprising a nanoemulsion of claim 13.

51. A method for treating a disease, wherein the method comprises: administering to a subject the nucleic acid molecule of claim 1, and wherein the disease is selected from the group consisting of esophageal cancer, oral squamous cell carcinoma, head and neck cancer, tonge cancer, leukemia, renal cell carcinoma, gastric cancer, colon adenocarcinoma, endometrial cancer/uterine corpus, cervical cancer/uterine cervix, introsepatic cholongiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

52. A method for treating a disease, wherein the method comprises: administering to a subject the nucleic acid molecule of claim 4, and wherein the disease is selected from the group consisting of esophageal cancer, oral squamous cell carcinoma, head and neck cancer, tongue cancer, leukemia, renal cell carcinoma, gastric cancer, colon adenocarcinoma, endometrial cancer/uterine corpus, cervical cancer/uterine cervix, intrahepatic cholangiocarcinoma, hepatocellular carcinoma, osteosarcoma, urinary bladder carcinoma, malignant melanoma, thyroid cancer, lung adenocarcinoma, prostate cancer, breast cancer, ovarian cancer, pancreatic cancer and glioma.

* * * * *